US009681851B2

(12) United States Patent
Rohler et al.

(10) Patent No.: US 9,681,851 B2
(45) Date of Patent: Jun. 20, 2017

(54) METHODS AND APPARATUS FOR EXTENDED LOW CONTRAST DETECTABILITY FOR RADIOGRAPHIC IMAGING SYSTEMS

(71) Applicants: David P. Rohler, Shaker Heights, OH (US); Thomas L. Toth, Brookfield, WI (US); Steven H. Izen, Shaker Heights, OH (US); Arjun K. Maniyedath, Shaker Heights, OH (US)

(72) Inventors: David P. Rohler, Shaker Heights, OH (US); Thomas L. Toth, Brookfield, WI (US); Steven H. Izen, Shaker Heights, OH (US); Arjun K. Maniyedath, Shaker Heights, OH (US)

(73) Assignee: TIP Imaging, LLC, Shaker Heights, OH (US)

( * ) Notice: Subject to any disclaimer, the term of this patent is extended or adjusted under 35 U.S.C. 154(b) by 1 day.

(21) Appl. No.: 14/542,698

(22) Filed: Nov. 17, 2014

(65) Prior Publication Data
US 2015/0282781 A1 Oct. 8, 2015

Related U.S. Application Data

(63) Continuation of application No. 13/837,448, filed on Mar. 15, 2013, now abandoned, and a
(Continued)

(51) Int. Cl.
*A61B 6/03* (2006.01)
*A61B 6/00* (2006.01)

(52) U.S. Cl.
CPC .............. *A61B 6/583* (2013.01); *A61B 6/032* (2013.01); *A61B 6/482* (2013.01); *A61B 6/488* (2013.01);
(Continued)

(58) Field of Classification Search
CPC ......... A61B 6/032; A61B 6/482; A61B 6/488; A61B 6/542; A61B 6/544; A61B 6/545; A61B 6/583; A61B 6/584; A61B 6/586
(Continued)

(56) References Cited

U.S. PATENT DOCUMENTS 5,442,674 A * 8/1995 Picard .................... A61B 6/583
378/18
6,272,200 B1 * 8/2001 Pan ....................... G06T 11/005
378/15
(Continued)

OTHER PUBLICATIONS

Damien Racine et al., Objective assessment of low contrast detectability in computed tomography with Channelized Hotelling Observer, Physica Medica 32 (2016), 76-83.*
(Continued)

*Primary Examiner* — Allen C. Ho
(74) *Attorney, Agent, or Firm* — Ulmer & Berne LLP

(57) ABSTRACT

Evaluating dose performance of a radiographic imaging system with respect to image quality using a phantom, a channelized hotelling observer module as a model observer, and a printer, a plaque, or an electronic display includes scanning and producing images for a plurality of sections of the phantom using the radiographic imaging system, wherein the plurality of sections represent a range of patient sizes and doses and wherein the sections of the phantom contain objects of measurable detectability. Also included is analyzing the images to determine detectability results for one or more of the contained objects within the images of the plurality of sections of the phantom, wherein the analyzing includes using a channelized hotelling observer (CHO) module as a model observer; and displaying, via the printer, the plaque, or the electronic display, a continuous detectability performance measurement function using the determined detectability results.

16 Claims, 38 Drawing Sheets

Related U.S. Application Data continuation-in-part of application No. 13/503,721, filed as application No. PCT/US2010/002006 on Jul. 16, 2010, now Pat. No. 8,891,849.

(60) Provisional application No. 61/271,150, filed on Jul. 17, 2009, provisional application No. 61/278,954, filed on Oct. 14, 2009.

(52) U.S. Cl.
CPC .............. *A61B 6/542* (2013.01); *A61B 6/544* (2013.01); *A61B 6/545* (2013.01); *A61B 6/584* (2013.01); *A61B 6/586* (2013.01)

(58) Field of Classification Search
USPC .......................................... 378/16, 18, 207
See application file for complete search history.

(56) References Cited

U.S. PATENT DOCUMENTS

| | | | |
|---|---|---|---|
| 6,697,451 B2 * | 2/2004 | Acharya | A61B 6/583 250/363.04 |
| 6,715,918 B2 * | 4/2004 | Mitschke | A61B 6/583 378/163 |
| 6,778,628 B2 * | 8/2004 | Yamazaki | A61B 6/032 378/4 |
| 6,851,855 B2 * | 2/2005 | Mitschke | A61B 6/547 378/205 |
| 6,944,258 B2 * | 9/2005 | Nukui | A61B 6/032 378/19 |
| 6,959,106 B1 * | 10/2005 | Toth | A61B 6/583 250/252.1 |
| 6,990,171 B2 * | 1/2006 | Toth | A61B 6/032 378/158 |
| 7,016,456 B2 * | 3/2006 | Basu | A61B 6/583 378/18 |
| 7,068,750 B2 * | 6/2006 | Toth | A61B 6/032 378/156 |
| 7,068,751 B2 * | 6/2006 | Toth | A61B 6/032 378/20 |
| 7,088,849 B1 * | 8/2006 | Toth | A61B 6/583 250/252.1 |
| 7,147,373 B2 * | 12/2006 | Cho | A61B 6/547 378/164 |
| 7,149,277 B2 * | 12/2006 | Tanigawa | A61B 6/032 378/18 |
| 7,186,023 B2 * | 3/2007 | Morita | A61B 6/466 378/18 |
| 7,313,217 B2 * | 12/2007 | Toth | A61B 6/032 378/20 |
| 7,339,159 B2 * | 3/2008 | Juh | A61B 6/12 250/252.1 |
| 7,372,936 B2 * | 5/2008 | Nukui | A61B 6/032 378/150 |
| 7,510,325 B2 * | 3/2009 | Endo | A61B 6/032 250/252.1 |
| 7,535,987 B2 * | 5/2009 | Matsuda | G01N 23/046 378/159 |
| 7,627,079 B2 * | 12/2009 | Boone | G01T 1/2985 378/210 |
| 7,660,379 B2 * | 2/2010 | Scholz | G06T 11/005 378/18 |
| 7,686,510 B2 * | 3/2010 | Yeh | G01T 7/005 378/119 |
| 7,755,031 B2 * | 7/2010 | Jang | A61B 6/5276 250/252.1 |
| 7,756,312 B2 * | 7/2010 | Hsieh | G06T 7/0002 378/21 |
| 7,778,380 B2 * | 8/2010 | Altman | G06T 7/0004 378/4 |
| 7,780,351 B2 * | 8/2010 | Heigl | A61B 6/032 378/4 |
| 7,822,172 B2 * | 10/2010 | Ruhrnschopf | G01N 23/04 378/19 |
| 7,866,884 B2 * | 1/2011 | Seto | A61B 6/541 378/18 |
| 7,950,849 B2 * | 5/2011 | Claus | G06T 11/005 378/18 |
| 8,007,173 B2 * | 8/2011 | Paidi | A61B 6/584 378/207 |
| 8,075,183 B2 * | 12/2011 | Thornton | A61B 6/583 378/18 |
| 8,104,958 B2 * | 1/2012 | Weiser | A61B 6/583 378/162 |
| 8,121,250 B2 * | 2/2012 | Dafni | A61B 6/032 378/18 |
| 8,220,994 B2 * | 7/2012 | Heigl | A61B 6/547 378/207 |
| 8,308,362 B2 * | 11/2012 | Dove | A61B 6/145 378/204 |
| 8,628,241 B2 * | 1/2014 | Kappler | A61B 6/032 378/18 |
| 8,737,707 B2 * | 5/2014 | Pearlstein | A61B 6/583 378/204 |
| 8,777,485 B2 * | 7/2014 | Holt | A61B 6/03 250/252.1 |
| 8,891,849 B2 * | 11/2014 | Rohler | A61B 6/032 382/132 |
| 9,230,354 B2 * | 1/2016 | O'Connor | A61B 6/482 |

OTHER PUBLICATIONS

Jovan G. Brankov, Evaluation of Channelized Hotelling Observer with Internal-Noise Model in a Train-Test Paradigm for Cardiac SPECT defect detection, Phys. Med. Biol. 58 (2013) 7159-7182.*

Harrison H. Barrett et al., Model observers for assessment of image quality, Proc. Natl. Acad. Sci. USA 1993 vol. 90 (21), 9758-9765.*

L. Noferini et al., CT image quality assessment by a Channelized Hotelling Observer (CHO): Application to protocol optimization, Physica Medica 32 (2016), 1717-1723.*

Justin Solomon et al., Comparison of low-contrast detectability between two CT reconstruction algorithms using voxel-based 3D printed textured phantoms, Medical Physics 43(12), Dec. 2016, 6497-6506.*

F. R. Verdun et al., Image quality in CT: From physical measurements to model observers, Physica Medica 31 (2015) 823-843.*

Brendan L. Eck et al., Computational and human observer image quality evaluation of low dose, knowledge-based CT iterative reconstruction, Medical Physics 42(10), Oct. 2015, 6098-6111.*

Ganesh Saiprasad et al., Evaluation of Low-Contrast Detectability of Iterative Reconstruction across Multiple Institutions, CT Scanner Manufacturers, and Radiation Exposure Levels, Radiology: vol. 277: No. 1, Oct. 2015, 124-133.*

Jingyan Xu et al., Task-based image quality evaluation of iterative reconstruction methods for low dose CT using computer simulations, Physics in Medicine and Biology 60 (2015), 2881-2901.*

Shishir Raj Adhikari, Plexar Imaging: A Startup Determined to Solve the CT Dose Variability Problem, Master of Sciences, Department of Physics, Case Western Reserve University, Aug. 2013.*

Lifeng Yu et al., Prediction of human observer performance in a 2-alternative forced choice low-contrast detection task using channelized Hotelling observer: Impact of radiation dose and reconstruction algorithms, Medical Physics 40(4), Apr. 2013, 041908.*

Adam Wunderlich and Frédéric Noo, New Theoretical Results on Channelized Hotelling Observer Performance Estimation with Known Difference of Class Means, IEEE Transaction on Nuclear Science, vol. 60, No. 1, Feb. 2013, 182-193.*

Adam Wunderlich and Frédéric Noo, Practical Estimation of Detectability Maps for Assessment of CT Scanner Performance, IEEE Nuclear Science Symposium Conference Record, Nov. 2010, 2801-2804.*

Adam Wunderlich and Frédéric Noo, Image covariance and lesion detectability in direct fan-beam x-ray computed tomography, Physics in Medicine and Biology 53 (2008), 2471-2493.*

(56) References Cited

OTHER PUBLICATIONS

Jing Wang et al., Penalized Weighted Least-Squares Approach to Sinogram Noise Reduction and Image Reconstruction for Low-Dose X-Ray Computed Tomography, IEEE Transactions on Medical Imaging, vol. 25, No. 10, Oct. 2006, 1272-1283.*

* cited by examiner

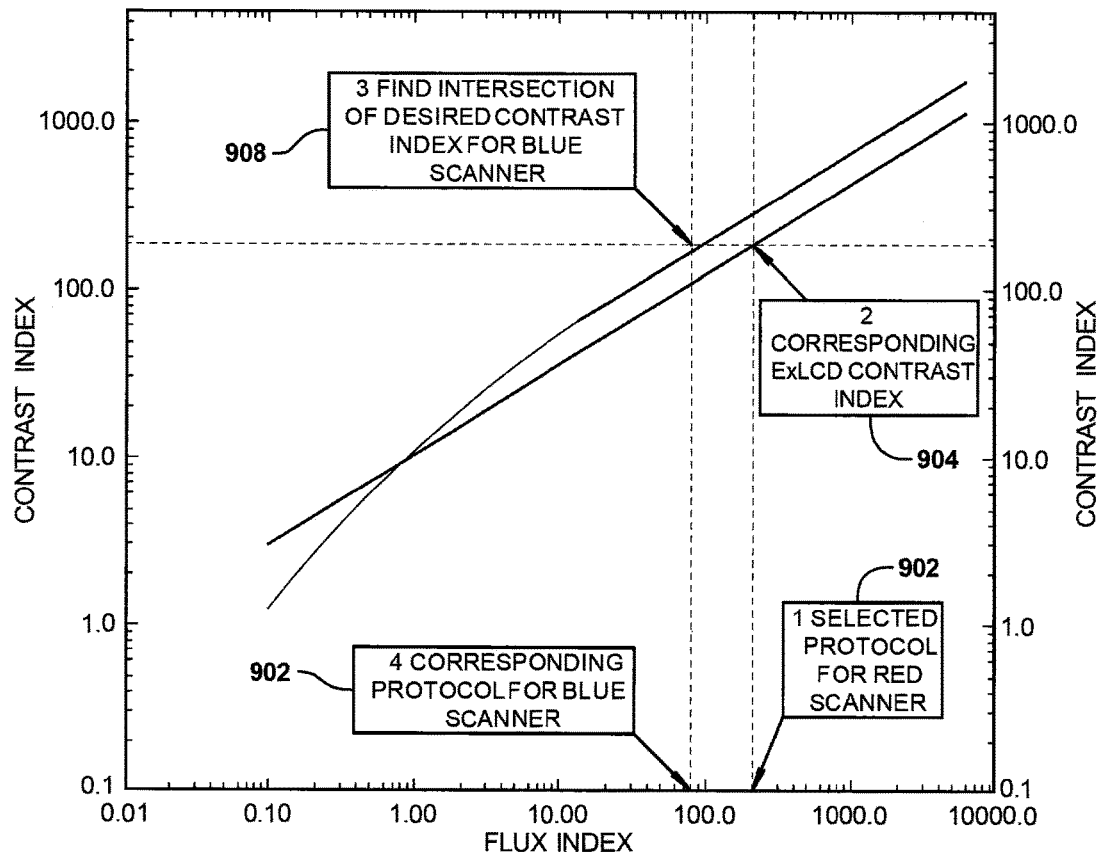
ILLUSTRATION OF METHOD FOR DEVELOPING STANDARDIZED PROTOCOLS BETWEEN TWO DISTINCT SCANNERS.
FIG 9
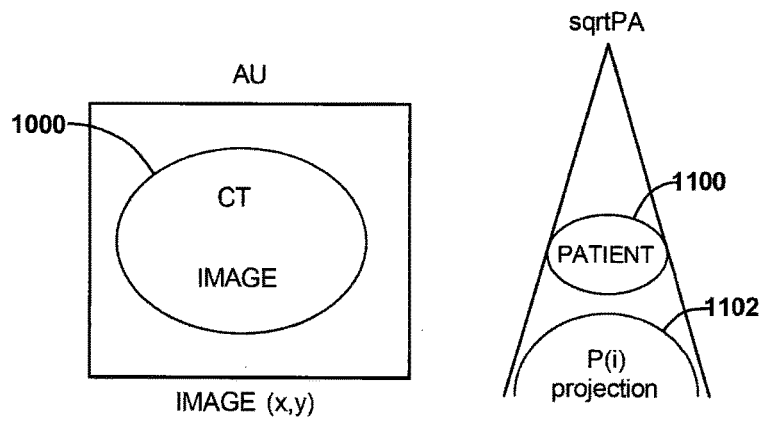
FIG 10     FIG 11

BLOCK DIAGRAM FOR ExLCD METHOD

UPPER: CONTRAST MEASUREMENTS OVER THE ENTIRE FLUX RANGE.
LOWER: CONTRAST PERFORMANCE CURVE DERIVED FROM CONTRAST MEASUREMENTS.

DOSE COMPARISON FOR EQUIVALENT CONTRAST DETECTABILITY FOR THREE DIFFERENT CONTRAST PERFORMANCE CURVES.

PIN SIZE SAMPLING AND CONTRAST SET SAMPLING. EACH COLOR REPRESENTS A DISTINCT CONTRAST SET. CONTRAST SETS ARE INTERLEAVED (DOTTED LINES) WITH THE SMALLEST PIN OF ANY CONTRAST SET POSITIONED BETWEEN THE 4TH AND 5TH PINS OF THE NEXT LOWER CONTRAST LEVEL.

ExLCD PHANTOM CONFIGURATION SHOWING TWO DISTINCT DIAMETERS AND 9 DISTINCT CONTRAST SETS

CROSS SECTIONS OF THE ExLCD (SIMULATED) PHANTOM SHOWING A 20cm CROSS-SECTION (LEFT) AND A 40cm CROSS- SECTION (RIGHT).

THE TWO-DIMENSIONAL CROSS-SECTION OF ALTERNATIVE EMBODIMENTS OF AN ExLCD PHANTOM.

CONTRAST SETS REPRESENTED AT EACH PROTOCOL.
THE HATCHED REGION REPRESENTS THE APPROXIMATE REQUIRED COVERAGE.

ILLUSTATION OF A DETECTABILITY MAPPING. PINS ARE NUMBERED 1-9 FROM LARGEST TO SMALLEST. MAPPING FROM SELECTED SMALLEST PINS TO ExLCD CONTRAST MEASURE PLOT.

AFTER ALL ORDERED PAIRS ARE MAPPED TO THE ExLCD GRAPH, A CONTRAST PERFORMANCE CURVE CAN BE DETERMINED BY (LEAST SQUARES) FITTING ORDERED PAIRS TO CURVE.

ExLCD GRAPH: CONTRAST INDEX TRACKS DETECTABILITY / IMAGE QUALITY; FLUX INDEX TRACKS DOSE / PATIENT SIZE.

RED: LEV1, GREE: LEV2, BLU: LEV3, PURP: LEV4, GRAY: LEV5, ORNG: LEV6, TURQ: LEV7, D.GREEN: LEV8, D.RED: LEV

ROSE CRITERION VISIBILITY INDEX (UPPER) AND CORRESPONDING ExLCD CONTRAST INDEX (LOWER).

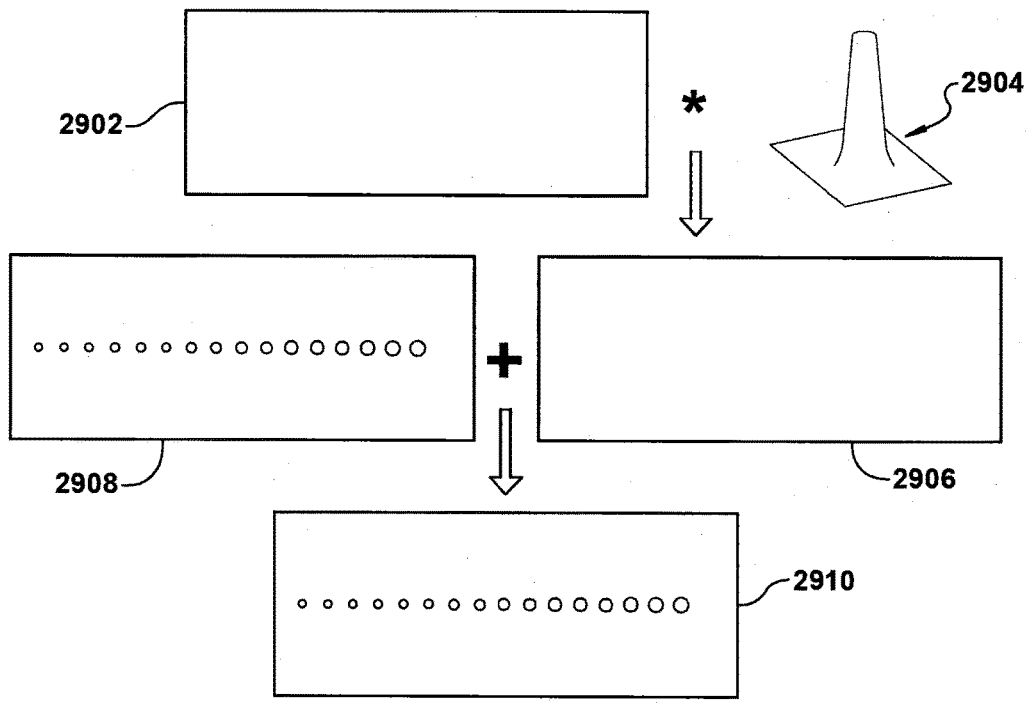

ILLUSTRATION OF MATCHED FILTER DETECTABILITY ANALYSIS. THE RECONSTRUCTED IMAGE NOISE FIELD (TOP ROW) IS CONVOLVED WITH THE IDEAL RECONSTRUCTED IMAGE OF THE PIN. A SEQUENCE OF 15 IDEAL RECONSTRUCTED PINS IS COMBINED WITH THE FILTERED NOISE FIELD (MIDDLE ROW) TO PRODUCE AN IMAGE (BOTTOM ROW) THAT ILLUSTRATES THE CONTRAST AMPLITUDE NECESSARY TO ACHIEVE DETECTABILITY ABOVE THE SPECIFIED THRESHOLD.

FIG 29

UPPER: COLLECTION OF ORDERED PAIRS, [FLUX INDEX, CONTRAST INDEX]
LOWER: LEAST-SQUARES FIT TO 2-PARAMETER EQUATION.

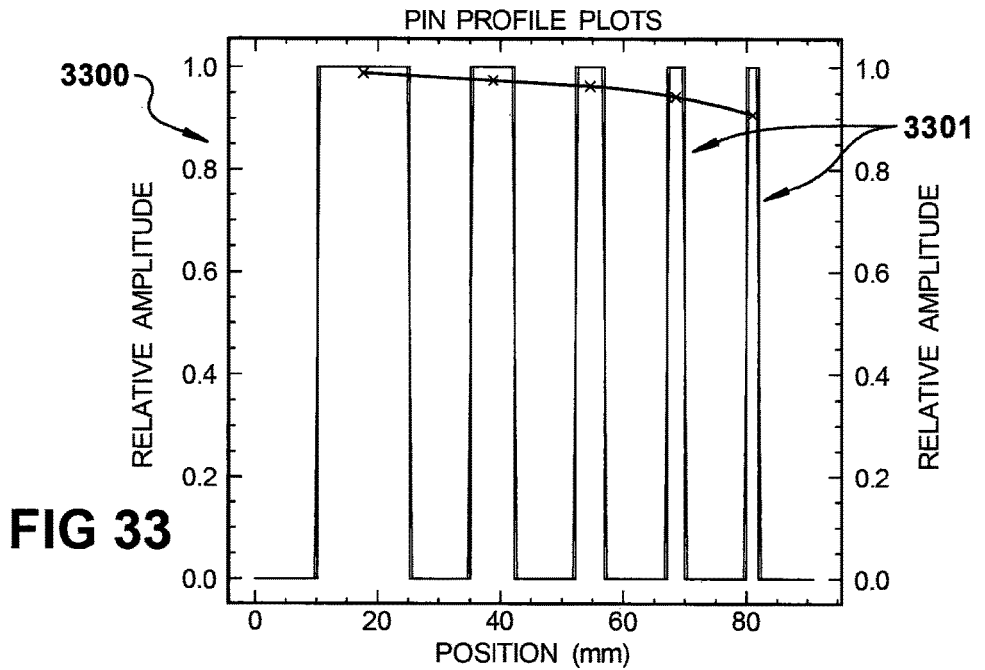
GRAY: ORIGINAL PIN, BLUE: RECONSTRUCTED PIN, RED: INTREGAL INSIDE PIN REGION
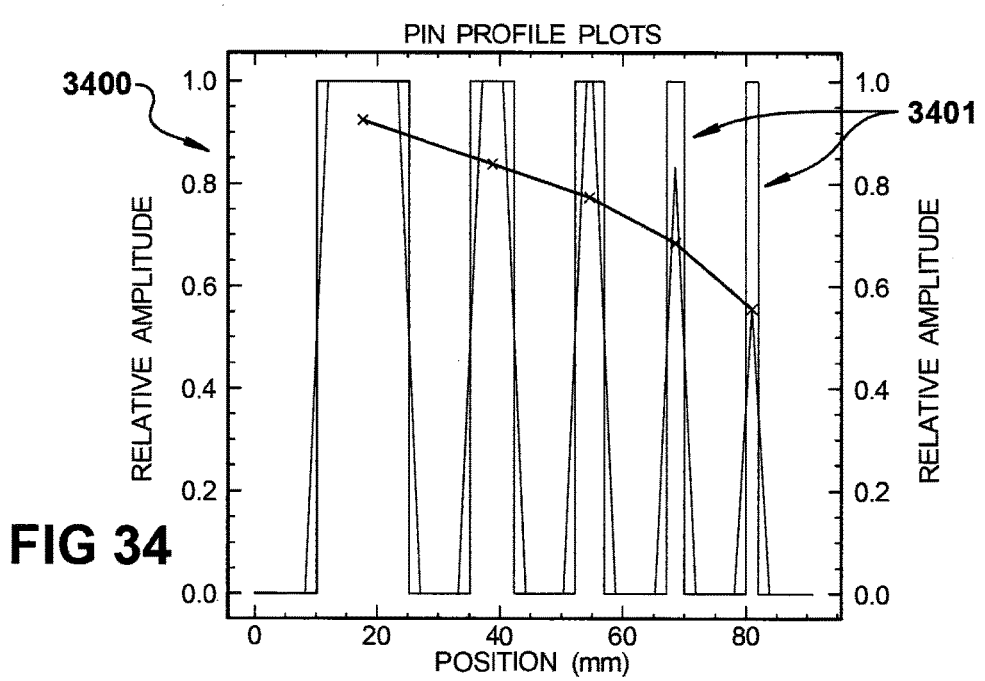
GRAY: ORIGINAL PIN, BLUE: RECONSTRUCTED PIN, RED: INTREGAL INSIDE PIN REGION
ILLUSTRATION OF CONTRAST REDUCTION DUE TO PIN BLURRING. TOP: BLURRING IN A
HEAD SCAN PROTOCOL. BOTTOM: BLURRING IN A BODY SCAN PROTOCOL.

UPPER: LARGE PIN CONTRAST PERFORMANCE CURVE (pins > 2.5mm).
LOWER: SMALL PIN CONTRAST PERFORMANCE CURVE (red=2.5mm, green=2mm)

ALTERNATIVE PRESENTATIONS OF SNR vs FLUXINDEX INFORMATION SINCE FLUXINDEX IS A FUNCTION OF Dw AND mAs IS PROPORTIONAL TO CTDIvol $$\text{FluxIndex} = \text{mAs} \times \text{slice} \times \frac{e^{-D_w \times \mu_{water}}}{e^{-\text{Diam}_{ref} \times \mu_{water}}}$$

4602 —

SNR vs mAS @ specified Dw
SNR vs CTDIvol @ specified Dw
Contrast Index vs mAs @ specified Dw
Contrast Index vs CTDIvol @ specified Dw
CTDIvol vs Dw @ specified SNR
mAs vs Dw @ specified SNR

4604

SNR vs Dw @ specified mAs
SNR vs Dw @ specified CTDIvol
SNR vs Dw @ specified mAs
SNR vs Dw @ specified CTDIvol

FIG 46

PIN SIZES: 2.0, 2.5, 3.3, 4.3, 5.5, 7.0, 9.0, 11.7, 15.0

"X" POINTS INDICATE DETECTABILITY VALUES FOR EACH OBJECT SIZE FOR A GIVEN CONTRAST LEVEL. THE THICK LINE SHOWS A LINEAR FIT OF DETECTABILITY VALUES. LOCATION "A" INDICATES THE SMALLEST OBJECT SIZE BASED ON THE SMALLEST DISTINCT OBJECT ABOVE THE THRESHOLD. LOCATION "B" INDICATES THE SMALLEST OBJECT SIZE BASED ON A FIT USING ALL OBJECT SIZES.

METHODS AND APPARATUS FOR EXTENDED LOW CONTRAST DETECTABILITY FOR RADIOGRAPHIC IMAGING SYSTEMS

CROSS-REFERENCE TO RELATED APPLICATIONS

This application claims priority to U.S. patent application Ser. No. 13/503,721, issued as U.S. Pat. No. 8,891,849 issued on Nov. 18, 2014 entitled "Methods and Apparatus for Extended Low Contrast Detectability for Radiographic Imaging Systems" by David P. Rohler et al., and filed Apr. 24, 2012, which itself claims priority to PCT Patent Application No. PCT/US2010/002006, filed Jul. 16, 2010 and which claims the benefits of U.S. Provisional Patent Application No. 61/271,150 filed Jul. 17, 2009 and U.S. Provisional Patent Application No. 61/278,954, filed on Oct. 14, 2009, all of which are hereby fully incorporated by reference. This application further claims priority to U.S. patent application Ser. No. 13/837,448, filed on Mar. 15, 2013.

BACKGROUND OF THE INVENTION

This invention relates generally to medical radiology and more particularly to methods and apparatus for radiographic imaging.

Radiographic imaging of all kinds, including computed tomography (CT) imaging, can detect small low contrast features. Thus, radiographic imaging has become important in medical practice, allowing medical practitioners to detect low contrast tumors and lesions in anatomical regions of soft tissue, including the brain and the liver. An important issue in radiology today concerns the reduction of radiation dose received by a patient during a CT examination without compromising image quality. Generally, higher radiation doses result in the ability to detect lower contrast smaller objects, while lower doses lead to increased image noise. Higher radiation doses also increase the risk of radiation-induced cancer. Thus, the ability to image low contrast objects at a low dose is desirable for diagnostic x-ray imaging methods.

The ability of a CT system to differentiate a low-contrast object from its background is measured by its low contrast detectability (LCD). Low contrast detectability is measured using phantoms that contain low-contrast objects of various sizes. Phantoms that produce low contrast objects by using materials with different densities are useful for testing conventional energy integrating CT scanners. Phantoms that produce low contrast objects using energy sensitive materials allow performance testing for a dual energy scanner.

The low-contrast resolution of a CT scanner is generally defined as the diameter of an object that is just detectable at a given contrast level and dose. The contrast level is usually specified as a percentage of the linear attenuation coefficient of water. A sample specification with the current method might be "4 mm at 0.3% contrast for 10 mm slice thickness at 30 mGy CTDIvol dose." Sometimes other dose metrics are used, such as the surface dose measured at the outer surface of the phantom or the Size Specific Dose Estimate {AAPM 2011}.

At least two LCD specifications are known. One known LCD specification is made at a single protocol using human observation. In this method, reconstructed images are viewed by one or more human observers to determine the smallest pin that, in the opinion of the observer, is visible. Another known LCD specification is made at a single protocol using a statistical method. In this method, an automated algorithm predicts the contrast required to detect a given size pin with a specified confidence interval from a flat "water" image.

These known LCD specifications characterize the performance of the CT scanner at only one protocol and one phantom size. Furthermore, the known LCD specifications do not characterize the performance of a CT scanner over an extended range. For example, only a portion of the full operating range of the scanner is characterized. It would therefore be desirable to provide methods and apparatus for characterizing the performance of a radiometric imaging apparatus such as a CT scanner at more than one protocol, over the full operating range of the imaging apparatus, or both.

Flux Index

At least some known commercial CT scanners operate over a wide range of protocols, each of which can have distinct contrast characteristics. The protocol parameters that affect contrast include scan time, tube current (mA), slice thickness, object diameter, tube voltage (kVp) and x-ray filter. Contrast is also significantly affected by non-linear reconstruction methods as well as the reconstruction pixel size and reconstruction filter. It is assumed herein that the tube voltage, the x-ray filter, the scan diameter and the reconstruction method, collectively comprising a core operating mode, are fixed and that the scanner, in that core operating mode, can be characterized by the CTDIvol dose index. Then the parameters (example values of which are given in parentheses) that directly affect the x-ray flux available for detection comprise scan time (0.25-2.0 sec/revolution), x-ray tube current (20-400 mA), slice thickness (0.5-10.0 mm), object diameter (20-50 cm), and dose index (CTDIvol)

At least one known LCD method uses a CTP515 low contrast module of the CATPHAN® phantom, available from Phantom Laboratory, Inc., Salem, N.Y. "Supra-slice" contrast sets are used but only the lowest 0.3% contrast set is typically reported.

There are at least two LCD measurement methods known to be used on commercial CT scanners. These methods are named the "human observer method" and the "statistical method." We have compiled some recent reported measurements from the major CT manufacturers and collected them in Table 1. [NHS Purchasing and Supply Agency, Buyer's Guide, Computed Tomography Scanners, Reports CEP08007, CEP08027, CEP08028].

TABLE 1

Recent Reported LCD Measurements from Major CT Manufacturers
Source: NHS Purchasing and Supply Agency, Buyer's Guide, CT Scanners

| Contrast Index | Scanner | Contrast | Pin Size | Dose | Slice Thickness | mAs | Ref. Num. on FIG. 1 | Flux Index |
|---|---|---|---|---|---|---|---|---|
| 500 | A | 0.3% | 4 mm | 10 mGy | 10 mm | 90 | 12 | 900 |
| 400 | B | 0.3% | 5 mm | 16 mGy | 10 mm | 180 | 14 | 1440 |

TABLE 1-continued

Recent Reported LCD Measurements from Major CT Manufacturers
Source: NHS Purchasing and Supply Agency, Buyer's Guide, CT Scanners

| Contrast Index | Scanner | Contrast | Pin Size | Dose | Slice Thickness | mAs | Ref. Num. on FIG. 1 | Flux Index |
|---|---|---|---|---|---|---|---|---|
| 1000 | C | 0.3% | 2 mm | 40 mGy | 10 mm | 350 | 16 | 3600 |
| 400 | D | 0.3% | 5 mm | 7.3 mGy | 10 mm | 105 | 18 | 657 |

These reported measurements show performance at only one point on the operating curve and that the operating point is different for each scanner, making performance comparisons invalid. This is shown as Prior Art FIG. 1 (based on it being based on previously reported measurements, not on it being presented on an ExLCD graph) on an ExLCD graph 10 based on definitions of ExLCD Contrast Index and Flux Index described elsewhere herein.

Human Observer Method

In the Human Observer Method, LCD is determined by scanning a CATPHAN® phantom under selected protocol techniques and reconstructing the image or images of phantom. One or more human observers are then presented with the image or images of the phantom to render an opinion regarding the smallest object they believe is visible and therefore detectable for the 0.3% contrast set. For the reported measurements described above, it is not clear to the inventors whether a single observer or multiple observers were used. It is also not clear to the inventors how the specific protocol was selected to derive the reported specification.

Statistical Method

The statistical method for LCD avoids problems associated with human observers by relying only on noise measurements in a reconstruction. It does not use a phantom with actual contrast objects. Instead, it analyzes image noise in a specific manner that determines the amount of contrast needed to detect an object of a given diameter relative to the background with a stated level of confidence. Because the assessment is made by the computer and not a human observer, the method is repeatable and reproducible. However, the statistical method cannot differentiate contrast performance resulting from non-linear reconstruction methods since only a noise image is evaluated. The performance of the system relative to how well the original low contrast object is preserved thus cannot be determined, as is true of any noise analysis method that does not measure an actual object.

Quantum Noise Limited

An imaging system is said to be "quantum noise limited" if, for all practical purposes, the only source of image noise is the statistics of finite x-ray quanta and electronic noise is absent. Referring to graph 20 of prior art FIG. 2, the S/N (signal to noise) ratio is plotted as a function of relative x-ray Flux Index. In a log-log plot, the S/N ratio trace 22 for a quantum noise limited system is represented by a straight line having a slope of ½. If electronic noise (also known as "system noise") is present, the overall S/N is significantly affected only for lower flux values as shown by trace 24 in FIG. 2.

With at least one LCD method known by the inventors to be in current use, a scanner is characterized with only one contrast measurement taken at a single protocol. This single measurement does not adequately characterize the contrast performance of the scanner. The single protocol measurement implies a contrast performance that follows a quantum noise limited curve defined by the single measurement. There is thus an inadequacy of the single protocol contrast performance curve. Additionally, this known LCD method does not adequately handle smaller pins that are affected by system blurring, i.e. the Modulation Transfer Function (MTF).

At least some known detectability methods that are based only on a noise analysis (such as the statistical method, noise power spectrum, simple-pixel standard deviation, and matched filter standard deviation) can overestimate the performance of a reconstruction process that alters the contrast of the test object. These known detectability methods use reconstruction processes that limit spatial bandwidth of both noise and object and do not account for changes in the assumed object. For example, assume that a small pin in an LCD test phantom is a cylinder with a 2 mm diameter and a contrast of 0.3%. If perfectly reconstructed, image pixels within the area of the pin have an average contrast of 0.3% and all pixels outside this region have an average contrast of 0%. However, the MTF of the system will blur the pin (especially at its edges) and spread some of its contrast into pixels beyond the original geometric boundary, resulting in a reduction in average contrast within the pin region.

Thus, it will be understood that inaccuracies of at least some known single protocol LCD methods result from human observer variation, finite pin size selections, selection of protocol, presence of system (electronic) noise; and/or system blurring (MTF) of smaller pins The low contrast detectability (LCD) performance of a CT system is a critical performance characteristic, providing a measure of the ability of a scanner to produce high quality images at a low x-ray dose such as the lowest possible x-ray dose. Because the use of lower dose protocols in CT scanners is now of considerable importance, it is correspondingly desirable for LCD to be measurable over a wide range of protocols and body sizes. However, inaccuracies of the known prior art effectively prevent true differentiation of the contrast performance between CT scanners.

Automatic Exposure Control (AEC) systems for radiographic imaging systems such as CT are known to be in widespread clinical use. An objective of these systems is to reduce patient dose by allowing the CT system to determine and modulate an mA along a patient's Z axis as necessary to achieve a desired Clinical Image Quality (CIQ). A user determines or selects a CIQ necessary or desirable for the clinical application in terms of an Image Quality Metric (IQM) goal parameter provided by the CT vendor and the CT system is designed to produce the appropriate x-ray dose to achieve it. XY or angular modulation is also provided in at least some known CT systems, but AEC as used herein refers to Z axis modulation.

An important consideration for an AEC system is how the user specifies a desired CIQ. Depending upon the CT vendor, some known CT systems use a variety of IQMs.

These methods include specifying a reference mA based on an nominal patient size chosen by the vendor, an image standard deviation, a noise index, or a reference image. However, methods known by the inventor to be in current use do not adequately describe CIQ, are not universal (i.e., the same values cannot be used on other make and model scanners), and may not track the desired CIQ with patient size. In addition, the use of different methods to determine an IQM increases confusion among technologists, increasing the likelihood of medical errors as well as making it more difficult to compare IQ and dose tradeoffs for different features and systems.

Size and contrast of an object, such as a lesion, that can be successfully identified with adequate sensitivity and specificity depend on many factors {Barrett 2004}. Object detectability is a significant component of clinical image quality and is related to dose applied and the image generation method used. It is well known that objects are more difficult to successfully identify as noise increases. Image noise is characterized as a mottle of pixel variations without any apparent consistent structure. CT image noise results from x-ray quanta as well as non-quantum sources. X-ray quantum noise is statistical photon noise that decreases inversely with the square root of the X-ray intensity, which in turn is proportional to the mA selection. Non-quantum noise includes electronic and electromagnetic sources and generally becomes a noticeable factor only at low x-ray flux levels with large patients. However, noise alone does not determine detectability, which is also influenced by how well an image generation system reproduces a scanned object within an image. The reproduction of the object is especially important when evaluating adaptive and model-based iterative image generation methods. Thus, an IQM based on detectability is better able to universally describe patient CIQ goals. The IQM goal metrics used by at least some known CT AEC systems are not universal.

SUMMARY OF THE INVENTION

In one aspect, some embodiments of the present invention therefore provide a method for a method for evaluating dose performance of a radiographic imaging system with respect to image quality using a phantom, a channelized hotelling observer module as a model observer, and a printer, a plaque, or an electronic display. The method includes scanning and producing images for a plurality of sections of the phantom using the radiographic imaging system, wherein the plurality of sections represent a range of patient sizes and doses and wherein the sections of the phantom contain objects of measurable detectability. Also included is analyzing the images to determine detectability results for one or more of the contained objects within the images of the plurality of sections of the phantom, wherein the analyzing includes using a channelized hotelling observer (CHO) module as a model observer; and displaying, via the printer, the plaque, or the electronic display, a continuous detectability performance measurement function using the determined detectability results.

In another aspect, some embodiments of the present invention provide a phantom for use with radiographic imaging systems. The phantom has one or more sections, wherein each of the sections further includes a plurality of cross-sectional areas that have: a region having objects to be detected by the radiographic imaging system; a background region with no objects; and regions having densities matching objects to be detected and that are sufficiently large so as to enable the measurement of effective contrasts of the objects to be detected.

In yet another aspect, some embodiments of the present invention provide a method for setting a protocol for imaging a patient using a computerized radiographic imaging device. The method includes imaging a phantom containing a plurality of objects using a plurality of flux settings within an operating range for at least one operating protocol of the computerized radiographic imaging device to obtain projection data. The method also includes reconstructing the projection data into a plurality of reconstructed images of the phantom corresponding to the plurality of flux settings using the radiographic imaging apparatus. Also, for each of the flux settings, the method includes, with the computerized radiographic imaging apparatus: automatically calculating a detectability of the objects in a reconstructed image corresponding to the flux setting; selecting the automatically calculated detectable objects in accordance with a detectability criterion; determining a contrast measure for the selected objects; and associating a contrast performance with the flux setting of the image in accordance with the determined contrast measures. The method further includes imaging the patient with the computerized radiometric imaging device using a radiation dose in accordance with the associated contrast performance and flux settings to produce an image of the patient having a desired image quality.

In yet another aspect, some embodiments of the present invention include a method of determining an extended low contrast detectability performance measurement function as a relation between a Flux Index and a Contrast Index for an operating range for a core operating mode of a radiographic imaging system using actual reconstructed images. This method includes selecting a plurality of protocols distributed across the operating range of the radiographic imaging system and imaging a phantom containing a plurality of objects over each of the protocols. The method further includes computing a detectability for each object in order to determine an ordered pair of Flux Index and Contrast Index for each object and determining a smallest detectable object size for each contrast set. Also included in the method is computing the Contrast Index for each protocol for each contrast set; and utilizing the ordered pairs of Flux Index and Contrast Index to determine the extended low contrast detectability performance measurement function for the radiographic imaging system.

These and other aspects of the disclosure and related inventions are further described herein with reference to the accompanying Figures.

It will be appreciated that some embodiments of the present invention provide at least one or more desirable features, among which may include characterization of the performance of a radiometric imaging apparatus such as a CT scanner at more than one protocol, over a full operating range of the imaging apparatus, or both. Also included may be the adequate handling of smaller pins that are affected by system blurring and/or remedying of the inadequacy of a single protocol contrast performance curve. Also included may be the remedying of inaccuracies that prevent true differentiation of contrast performance between different CT scanners, an adequate description of CIQ, a universal description of CIQ, and the tracking of desired CIQ with patient size. In addition, some advantages that may be realized include less confusion among technologists, and a better way to determine detectability in radiometric imaging systems.

BRIEF DESCRIPTION OF THE DRAWINGS

FIG. 9 is a graph illustrating the standardization of clinical protocols between two or more scanners.

FIG. 10 is a schematic representation of a patient image.

FIG. 11 is a schematic representation of projection data obtained from a patient.

FIG. 29 is a schematic illustration of a matched filter detectability analysis method.

FIG. 33 is a graph showing contrast reduction due to pin blurring in a head scan protocol.

FIG. 34 is a graph showing pin blurring in a body scan protocol.

FIG. 46 is a representation of alternate presentations of SNR vs. FluxIndex information in various embodiments.

Figure 1:
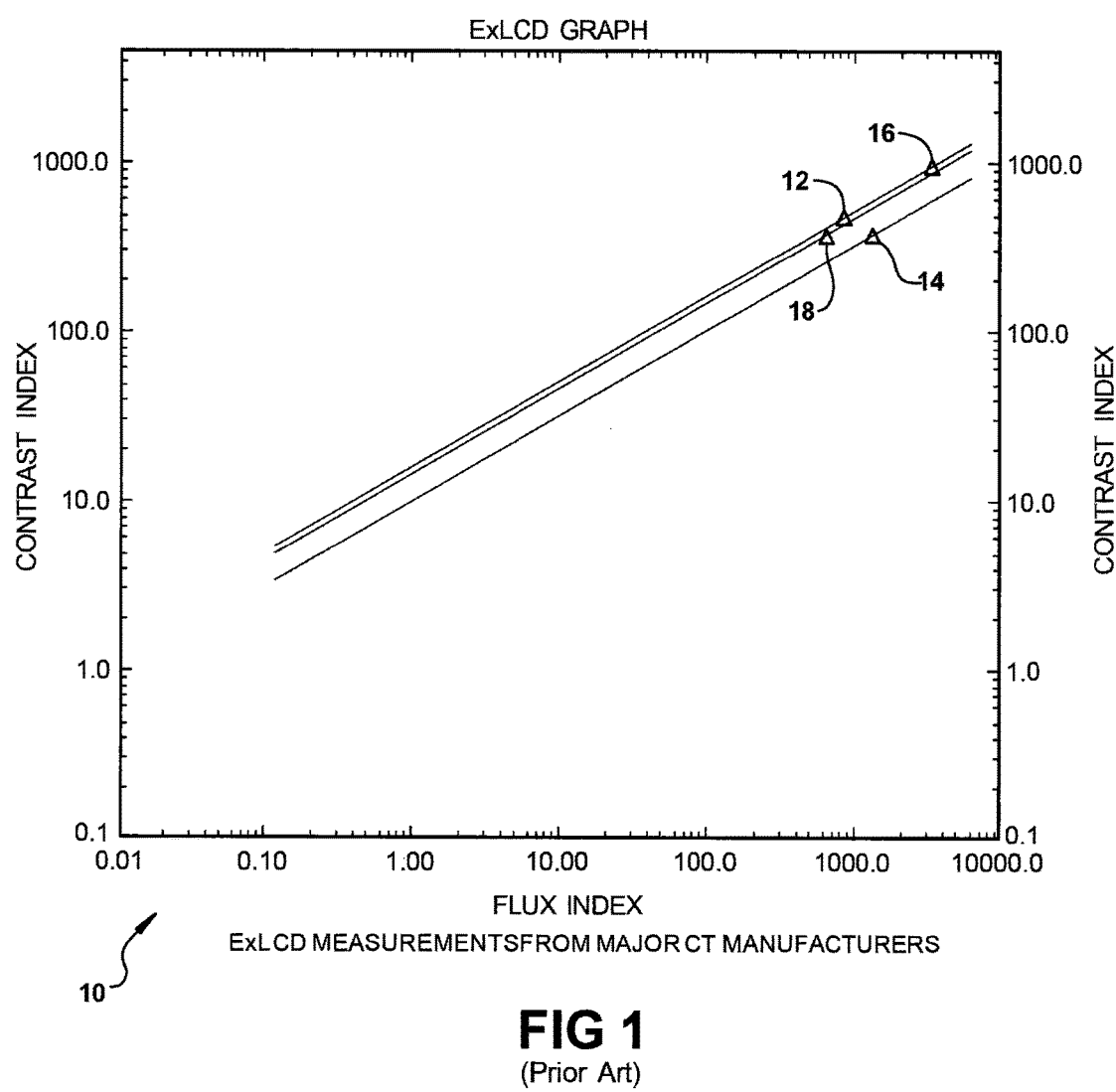
FIG. 1 is a prior art graph of measurements from major CT manufacturers.
Figure 2:
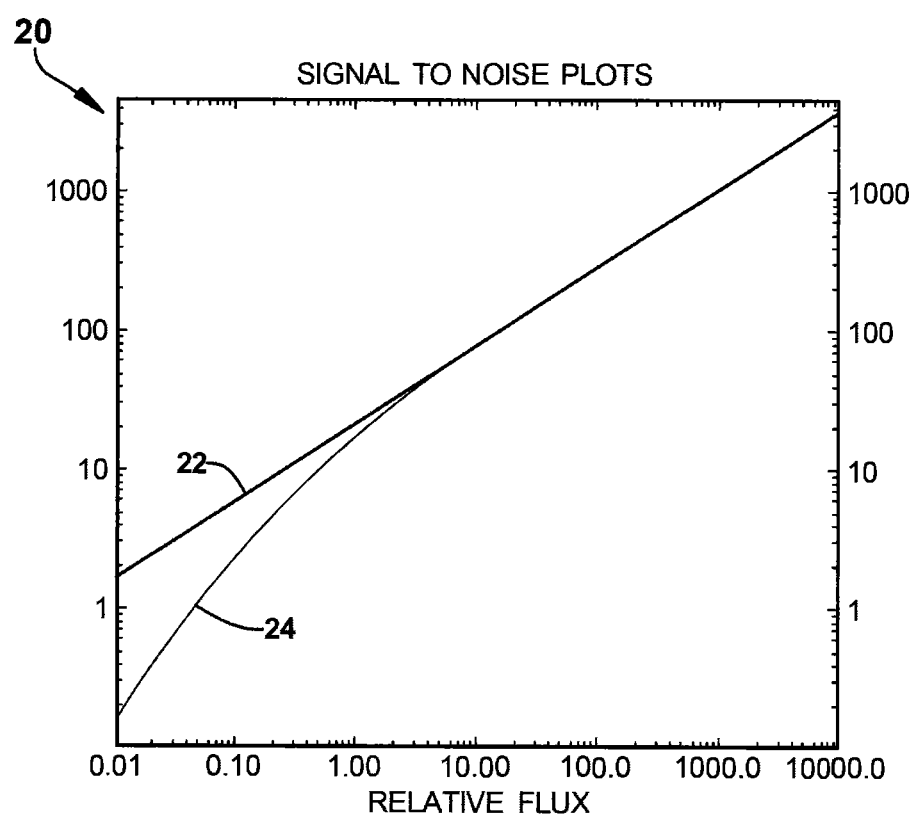
FIG. 2 is a graph of a prior art signal-to-noise ratio plotted as a function of relative x-ray Flux Index.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry.

DETAILED DESCRIPTION OF THE INVENTION

As used herein, an element or step recited in the singular and proceeded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

The embodiments recited herein are described in the context of computed tomography (CT) applications, but the inventive technology described herein is not limited to CT and can be applied to other radiographic imaging systems as well. Thus, the use of the terms "CT" and "CT scanner" should be interpreted as also encompassing other radiographic imaging systems, unless otherwise stated.

As referred to herein, a "radiographic imaging system" is an imaging system that uses electromagnetic radiation (x-ray, gamma ray, etc.) for building an image. For example, the radiographic imaging system uses electromagnetic radiation of such short wavelength that it is able to produce an image showing internal structures of an object, such as organs in a patient's body. Examples of radiographic imaging systems suitable for use in or in conjunction with embodiments of the present invention include but are not limited to CT scanners, digital radiographic devices, mammography devices, nuclear imaging devices, and SPECT devices.

Unless otherwise indicated, the contrast measurements discussed herein are indicative of contrast at the center of an object such as a patient. For that reason, the descriptions of ExLCD methods herein are based on the relative flux index.

Technical results of various configurations and embodiments of the present invention include one or more of the following: characterization of the performance of a radiometric imaging apparatus such as a CT scanner at more than one protocol, over a full operating range of the imaging apparatus, or both; the adequate handling of smaller pins that are affected by system blurring and/or remedying of the inadequacy of a single protocol contrast performance curve; the remedying of inaccuracies that prevent true differentiation of contrast performance between different CT scanners, an adequate description of CIQ, a universal description of CIQ, and the tracking of desired CIQ with patient size; less confusion among technologists, and a better method and apparatus to determine detectability in radiometric imaging systems.

"ExLCD" is a method for generating a continuous image quality function (Contrast Index vs. Flux Index) that provides a metric to relate the detectability in radiological images of small low contrast objects to the technique used when acquiring the images. ExLCD provides an image quality metric (IQM) used in some embodiments to guide clinical practice regarding appropriate clinical image quality (CIQ) and associated dose utilization on a radiological imaging device (scanner), or more universally, on a plurality of such devices. ExLCD also allows the quantification of image quality and dose performance for different scanners or operating modes to be compared on a common scale over the performance range continuum.

Figure 3:
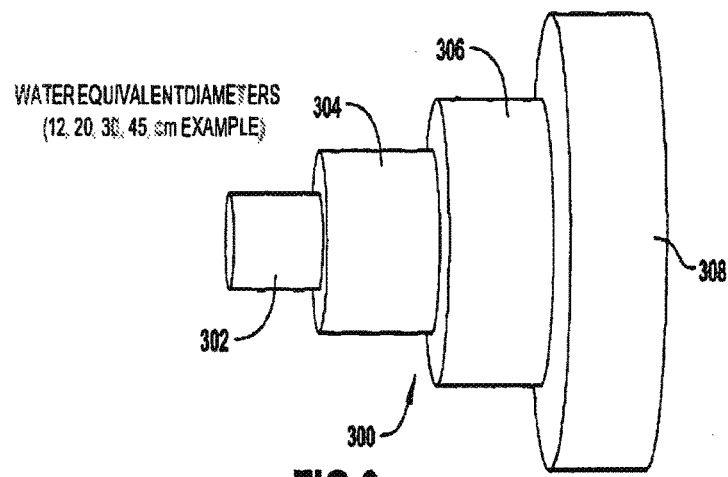
FIG. 3 is a shaded 3-D drawing of a phantom embodiment.
Figure 4:
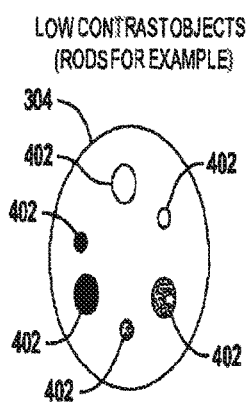
FIG. 4 is a cross sectional view through a section of the phantom shown in FIG. 3 showing low contrast objects embedded therein.
Figure 5:
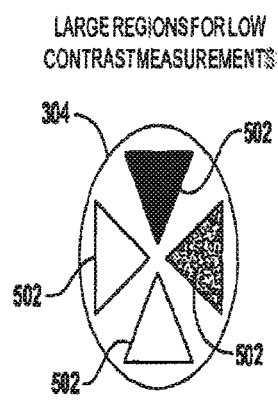
FIG. 5 is a cross sectional view through a section of the phantom shown in FIG. 3 showing large regions for low contrast measurements.
Figure 6:
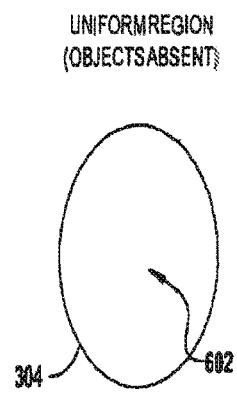
FIG. 6 is a cross sectional view through a section of the phantom shown in FIG. 3 showing a uniform region in which objects are absent.

In at least one embodiment and referring now to FIG. 3, ExLCD uses images produced by scanning a phantom such as specially designed phantom 300 to measure scanner performance. Phantom 300, for example, comprises a plurality of sections 302, 304, 306, 308 that have diameters representing a range of patient sizes. Referring now to FIG. 4, each section of a given diameter, for example, section 304, contains small low contrast objects 402 (such as rods) of various sizes and contrast levels. In some embodiments and referring to FIG. 5, sections such as section 304 contain large regions 502 for low contrast measurements. Also, in some embodiments and referring to FIG. 6, sections such as section 304 contain a uniform region 602 in which objects 402 are absent. To characterize a scanner, phantom 300 is scanned over a range of Flux Index settings and the resulting data is reconstructed to produce a plurality of images. A detectability module analyzes low contrast objects in the images to measure detectability to produce an Image Quality (IQM) function called Contrast Index as shown in graph 700 of FIG. 7.

In one embodiment, the ContrastIndex value is written $$ContrastIndex = \frac{6000}{pinSize \times Contrast} \quad (1)$$

and is a set of measurements of a smallest detectable pin 402 at each contrast value 702. The value of FluxIndex is written:

$$FluxIndex = mAs \times slice \times \frac{e^{-Diam \times \mu_{water}}}{e^{-Diam_{ref} \times \mu_{water}}}. \quad (2)$$

(Note: Diam is also written as $D_{weq}$.)

Figure 7:
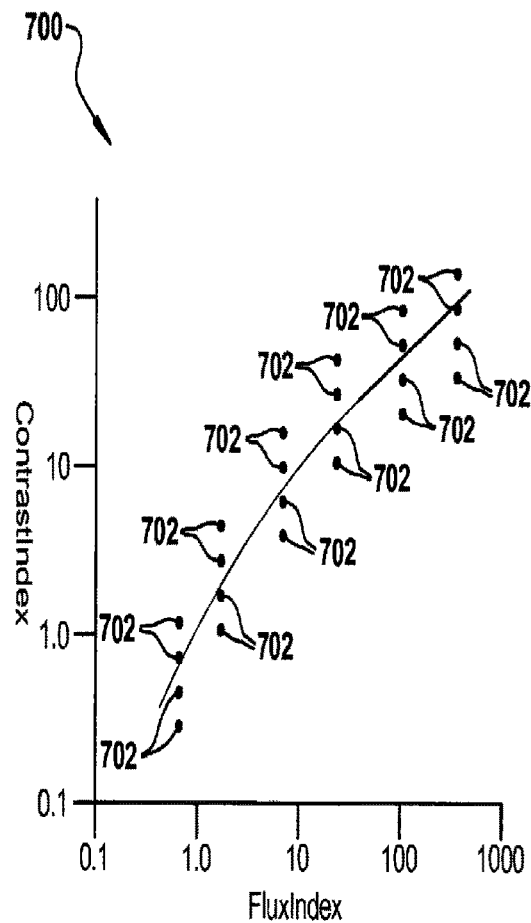
FIG. 7 is a example graph of an Image Quality (IQM) function called Contrast Index.

Trace 700 in FIG. 7 is the result of a regression model fitting Contrast Index as a function of Flux Index.

Figure 8:
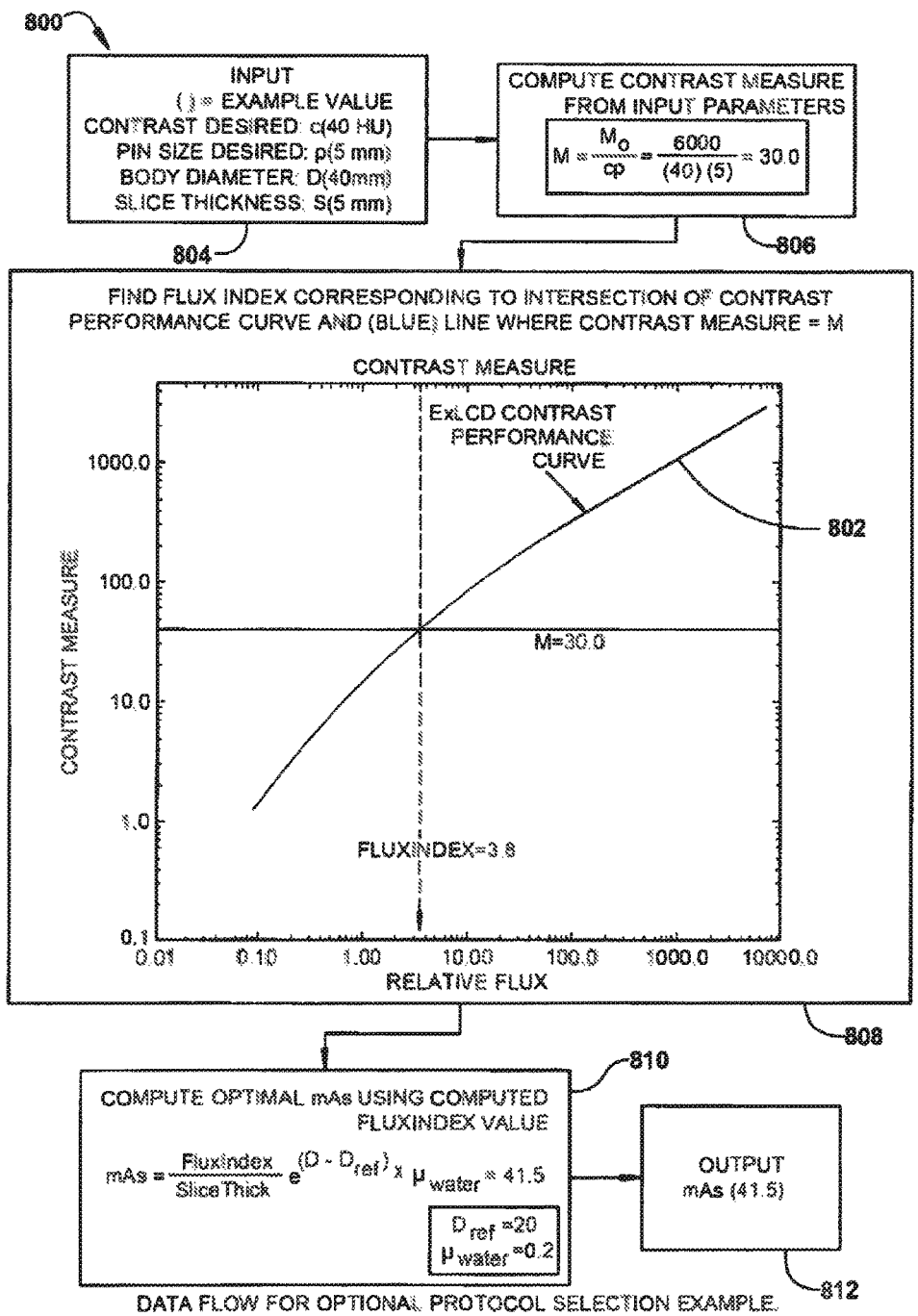
FIG. 8 is a drawing of a representative data flow for a process embodiment for protocol selection using an ExLCD Performance Function.

Referring now to FIG. 8, a representative data flow 800 is shown for a process embodiment for protocol selection using an ExLCD Performance Function 802. ExLCD Performance Function 802 is provided for a particular CT scanner (or, more generally, a particular radiographic imaging system). A radiologist (or other operator or responsible party) at block 804 selects a desired contrast level in accordance with clinical image quality (CIQ) requirements. (In FIG. 8, the term Contrast Measure is synonymous with Contrast Index.) In this example, the desired Contrast Index is computed at block 806 from the input parameters, written:

$$M = \frac{M_0}{cp} = \frac{6000}{(40)(5)} = 30.0 \quad (3)$$

corresponding to a 5 mm pin at a contrast level of 40 Hounsfeld Units (HU). A Protocol Selection module at block 808 then determines a Flux Index value on or near an ExLCD Performance Function 802 corresponding to the desired Contrast Index. Since the ExLCD Performance Function 802 is always monotonic, there will be a unique optimum Flux Index value corresponding to the intersection of the Contrast Index value and the ExLCD Performance Function 802. For this example, the Flux Index value determined is 3.8. This unique Flux Index value is used in this embodiment to determine the optimal protocol at block 810, which, in this embodiment, uses the relationship written $$mAs = \frac{FluxIndex}{SliceThick} e^{(D-D_{ref}) \times \mu_{water}} = 41.5 \quad (4)$$

where $D_{ref}=20$ and $\mu_{water}=0.2$. The mAs is then output or sent to a scanner to perform the procedure at block 812.

(Although not explicitly stated for each embodiment and configuration disclosed herein, embodiments in which approximations are used to approach an optimum protocol or to at least reduce or otherwise optimize radiation dosage are also useful and are considered by the inventors to fall within the scope of the present invention.)

In at least one embodiment of the present invention, slice thickness is selected as an independent parameter and a method for determining the patient body diameter D is used. A method suitable for such use is a prior art method described below for determining the patient water equivalent diameter ($D_{weq}$). For the example illustrated in FIG. 8, the patient diameter is 40 cm and the slice thickness is 5 mm, resulting in the determination of mAs=41.5 as the optimal flux for the desired image quality.

In some embodiments and referring to graph 900 of FIG. 9, clinical protocols are standardized between two or more scanners. Assuming that the "red scanner" is the baseline scanner for which protocols have been developed, this method determines corresponding clinical protocols for the "blue scanner." The method includes steps of, for each desired protocol on the red scanner, (a) determining, at block 902, a corresponding Flux Index for the red scanner protocol, (b) looking up, at block 904, a corresponding Contrast Index on the red scanner's ExLCD Performance Function, (c) finding, at block 906, an equivalent Contrast Index value on a blue scanner's ExLCD Performance Function, and (d) looking up, at block 908, a corresponding FluxIndex in accordance with on the blue scanner's ExLCD Performance Function, thus determining an equivalent clinical protocol for the blue scanner.

Patient Water Equivalent Diameter

Referring now to FIGS. 10 and 11, the overall attenuation of a scanned object, such as patient 1100, can be determined from a CT image 1000 from projections 1102 in terms of a water equivalent area. The summation of I(x, y) is the water equivalent area, where I(x, y) is obtained from image pixels of the CT image, converted to an area weighted by the relative attenuation of the pixels. The square root of the water equivalent area is defined as Attenuation Units (AU).

$$D_{weq}=2\times\sqrt{\Sigma I(x,y)/\pi} \quad (5)$$

and $$I(x,y)=(\text{image}(x,y)/100+1)\times\text{PixelArea} \quad (6)$$

Water equivalent diameter can also be estimated from a scan projection radiograph using the projection area and an appropriate scanner dependent conversion factor, for example, 0.557, for a commercially available multi-slice scanner.

$$D_{weq}=2\times 0.557\times\sqrt{\Sigma P(i)/\pi} \quad (7)$$

In some embodiments of the present invention, patient information is obtained using boundaries of a body shown in a radiograph. In some configurations of this embodiment, Body Mass Index along with body diameter are used to optimize protocols. The value for mAs (milliAmpere-seconds) of dose is then written:

$$mAs = \frac{FluxIndex}{sliceThick}e^{(D_{weq}-D_{ref})\times\mu_{water}} \quad (8)$$

where $D_{weq}$ is the effective water equivalent object diameter, and $D_{ref}$ is the effective water equivalent diameter of a reference object. Knowing the Flux Index, since the patient diameter $D_{weq}$ is known along with the slice thickness sliceThick, a required mAs for the scan is thus determined to achieve the desired CIQ for the patient. (As will be understood by those skilled in the art, a "required" mAs value need not be exact, but actually encompasses a range of values within engineering and medical tolerances that produce essentially similar results. Therefore, when a single "optimum" or "required" value is recited hereinafter, it will be understood to encompass not only the optimum or required value stated, but also a range of values within these tolerances unless explicitly stated otherwise.)

In some embodiments, both the object diameter and $\mu_{water}$ are determined using a water beam hardening corrected mean amplitude (e.g., mean of the highest 50 samples) of scan projection radiograph from an orientation with the longest path length (usually the lateral direction). Because image noise is generally most influenced by the noisiest projections, these embodiments can provide more consistent contrast performance than those using $D_{weq}$ determined from the water equivalent area.

In some embodiments of the present invention, a particular scanner has more than one ExLCD Performance Function. For example, a scanner may have an ExLCD Performance Function for each of:
1. Slice thickness;
2. X-ray beam energy (including dual energy);
3. Choice of reconstruction method (examples of such choices include filter choice and degrees of inclusions of non-linear reconstruction algorithms); and
4. Selection of compensator.

Therefore, some embodiments use a plurality of ExLCD Performance Functions dependent upon the protocol parameters that are provided as input.

Some embodiments of the present invention provide a method for determining a desired Contrast Index in a clinical setting. For example, one embodiment accepts as input a specification of a desired object contrast differentiation in Hounsfield units and an object size.

Also, in some embodiments, a desired Contrast Index is derived using actual clinical images in a clinical setting. For example, clinical images from various patients at various dose levels for a particular clinical task on an ExLCD calibrated scanner are qualitatively graded by radiologists for acceptability. ExLCD is then used to determine the contrast index for each patient image. In this way, clinical opinions are associated with the ExLCD performance relationship, and in particular, this association relates the IQM to CIQ. A sufficient number of qualitative radiologist studies regarding clinical acceptability is used to determine an appropriate contrast index to use in clinical practice. The use of an ExLCD performance relationship provides the ability to reproduce required results for any patient on any calibrated scanner.

It is advantageous from the standpoint of possible patient side effects to use the smallest possible concentration of contrast media, however, it is also important to use enough contrast so that the desired CIQ can be achieved. The use of ExLCD performance relationships in some embodiments is thus expanded to optimize a concentration of contrast media used for a radiographic imaging system.

In some embodiments, to track contrast performance that is affected by non-linear or iterative reconstruction, the reconstructed object contrast is measured. Using measured contrast, a reconstruction process embodiment with a highly filtered noise spectrum causes object smoothing that results in a lower ExLCD Contrast Index than a reconstruction process that is able to filter the noise while retaining the spatial geometry of the original object.

In some embodiments of methods using ExLCD technology, at least four components are used:
(a) an ExLCD phantom 300 containing various contrast/diameter cross-sections;
(b) a set of scan protocols and image slices used for ExLCD measurement;
(c) a detectability determination module; and
(d) a Contrast Index function generator and parameter calculation module or modules.

Figure 12:
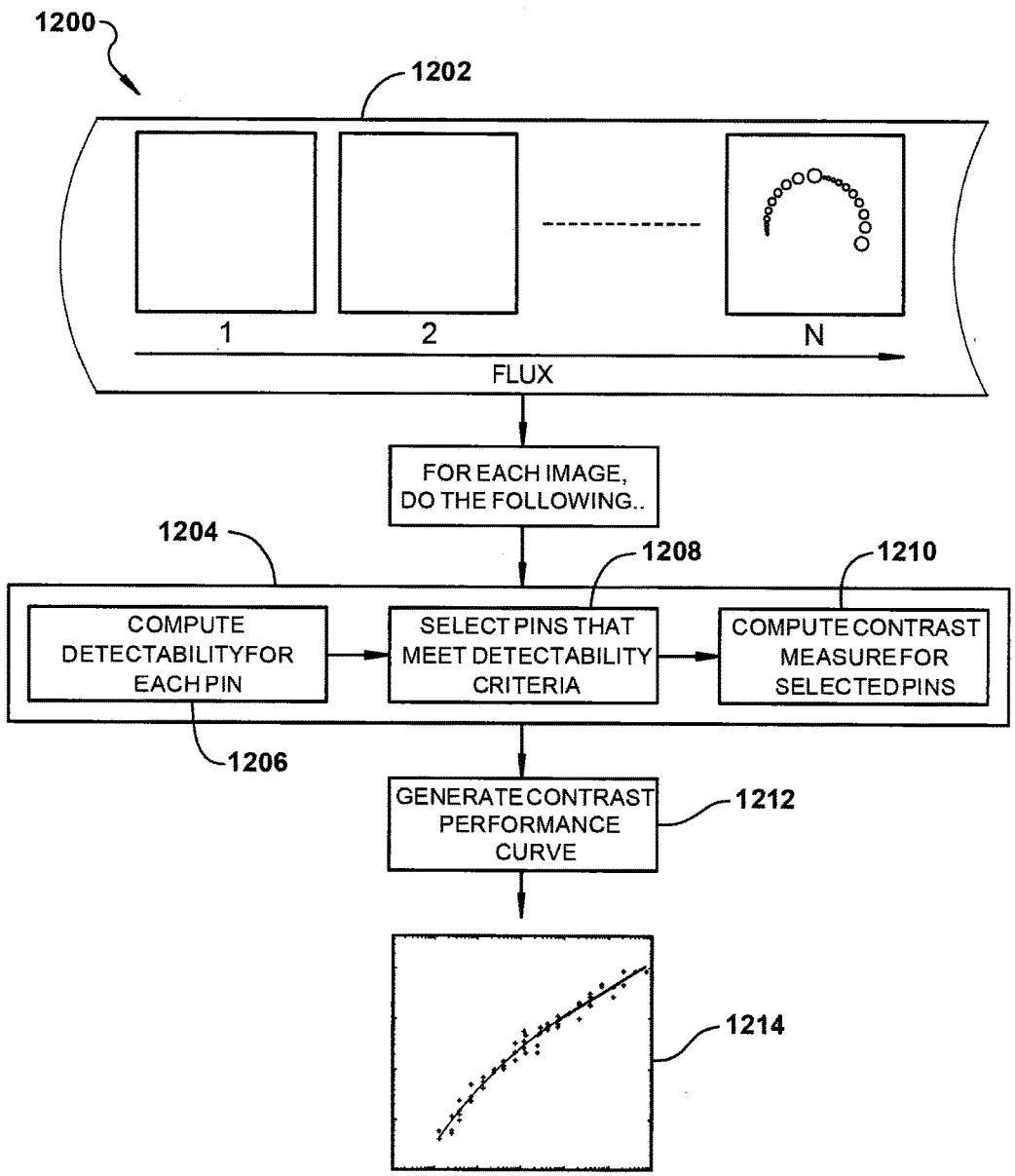
FIG. 12 is a flow chart of an embodiment of an ExLCD method.

In some embodiments and referring to flow chart 1200 in FIG. 12, a set of image slices 1202 at varying flux levels is obtained by scanning an ExLCD phantom 300. For each image 1 . . . N of image slice set 1202, a selection process 1204 is performed. Selection process 1204 includes, at block 1206, computing a detectability for each pin 402 of phantom 300, selecting pins 402 that meet a detectability criterion at block 1208, and computing a contrast measure at block 1210 for the pins selected at block 1208. The computed contrast measures for the set of images 1202 are used by a contrast performance curve module to generate or compute, at block 1212, a contrast performance curve graph 1214. Contrast performance curve graph 1214 is provided to a user in a tangible form in some embodiments. This form may be, for example, a printed graph. In some embodiments, it is provided electronically, such as in a ROM, a RAM, a DVD, a CD, or in some other electronically readable (including electronic computer optics and magnetics) form and may be stored permanently (or in some embodiments, erasably) thereon or therein. In some embodiments, the form may be a hard magnetic disk drive or other memory. In some embodiments, graph 1214 is provided in a form that is or can be stored in a memory unit of the radiographic scanner used to generate the curve.

As used herein, the terms "extended low contrast detectability" and "ExLCD" refer to a performance relationship for a radiographic imaging system that provides numeric LCD values (Contrast Index) over a range of operating conditions and patient sizes (Flux Index). The terms "extended low contrast detectability function", "ExLCD function" and "ExLCD performance function" and "ExLCD performance curve" and "Contrast Performance Curve" refer to a data representation or to a tangible representation of the Contrast Index vs. Flux Index relationship.

Figure 13:
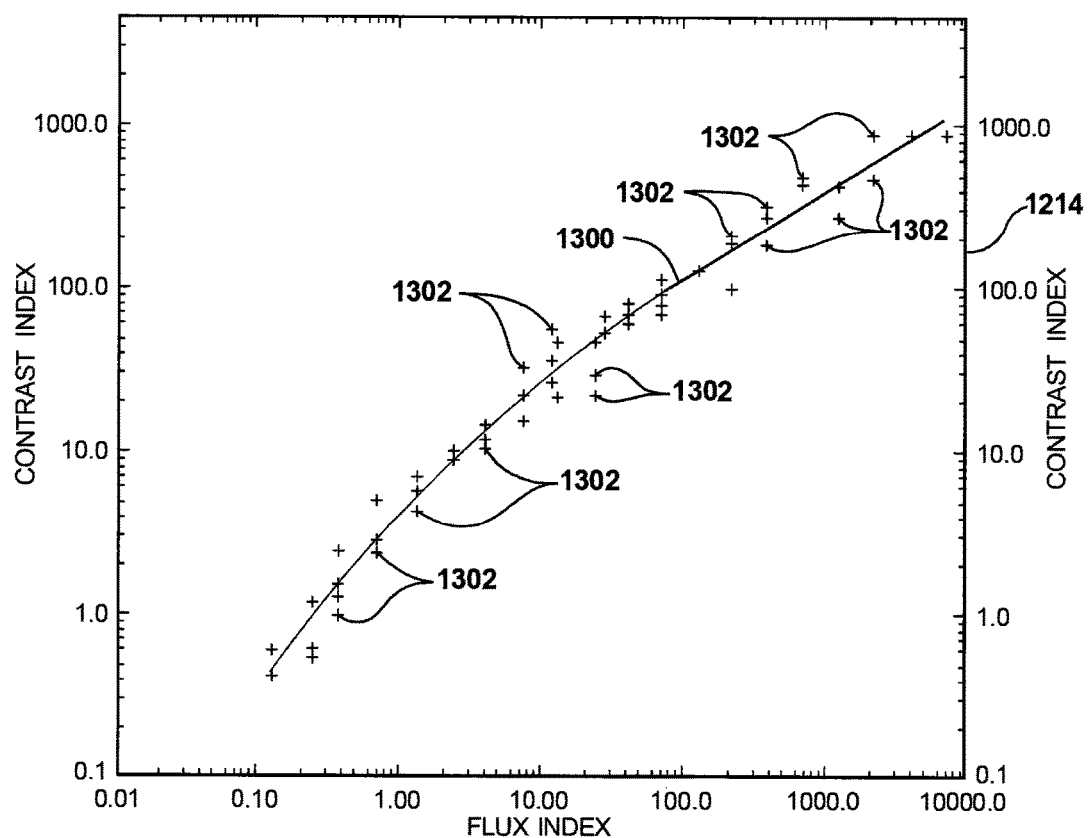
FIG. 13 is a drawing of an ExLCD contrast performance curve derived from contrast measurements of a typical simulated CT scanner.

Referring now to FIG. 13, an ExLCD contrast performance curve 1300 for a typical (simulated) CT scanner is shown along with a set of contrast measurements 1302 made over an entire flux range of the scanner. (Not all contrast measurements 1302 are labeled in FIG. 13.) CT systems vary in their contrast performance based on system characteristics that can include overall dose/quantum efficiency, system/electronic noise, system blurring (MTF), and/or implementation of non-linear reconstruction methods.

Figure 14:
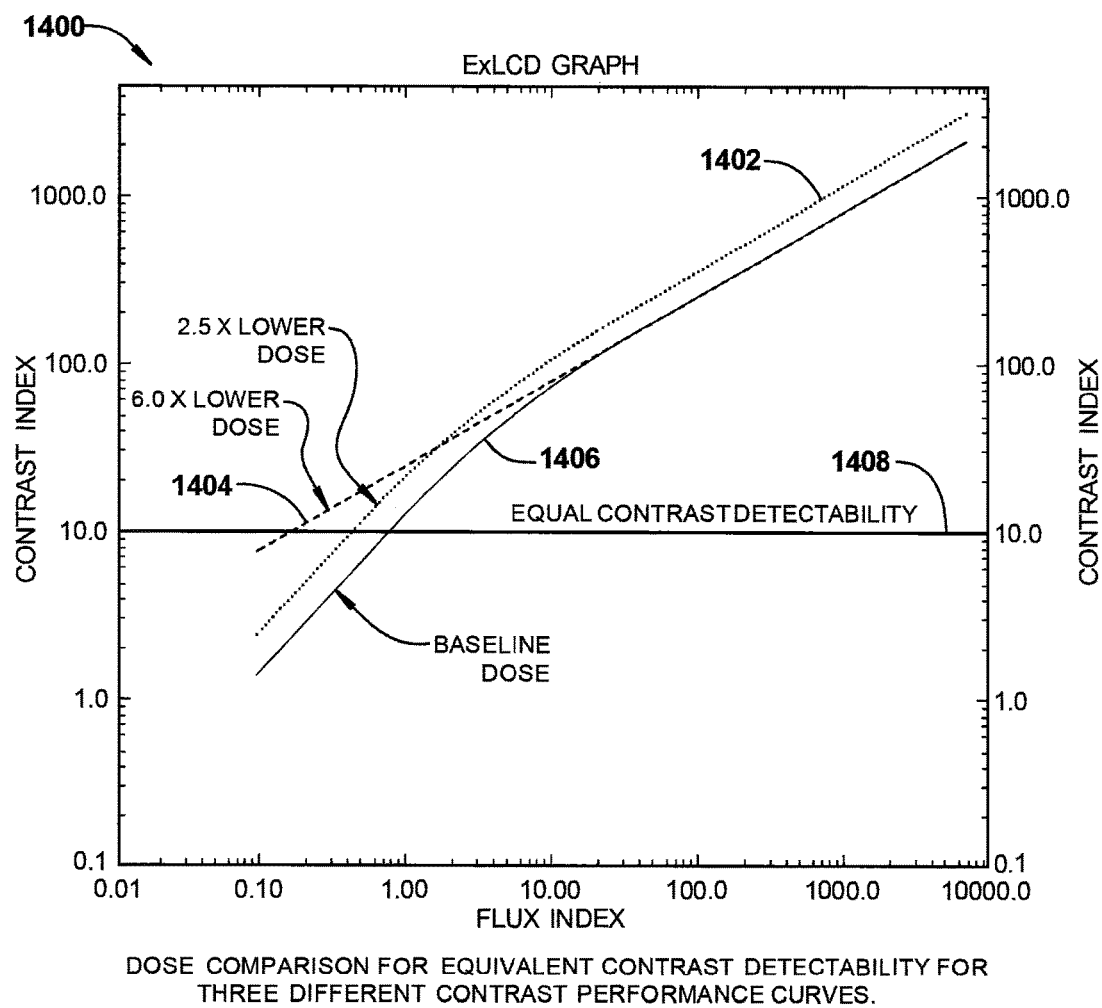
FIG. 14 is a graph illustrating qualitatively how a contrast performance curve is affected by some system characteristics.

Referring now to graph 1400 of FIG. 14, dotted and dashed traces 1402 and 1404, respectively, illustrate qualitatively how the contrast performance curve is affected by some of these system characteristics. In graph 1400, dotted line 1402 represents a radiographic system having a high quantum efficiency. Dashed trace 1404 represents a radiographic imaging system having low system noise and/or improved non-linear reconstruction. Solid trace 1406 represents a baseline contrast performance curve. Each trace 1402, 1404, and 1406 represents a hypothetical ExLCD performance curve that might be representative of a different physical radiographic imaging system. Line 1408 is a line drawn at a constant detectability of 10.0. At this contrast detectability, the intersections of traces 1402, 1404, and 1406 with line 1408 show that the high quantum efficiency system can deliver an image contrast index of 10.0 with a dose 2.5 times lower than the baseline system, and the system having lower noise and/or improved non-linear reconstruction at a dose 6.0 times less than the baseline system.

In some embodiments, a FluxIndex value is defined for each protocol variation within a core operating mode to incorporate those protocol parameters that affect the x-ray flux available for detection or image performance reconstruction parameters. The Flux Index value is "relative" to the core operating mode in that a Flux Index value for one core operating mode cannot be directly compared to a Flux Index value for another core operating mode. The relative Flux Index value, for a specific core operating mode, is any expression that is proportional to the x-ray flux available for detection. By way of example, for a CT scanner, a possible definition is written as in Equation (9) below and as explained in the accompanying descriptions.

Contrast Index

A relative flux measure, designated as the "flux index," incorporates these five parameters as written in Equations (9):

$$\begin{cases} FluxIndex = \dfrac{CTDIvol}{CTDIvol_{ref}} \times (mA) \times (sliceThick) \times (scanTime) \times \dfrac{e^{-(objDiam) \times (attWater)}}{e^{-(refDiam) \times (attWater)}} \\ refDiam = 20.0 \text{ cm} \end{cases} \quad (9)$$

CTDIvol is per 100 mAs and $CTDIvol_{ref}$ is an arbitrary constant dose reference value per 100 mAs that will be determined for each core operating mode tested. The CTDIvol ratio is optional in Equation (9) because it is included to normalize flux index for making dose comparisons. For practical combinations of these parameters, the range of FluxIndex is approximately [0.1, 7,000.0]. An example of a current LCD specification could be "4 mm at 0.3% for 10 mm slice at 90 mAs." Because this example relates to the 20 cm CATPHAN® phantom, FluxIndex would be 900.

The relative FluxIndex described above relates linearly to dose except for the factor involving the object diameter. The currently accepted dose index for CT is CTDIvol as defined in IEC 60601-2-44. Dose is linearly related to flux for a given object size and slice thickness.

To extend the measurement of low contrast detectability, some embodiments use a new contrast measure M. This contrast measure is written as:

$$M = \frac{M_0}{cp} \quad (10)$$

and is designated as the "contrast index." In Equation (10), p is the smallest pin size, measured in millimeters, visible at contrast level c, measured in Hounsfield units (HU) where one Hounsfield unit corresponds to 0.1% of water attenuation, and $M_0$ is an arbitrary constant for bringing the measure M into a convenient numerical range. It is important to note that contrast level c in this definition is the nominal or expected contrast level of the object as opposed to a measured contrast level, which is later indicated with an upper case C. (In another embodiment, p is the diameter of a pin and c is the contrast at which a pin of that diameter is determined to be detectable.) In this example, $M_0$=6000 is used to map the best current contrast specification of 2 mm at 0.3% to a contrast measure of 1000. For example, the specification, "4 mm at 0.3% contrast for 10 mm slice thickness at 30 mGy CTDIvol," would generate a contrast measure of 500 written as $$M = \frac{6000}{(3)(4)} = 500. \tag{11}$$

In other embodiments, the contrast index is obtained by applying a threshold to the SNR calculation for detectability from CHO, NPWMF, etc. And in yet other embodiments, the SNR itself is used for detectability.

In some embodiments, a Contrast Index value is written in Equation (10) as is described in the accompanying descriptions. For example, a Contrast Index is determined by measurement and calculation for each protocol within any core operating mode and for each relevant contrast set. For a given core operating mode, each set of contrast objects is assigned a nominal contrast level, c, that is set by the manufacturing characteristics of the phantom as determined by the phantom design and the phantom calibration done for the core operating mode. The detectability p and contrast c of each detectable object size is then determined for each protocol within the core operating mode. As described elsewhere herein, in some embodiments, a detectability value for each object size in the contrast set is determined by examining the image(s) produced for that protocol and then determining a smallest object size, p, that corresponds to a detectability value that is greater than or equal to the detectability threshold.

A contrast set is relevant for a given set of protocol parameters if either some but not all objects in the set are detectable. In some embodiments of the present invention, the detectability of an object is reliably determined by extrapolation or interpolation from the detectability measures of the objects in the contrast set.

In some embodiments, a plurality of calibrations for a given radiographic imaging system is performed. In one example, a complete ExLCD Scanner Characterization includes the following steps:
(a) A new ExLCD Calibration is performed for each core operating mode. The core operating mode changes when changes are made in core operating parameters, e.g.
  (1) X-ray tube energy;
  (2) Source filter and collimator; and/or
  (3) Reconstruction mode, e.g. non-linear reconstruction;
(b) Up-to-date dose measurement; and
(c) Calibration of the ExLCD Phantom to compensate for manufacturing tolerances and scanner spectral characteristics.

As referred to herein, an ExLCD performance curve or ExLCD performance function is one form or format of an output of an embodiment of the present invention for a core operating mode for the radiographic imaging system. The ExLCD performance curve is indicative of a relation between the Flux Index and the Contrast Index over a range of the Flux Index for that core operating mode. In some embodiments, the ExLCD performance function is represented as an array of Flux Index and Contrast Index values or by another appropriate parameterization. In some embodiments, the relation is provided in a form that provides a capability (e.g., an on-line capability) to determine a Contrast Index for any desired Flux Index or conversely to determine the protocol parameters for any desired Contrast Index and any patient size.

Some embodiments of the present invention include apparatus and/or methods for ascertaining the quality of an image interpretation task. Some of these apparatus and/or methods include one or more of human opinions of object visual quality in fixed object phantoms (poorest of methods), human task based observations regarding how accurately the presence or absence of an object in an image can be determined (forced alternative choice methods, for example), statistical noise analysis methods whereby the detectability of an object is inferred using some measure of image noise, matched filter methods whereby object spatial frequencies are determined and then used to analyze noise within those spatial frequencies, an ideal Bayesian Observer signal to noise analysis, a Non Pre-whitening Matched Filter signal to noise ratio (NPWMFSNR), etc. Methods and apparatus recited in this paragraph are described, for example, by the International Commission on Radiation Units and Measurements (ICRU) Report 54 "Medical Imaging—The Assessment of Image Quality", wherein is incorporated herein by reference. NPWMFSNR has been found to most closely represent objective human task based assessments. The NPWMFSNR is therefore used in some embodiments of the present invention although other methods are employed in other embodiments. In some embodiments of the present invention, a variation of the NPWMFSNR that measures a reduction in contrast of the object due to the MTF of the system is used. In some of these embodiments, systems that reduce the spatial frequencies of the noise but retain the spatial frequencies of the input object will score a higher NPWMFSNR.

Dual Energy

Embodiments of the present invention can be used in energy discriminating radiographic imaging in a manner similar to that used in energy integrating imaging with some modifications. For example, in some embodiments, objects within a phantom used for calibration comprise an energy sensitive material such as calcium hydroxyapatite. The phantom objects comprise various percentages of the energy sensitive material to allow concentration sets of energy sensitive material objects to be built, thereby making the phantom objects sensitive to the energy discrimination acquisition and reconstruction methods employed by the radiological imaging device.

Energy discriminating systems can provide various types of images. For example, for dual energy CT, these images may, in some embodiments, include high kV and low kV images that are comparable to conventional images. In some embodiments, a set of basis material images such as a calcium image and water image (if the basis materials chosen are calcium and water) are included. Also in some embodiments, monochromatic images at a selected keV that are produced by an appropriate combination of data from the basis material images or basis material projection data are included. One or a plurality of such types of images is evaluated by methods employing ExLCD using an energy sensitive phantom in some embodiments.

ExLCD Phantom

In some embodiments of the present invention, an ExLCD phantom 300, such as the one best seen in FIGS. 3, 4, 5, and 6, is used to make contrast measurements over the flux range. For example, in some embodiments, a phantom diameter of 20 cm is used to support flux values at the high flux end of the desired range. To achieve the lowest flux values in a desired range with appropriate scan parameters, a second phantom diameter of 40 cm is provided.

When the detected flux is at the lower end of the desired range, the contrast levels in at least one known CATPHAN® will not be seen. Therefore, additional contrast sets are introduced to be detectable in the low flux ranges.

Figure 15:
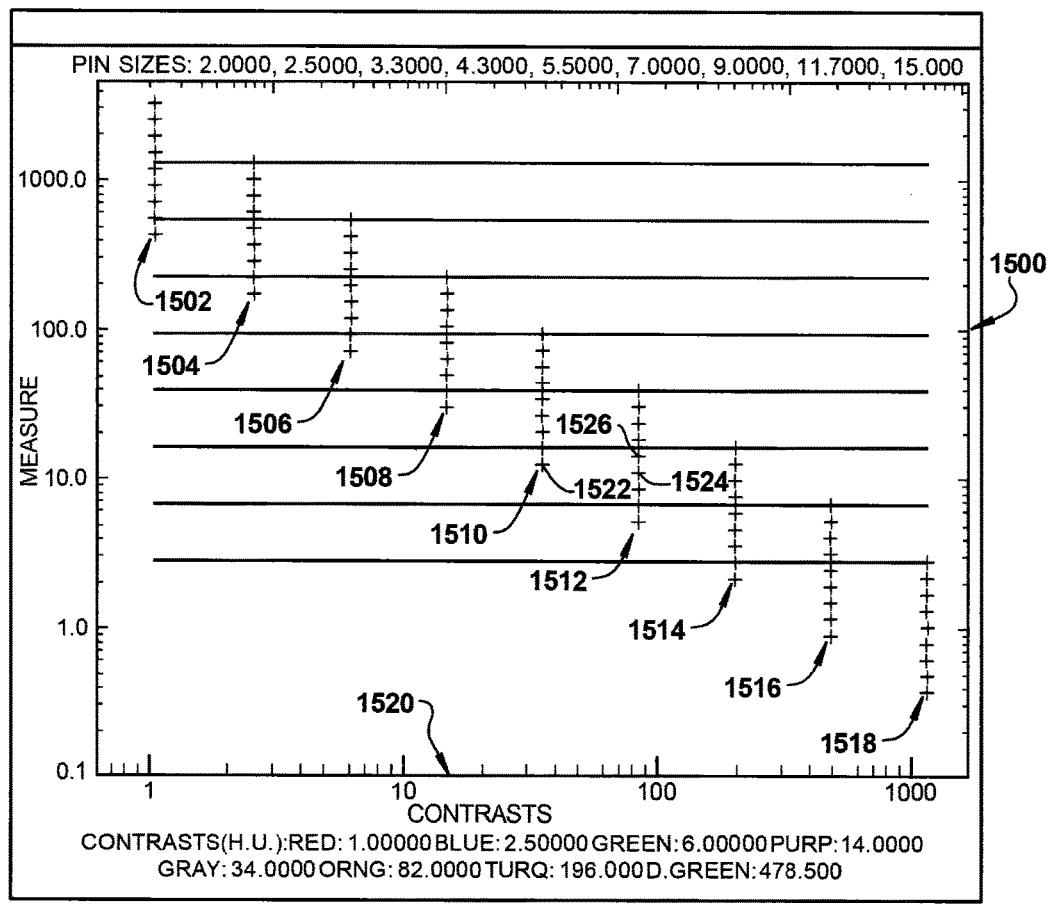
FIG. 15 is a graph illustrating pin size sampling and contrast set sampling.

Specifically, in FIG. 15, any contrast set (except the set with the lowest contrast value) such as contrast set 1510, has a smallest pin, represented by point 1522 on graph 1500, that is positioned between the fourth and fifth pins of the contrast set with the next lower contrast value, which, in this example, are represented by points 1524 and 1526, respectively, of contrast set 1512.

Pin sizes and specific contrast level values in an example embodiment are shown in Table 2. For each contrast level, there is an indication of whether that contrast level is required with the 20 cm diameter, the 40 cm diameter or both.

TABLE 2

| Pin No. | 1 | 2 | 3 | 4 | 5 | 6 | 7 | 8 | 9 |
|---|---|---|---|---|---|---|---|---|---|
| Size (mm) | 2.00 | 2.57 | 3.31 | 4.26 | 5.48 | 7.05 | 9.06 | 11.66 | 15.00 |
| Contrast Set No. | | 1 | | | 2 | | | 3 | |
| Contrast Levels (HU) | 1.0 | 2.41 | 5.83 | 14.08 | 33.99 | 82.07 | 198.17 | 478.49 | 1155.35 |
| Used with 20 cm diameter | Yes | Yes | Yes | Yes | Yes | Yes | No | No | No |
| Used with 40 cm diameter | No | No | No | Yes | Yes | Yes | Yes | Yes | Yes |

In at least one ExLCD phantom embodiment and referring to FIG. 15, the ExLCD phantom includes nine distinct contrast sets, 1502, 1504, 1506, 1508, 1510, 1512, 1514, 1516, 1518. Each contrast set, itself, includes nine objects, which are herein referred to as "pins." The pin sizes are chosen to generate uniform samples along a logarithmic contrast level axis 1520. The uniform samples are derived by the following formulation:

Let the number of samples be N, and let $V_1$ and $V_N$ be the first and last elements, and ramp=1, 2, 3, ..., N. Then $V_1$ and $V_N$ can be written as:

$$V_1 = a^{b+1} \tag{12}$$

$$V_N = a^{b+N} \tag{13}$$

and $$b + 1 = \log_a(V_1) = \frac{\ln(V_1)}{\ln(a)} \tag{14}$$

$$b + N = \log_a(V_N) = \frac{\ln(V_N)}{\ln(a)}. \tag{15}$$

Solving equations (14) and (15), $$a = e^{\left(\frac{\ln(V_N) - \ln(V_1)}{N-1}\right)} \tag{16}$$

and $$b = \frac{\ln(V_1)}{\ln(a)} - 1. \tag{17}$$

Hence the equally sampled vec can be defined as $$vec = a^{(b+ramp)} \tag{18}$$

The contrast sets in this embodiment are designed so that the effective sampling rate along the logarithmic contrast level axis 1520 is double that which is available from an individual pin. In one such design, contrast sets are interleaved.

Figure 16:
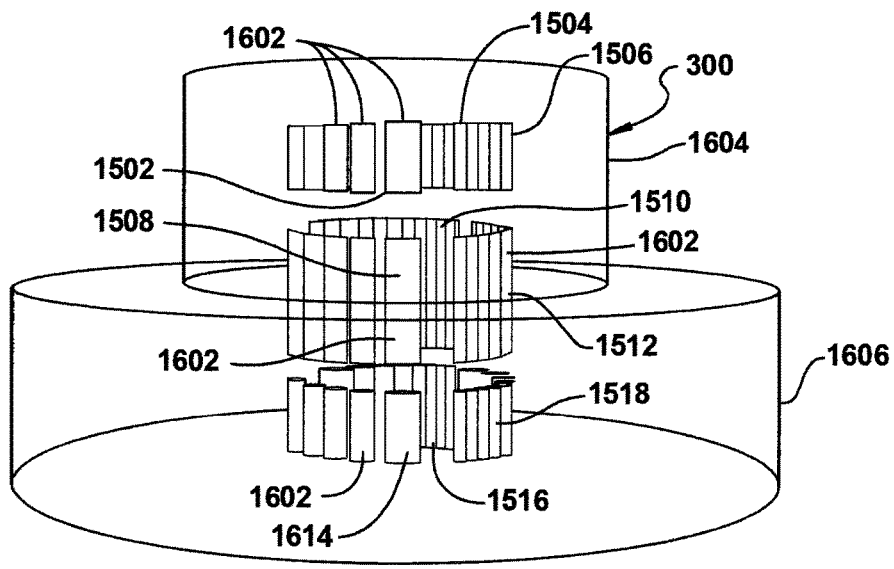
FIG. 16 is a see-through perspective view of an ExLCD phantom embodiment.

In some embodiments, a phantom 300 is configured in accordance with Table 2 and as illustrated in FIG. 16. The varying contrast levels of contrast sets 1502, 1504, 1506, 1508, 1510, 1512, 1514, 1516, 1518 are depicted by various pegs 1602 (only some of which are indicated), positioned longitudinally inside phantom 300. In FIG. 16, the middle three contrast sets 1508, 1510, 1512 are positioned so that they can be used with both of the two diameter sections 1604 and 1606.

Figure 17:
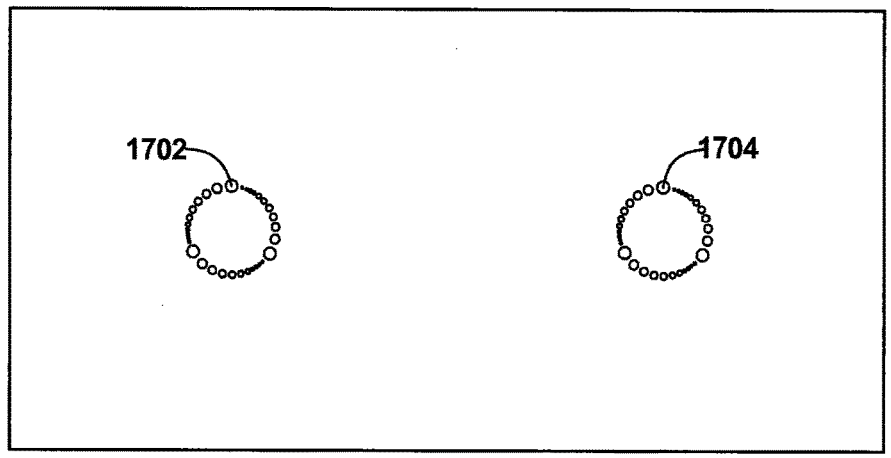
FIG. 17 is a view of simulated cross sections of different diameter sections of the phantom shown in FIG. 16.

Representative cross-sections 1702 and 1704 for at least one embodiment are illustrated in FIG. 17. The image on the left illustrates a 20 cm diameter cross-section 1702; the image on the right illustrates a 40 cm diameter cross-section 1704. The phantom is configured so that there are a plurality of slices with the same cross-section and contrast set. By combining the measurements from the multiple slices, a more accurate measurement of the actual contrast of the reconstructed object is obtained.

Additionally, in some embodiments, the phantom includes regions in which noise standard deviation and noise power spectrum can be measured. Also in some embodiments, the phantom includes a region and/or object to support measuring the system MTF.

Figure 18:
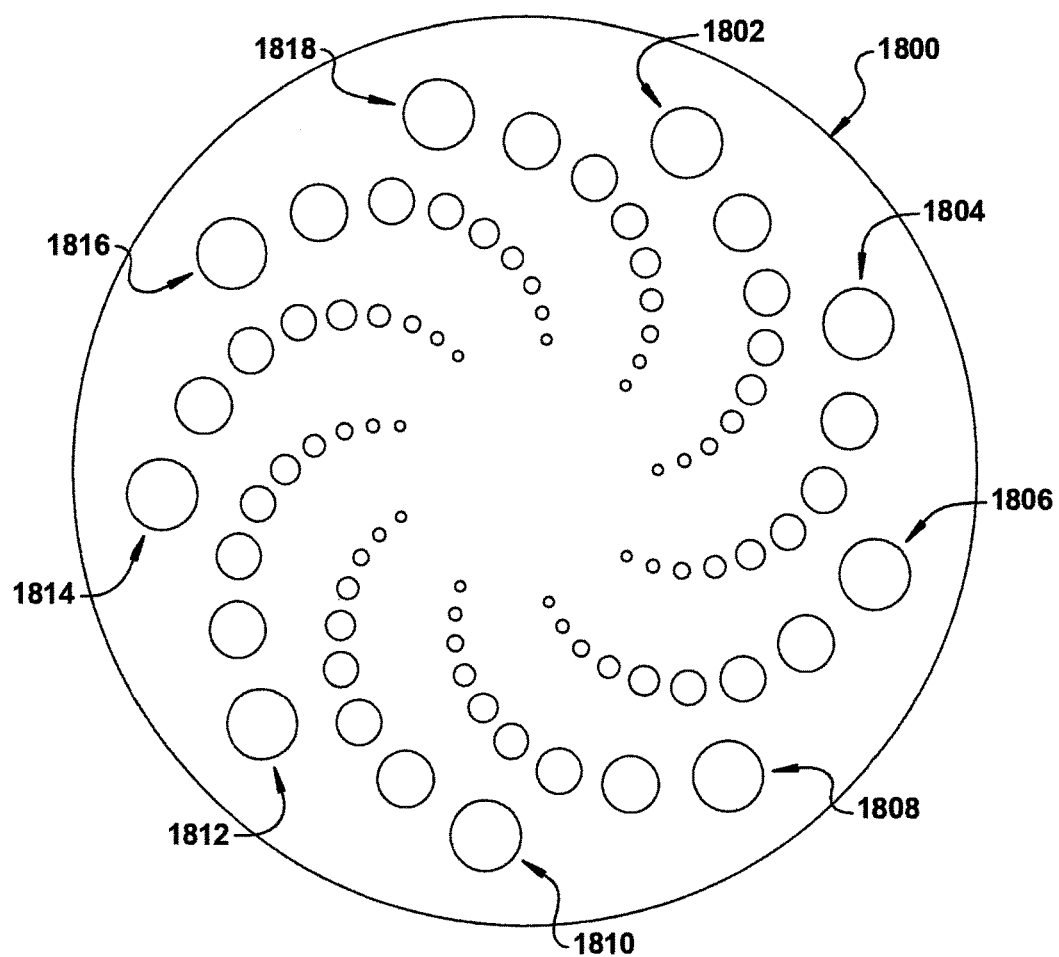
FIG. 18 is a two-dimensional cross-sectional view of an alternative embodiment of an ExLCD phantom.
Figure 19:
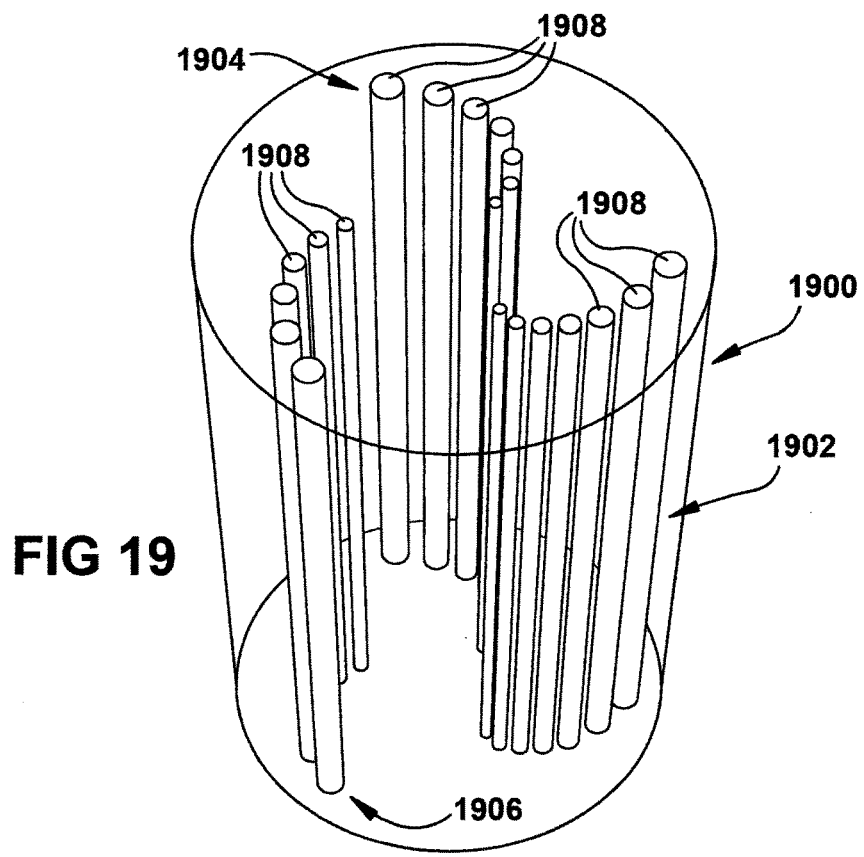
FIG. 19 is a see-through perspective view of another alternative embodiment of an ExLCD phantom.
Figure 20:
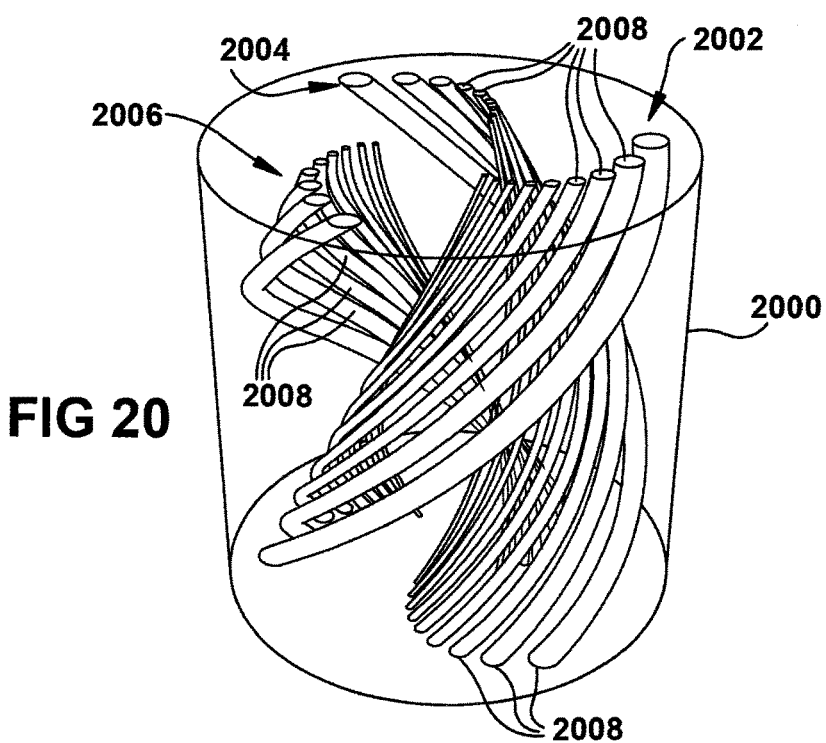
FIG. 20 is a see-through perspective view of yet another alternative embodiment of an ExLCD phantom.

In at least one other embodiment and referring to FIG. 18, an ExLCD phantom has a cross-section 1800. Different contrast levels are provided by pins in curvilinear contrast groups 1802, 1804, 1806, 1808, 1810, 1812, 1814, 1816, 1818. In this embodiment, all contrast levels and pin sizes appear in each cross-section. Methods using this design include those in which the noise response in the reconstruction as a function of radius is incorporated. Two embodiments 1900 and 2000 sharing the cross-section 1800 are shown in FIGS. 19 and 20, respectively. For clarity in both depictions, only three contrast sets are shown in each figure, 1902, 1904, 1906, and 2002, 2004, 2006, respectively. ExLCD phantom embodiment 1900 comprises cylindrical objects, some of which are denoted as objects or pins 1908. Phantom pins 1908 provide consistent objects from slice to slice that approximate or simulate axially oriented vessels in a patient to test a non-linear reconstruction processing that takes advantage of slice to slice consistency. ExLCD phantom 2000 comprises objects, some of which are denoted as objects or pins 2008, that are helical cylinders, i.e., for each such object, centers of the circular profiles in the horizontal two-dimensional cross-sections form a helix. This format helps reduce coherence between slices and can be used to calibrate performance when slice to slice variation is present and/or to facilitate testing non-linear and iterative reconstruction processing that takes advantage of slice to slice consistency. Either phantom 1900 or phantom 2000 can be provided with a plurality of diameters. An embodiment using 20 cm and 40 cm diameters is shown in FIG. 16.

In another embodiment of ExLCD phantom, the contrasts in the sections are chosen so that when a logarithm sampling in Flux Index is used, the expected Contrast Index as computed using Equation (3) of one or more pins in a section with one diameter that will match the expected Contrast Index in one or more pins in one or more sections with another diameter.

It will be recognized that not all ExLCD phantom embodiments will have the same number(s) of different diameter sections, pins, and or contrast groups as the example embodiments described herein.

ExLCD Protocols

In at least one embodiment of the present invention, there are 20 distinct protocol samples, which, for example, are selected between 0.09 and 7,200.0 and that are uniformly distributed on a logarithmic relative flux axis. The specific values for relative flux are shown in Table 3 below along with the corresponding scan parameters and phantom diameter.

TABLE 3

Relative Flux Values for Selected Protocols

| # | Relative Flux | mAs | Slice Thickness (mm) | Diameter (cm) |
|---|---|---|---|---|
| 1 | 0.092 | 5 | 1 | 40 |
| 2 | 0.183 | 10 | 1 | 40 |
| 3 | 0.275 | 15 | 1 | 40 |
| 4 | 0.549 | 30 | 1 | 40 |
| 5 | 1.099 | 60 | 1 | 40 |
| 6 | 1.832 | 100 | 1 | 40 |
| 7 | 3.297 | 90 | 2 | 40 |
| 8 | 6.044 | 110 | 3 | 40 |
| 9 | 10.989 | 200 | 3 | 40 |
| 10 | 19.781 | 360 | 3 | 40 |
| 11 | 36.631 | 400 | 5 | 40 |
| 12 | 63.006 | 430 | 8 | 40 |
| 13 | 60.000 | 60 | 1 | 20 |
| 14 | 40.000 | 20 | 2 | 20 |
| 15 | 20.000 | 20 | 1 | 20 |
| 16 | 10.000 | 10 | 1 | 20 |
| 17 | 115.000 | 115 | 1 | 20 |
| 18 | 200.000 | 200 | 1 | 20 |
| 19 | 360.000 | 360 | 1 | 20 |
| 20 | 660.000 | 330 | 2 | 20 |
| 21 | 1200.00 | 150 | 8 | 20 |
| 22 | 2160.00 | 270 | 8 | 20 |
| 23 | 3840.00 | 480 | 8 | 20 |
| 24 | 7200.00 | 900 | 8 | 20 |

Figure 21:
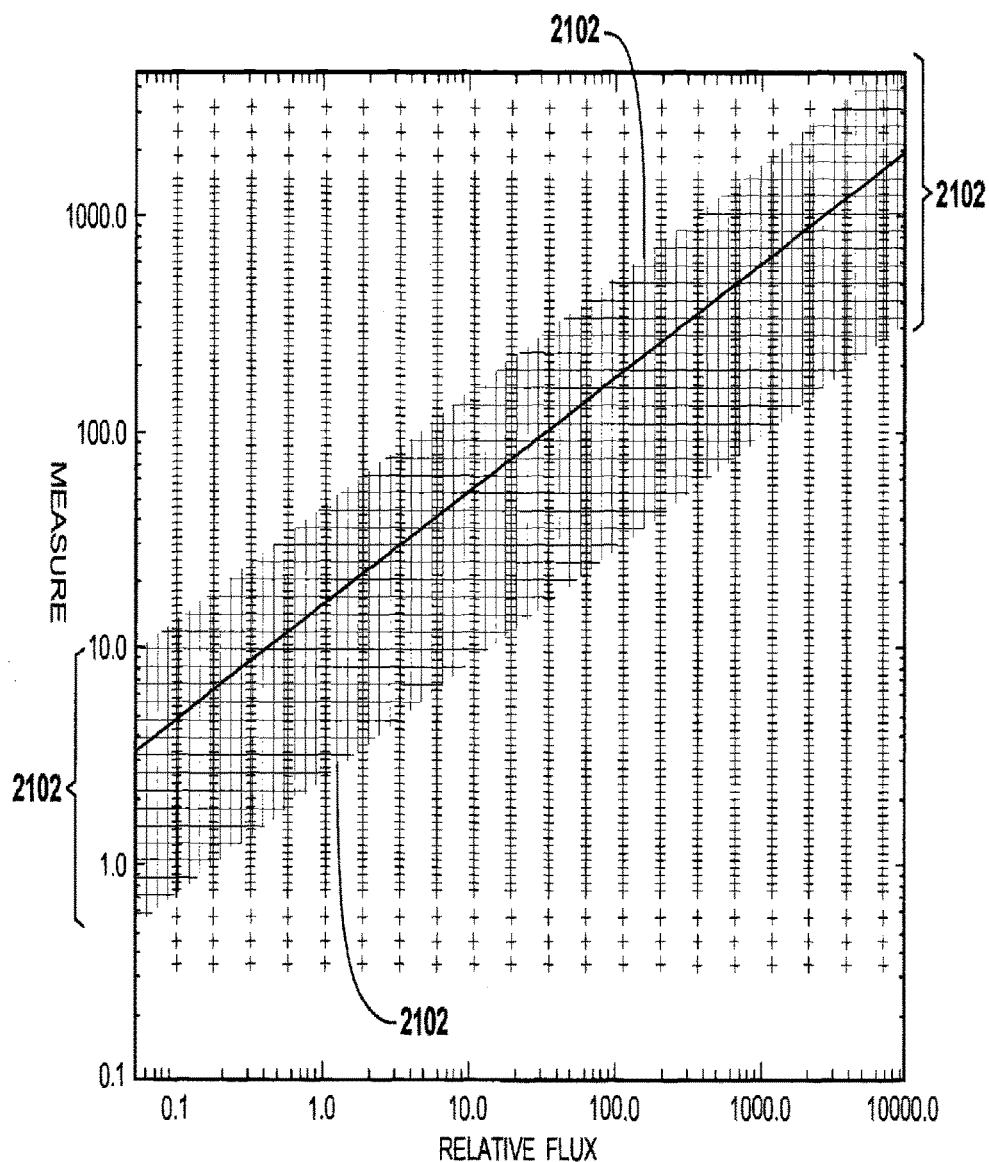
FIG. 21 is a example of a graph of contrast sets represented at each protocol of a CT scanner.

There are 12 distinct slices (cross-sections) of this ExLCD phantom embodiment as shown by the number of check marks (✓). Each of those 12 slices could be scanned for each of the 20 protocols resulting in 240 image slices. However, examination of FIG. 21 illustrates that only a relatively small subset of the 240 possible image slices is relevant. Hatched region 2102 in FIG. 21 represents the approximate coverage that is used, i.e., the relevant contrast sets. Slice thicknesses should be measured to accurately determine the Flux Index, because there can be differences between the nominal selected slice and the true slice sensitivity profile.

Based on this analysis of this example embodiment, 44 image slices were included in the ExLCD measurement process shown in Table 4.

TABLE 4

Image slices selected for ExLCD measurement processing

| # | Relative Flux | mAs | Slice Thickness (mm) | Diameter (cm) | Contrast Set |
|---|---|---|---|---|---|
| 1 | 0.092 | 5 | 1 | 40 | 2 |
| 2 | 0.183 | 10 | 1 | 40 | 2 |
| 3 | 0.275 | 15 | 1 | 40 | 2 |
| 4 | 0.549 | 30 | 1 | 40 | 2 |
| 5 | 1.099 | 60 | 1 | 40 | 2 |
| 6 | 1.832 | 100 | 1 | 40 | 2 |
| 7 | 3.297 | 90 | 2 | 40 | 2 |
| 8 | 6.044 | 110 | 3 | 40 | 2 |
| 9 | 0.092 | 5 | 1 | 40 | 3 |
| 10 | 0.183 | 10 | 1 | 40 | 3 |
| 11 | 0.275 | 15 | 1 | 40 | 3 |
| 12 | 0.549 | 30 | 1 | 40 | 3 |
| 13 | 1.099 | 60 | 1 | 40 | 3 |
| 14 | 1.832 | 100 | 1 | 40 | 3 |
| 15 | 3.297 | 90 | 2 | 40 | 3 |
| 16 | 6.044 | 110 | 3 | 40 | 3 |
| 17 | 10.989 | 200 | 3 | 40 | 1 |
| 18 | 19.781 | 360 | 3 | 40 | 1 |
| 19 | 36.631 | 400 | 5 | 40 | 1 |
| 20 | 63.006 | 430 | 8 | 40 | 1 |
| 21 | 60.000 | 60 | 1 | 20 | 1 |
| 22 | 40.000 | 20 | 2 | 20 | 1 |
| 23 | 20.000 | 20 | 1 | 20 | 1 |
| 24 | 10.000 | 10 | 1 | 20 | 1 |
| 25 | 10.989 | 200 | 3 | 40 | 2 |
| 26 | 19.781 | 360 | 3 | 40 | 2 |
| 27 | 36.631 | 400 | 5 | 40 | 2 |
| 28 | 63.006 | 430 | 8 | 40 | 2 |
| 29 | 60.000 | 60 | 1 | 20 | 2 |
| 30 | 40.000 | 20 | 2 | 20 | 2 |
| 31 | 20.000 | 20 | 1 | 20 | 2 |
| 32 | 10.000 | 10 | 1 | 20 | 2 |
| 33 | 115.000 | 115 | 1 | 20 | 1 |
| 34 | 200.000 | 200 | 1 | 20 | 1 |
| 35 | 360.000 | 360 | 1 | 20 | 1 |
| 36 | 660.000 | 330 | 2 | 20 | 1 |
| 37 | 1200.000 | 150 | 8 | 20 | 1 |
| 38 | 2160.000 | 270 | 8 | 20 | 1 |
| 39 | 3840.000 | 480 | 8 | 20 | 1 |
| 40 | 7200.000 | 900 | 8 | 20 | 1 |
| 41 | 115.000 | 115 | 1 | 20 | 2 |
| 42 | 200.000 | 200 | 1 | 20 | 2 |
| 43 | 360.000 | 360 | 1 | 20 | 2 |
| 44 | 660.000 | 330 | 2 | 20 | 2 |

EXLCD Methods

In some embodiments of the present invention, the ExLCD detectability method includes one or more of the detection methods listed above along with a capability to incorporate actual measured contrast. In some of these embodiments, a pin image contrast is measured as follows:
1. calibrate the phantom to determine the effective mean contrast of the pins;
2. use the calibrated phantom images to define a map of the pixel locations within the geometric area of each pin;
3. use the pin area maps to measure the average contrast for each test condition; and
4. Average the value from multiple slices that are identical in their geometry and contrast set.

Figure 22:
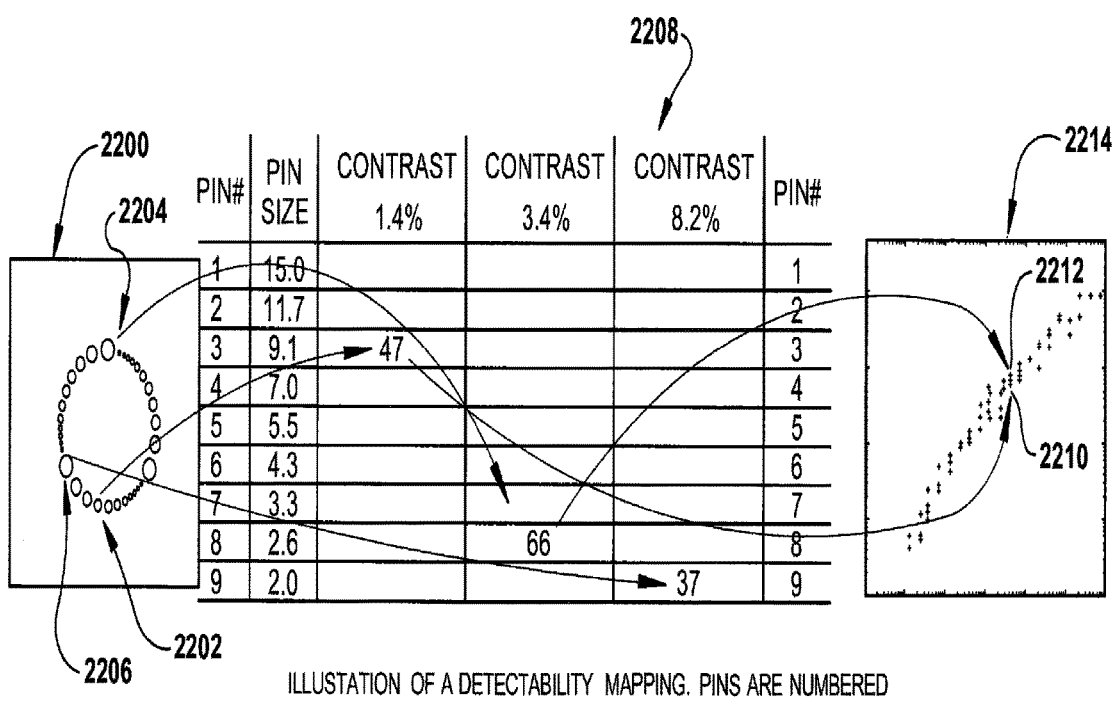
FIG. 22 is an illustration of a result of one embodiment of the detectability determination for a reconstructed image slice described as Test 32 in Table 4.

Referring now to FIG. 22, a result of one embodiment of the detectability determination for a reconstructed image slice 2200 described as Test 32 in Table 4 is shown. The smallest pins 2202, 2204, 2206 detectable in each of three contrast sets are identified as indicated in chart 2208. Based on the identified pin numbers, the corresponding pin sizes 2202 and 2204 and the associated contrast levels 2210 and 2212, respectively, comprise the raw data for the measurement for that reconstructed image 2200.

For example, three ExLCD contrast measurements are recorded using the definition written as Equation (19).

$$\left[ \frac{6000}{9.06 \times 14}, \frac{6000}{2.56 \times 34}, \frac{6000}{2.0 \times 82} \right] = [47, 69, 37]. \quad (19)$$

Figure 23:
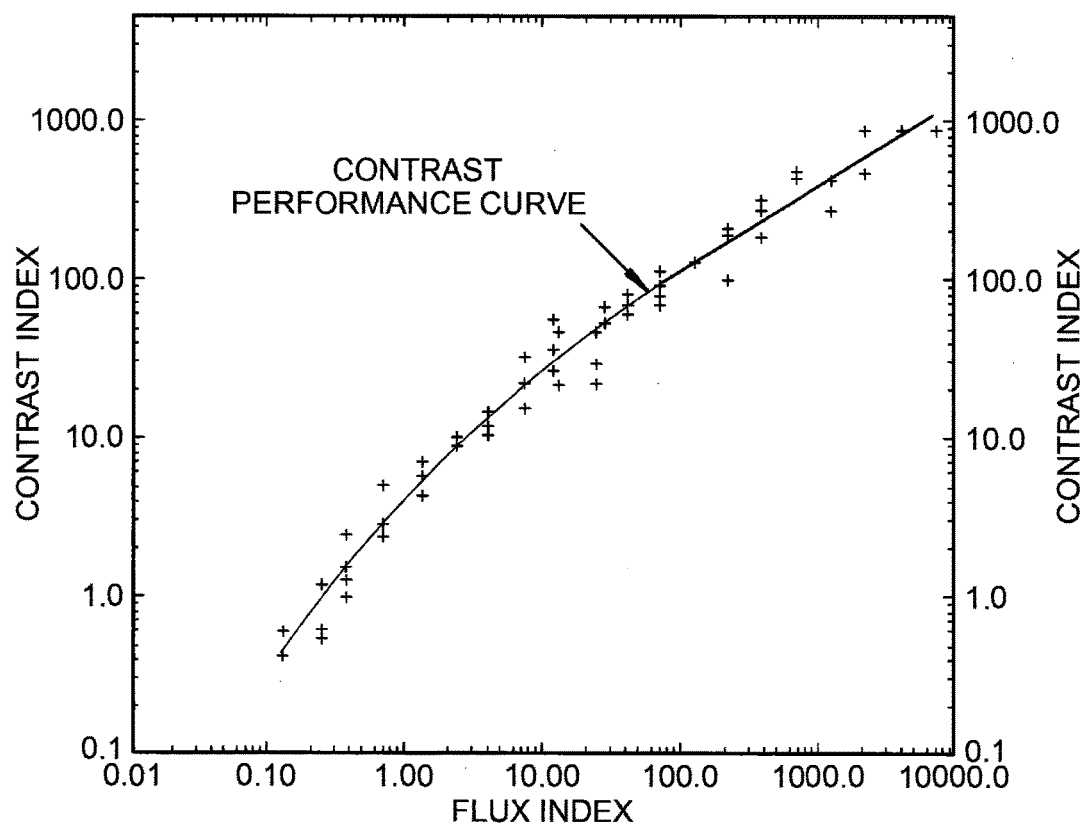
FIG. 23 is an example graph of a Contrast Performance Curve that can be determined by a least squares fitting of ordered pairs to a curve.

For this example, the smallest (2.0 mm) pin is not carried onto the ExLCD contrast measurement plot because it is assumed that there is no way to verify that it is the smallest pin detectable. Therefore, and as shown in FIG. 22, the first two contrast measurements, [47,69] in chart 2200 are carried onto the ExLCD contrast measurement plot 2214 at the Flux Index location (10.0) indicated for Test 32 in Table 4. In FIG. 23, the collection of ordered pairs is shown along with a Contrast Performance Curve that is a regression fit to the collection of ordered pairs.

ExLCD Graph

Figure 24:
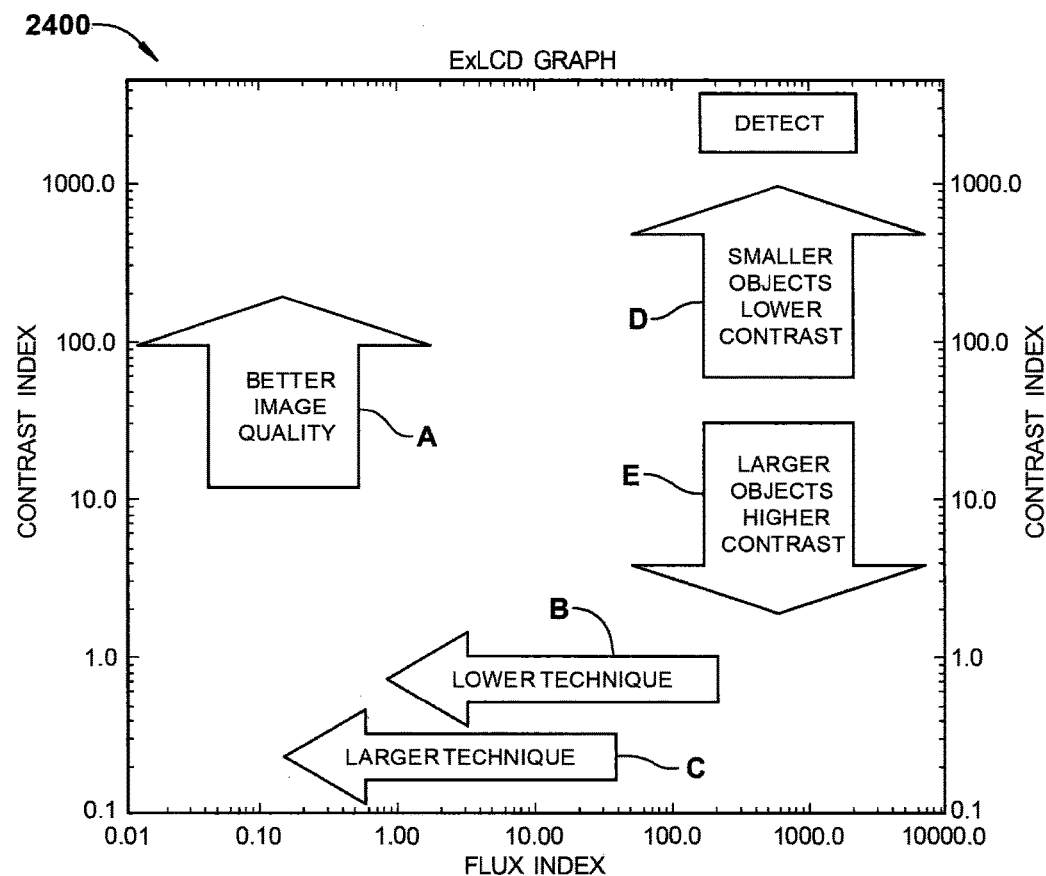
FIG. 24 is an ExLCD graph showing directions of better image quality, lower technique, larger patients, smaller objects (lower contrast) and larger objects (higher contrast).

The range of flux index for at least one known CT scanner is approximately [0.1, 7,000.0]. A corresponding range of contrast index is approximately [0.5, 1000.0]. These ranges define the range or corresponding ranges for other CT scanners of an ExLCD graph. Referring now to graph 2400 of FIG. 24 in log-log format, arrows A, B, C, D, and E generally point in directions of better image quality, lower technique, larger patients, smaller objects (lower contrast) and larger objects (higher contrast), respectively.

Larger values of Contrast Index indicate better image quality or the ability to detect smaller, lower contrast objects. Smaller values of Contrast Index indicate poorer image quality or the ability to detect only larger, higher contrast objects.

Larger values of Flux Index indicate higher dose or smaller patient sizes. Smaller values of Flux Index indicate lower dose or larger patient sizes.

EXLCD Detectability

Figure 25:
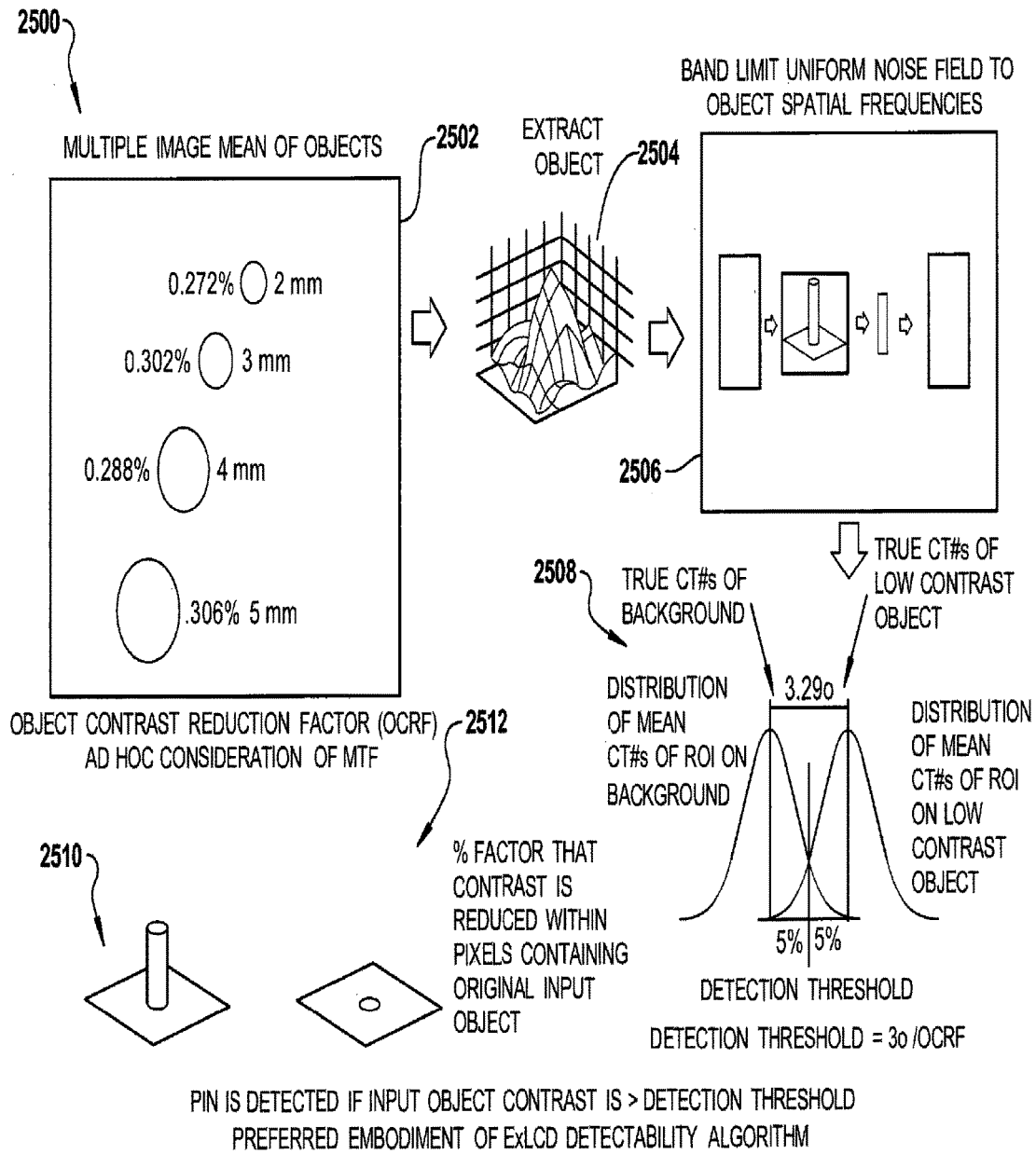
FIG. 25 is a pictorial schematic chart showing an ExLCD detectability embodiment.

Various ExLCD process embodiments can incorporate any combination of detectability methods listed above, one of which, for example, is represented by chart 2500 of FIG. 25. Block 2502 is an average image of multiple scans of the phantom objects. The average reduced the noise so that the pixels represent the object, and block 2504 is a relatively noise-free representation of the object. The ratio of contrast of object 2512 extracted from the image, relative to the contrast of the input object 2510, is the object contrast reduction factor (OCRF). In block 2506, the noise in a uniform region of the image is filtered by convolution with a kernel made with block 2504. The resulting distribution of the filtered noise pixels is offset by 3 standard deviations divided by the OCRF to determine the contrast threshold required to claim detectability.

Single or multiple observer methods may be used to determine detectability within the ExLCD process. For example, in one embodiment, each human observer examines each of the images to assess the detectability for each pin within the contrast sets.

Results of multiple human observers analyzing various ExLCD experiments demonstrate that there is a wide variation in results among human observers. In fact, the variation among observers is large compared to expected measurement variations among CT scanners.

Figure 26:
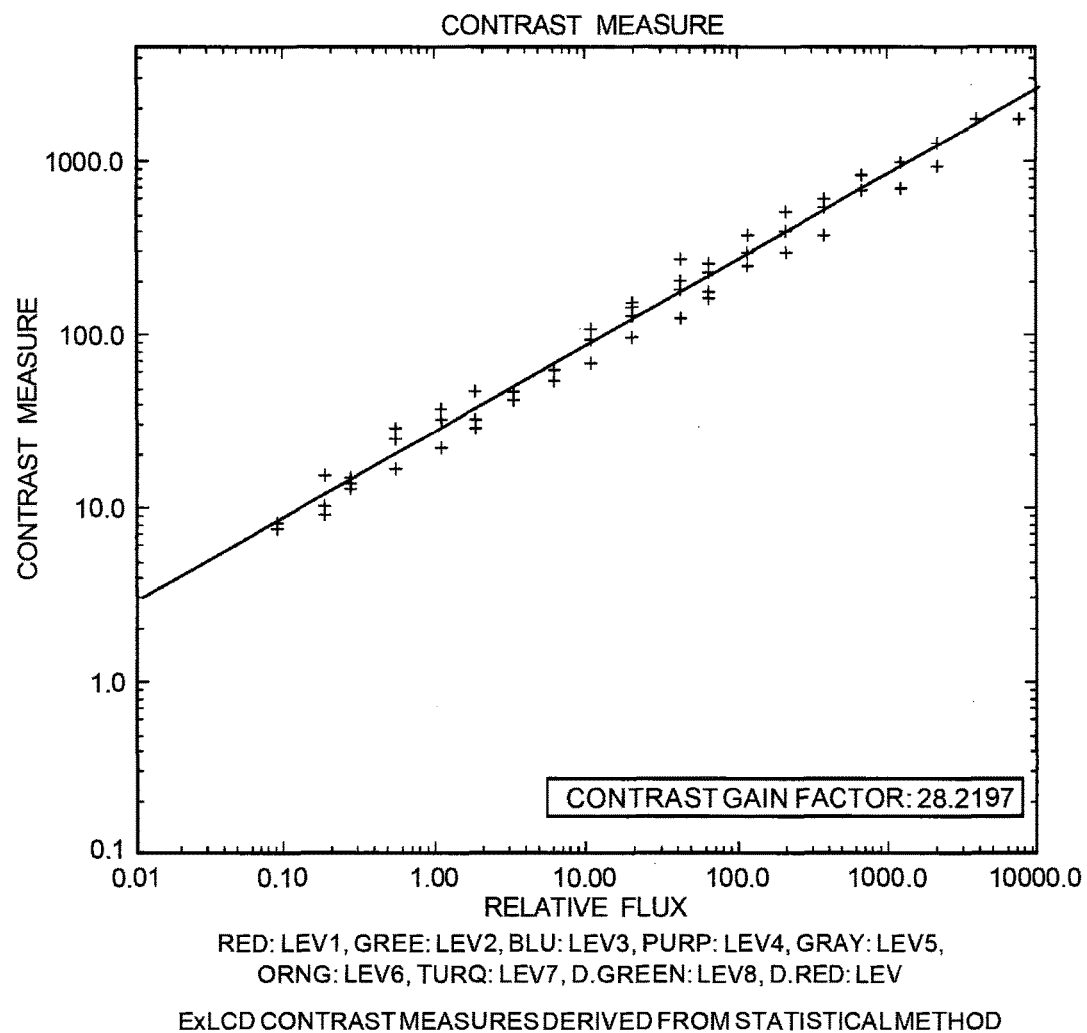
FIG. 26 is an ExLCD contrast measure graph.

A known statistical method from a single protocol LCD method is suitable for use in one embodiment of an ExLCD process. The known prior art statistical method is described, for example, in *Computed Tomography: Principles, Design, Artifacts and Recent Advances*, Jiang Hsieh, Copyright 2003 by the Society of Photo-Optical Instrumentation Engineers, Bellingham, Wash., and is a variation of the Contrast Discrimination Factor (CDF) described in the international standard ASTM E1695-95, "Standard Test Method for Measurement of Computed Tomography (CT) System Performance." The algorithm as described therein is applied to each of 44 images generated in one example embodiment of the ExLCD process. The smallest pin in any contrast level that achieves the background separation is selected for that contrast set. Thus, if the ideal contrast value is at or above the noise standard deviation for that pin size, the contrast measure for that pin and that contrast level is placed onto the ExLCD contrast measure graph as illustrated in FIG. 26.

The statistical method generates the most consistent contrast performance curves. However, the statistical method tends to bias all results toward higher contrast measures and it cannot generate accurate contrast measures when non-linear or iterative reconstruction is used.

The "Rose criterion" has long been a robust standard for image detectability analysis of low contrast objects embedded in a white noise background. The Rose Criterion Derivation is another prior art method suitable for use in some embodiments of the present invention. The Rose Criterion Derivation relates object size, measured object contrast, and background noise (i.e., pixel standard deviation) in a formula that establishes a detectability index v written as:

$$v = \frac{Cp}{\sigma} \times \frac{\sqrt{\pi}}{2S} \quad (20)$$

where C is the measured object contrast,
p is the pin diameter,
S is the image pixel size, and
σ is the measured standard deviation of the background noise.

Note that in equation (20), the measured contrast level is indicated with an upper case C, differentiating it from the nominal contrast level of Equation (10), indicated with a lower case c.

Figure 27:
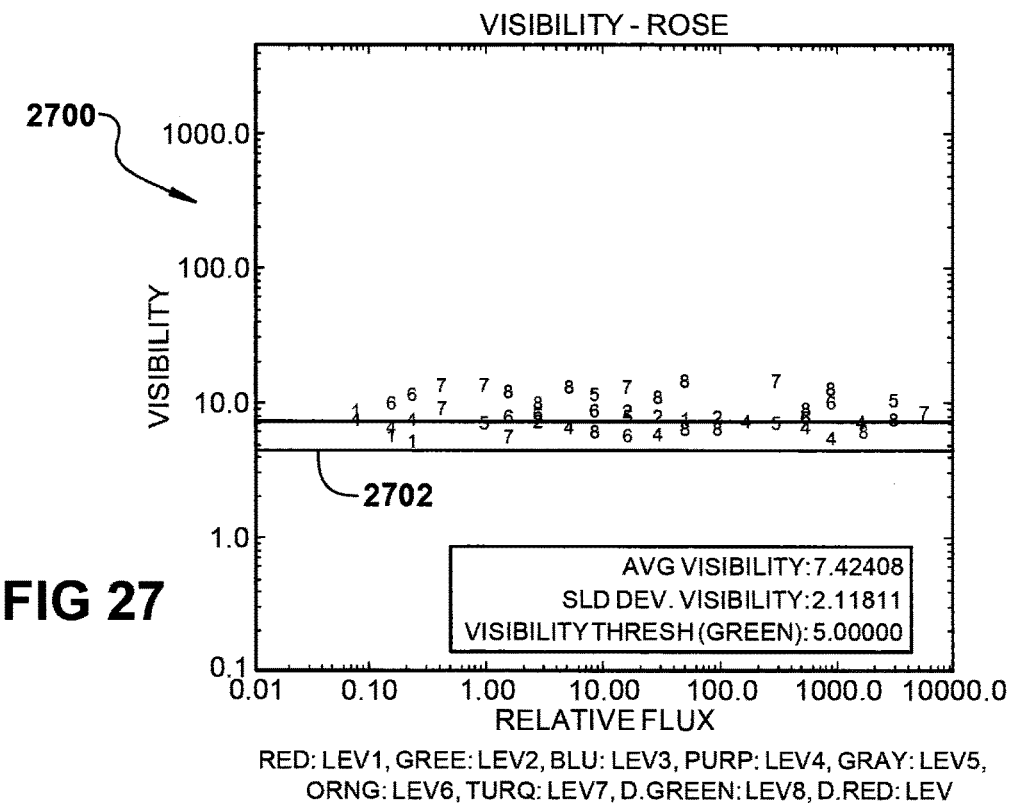
FIG. 27 is a plot of selected detectability values for a Rose Criterion visibility index.
Figure 28:
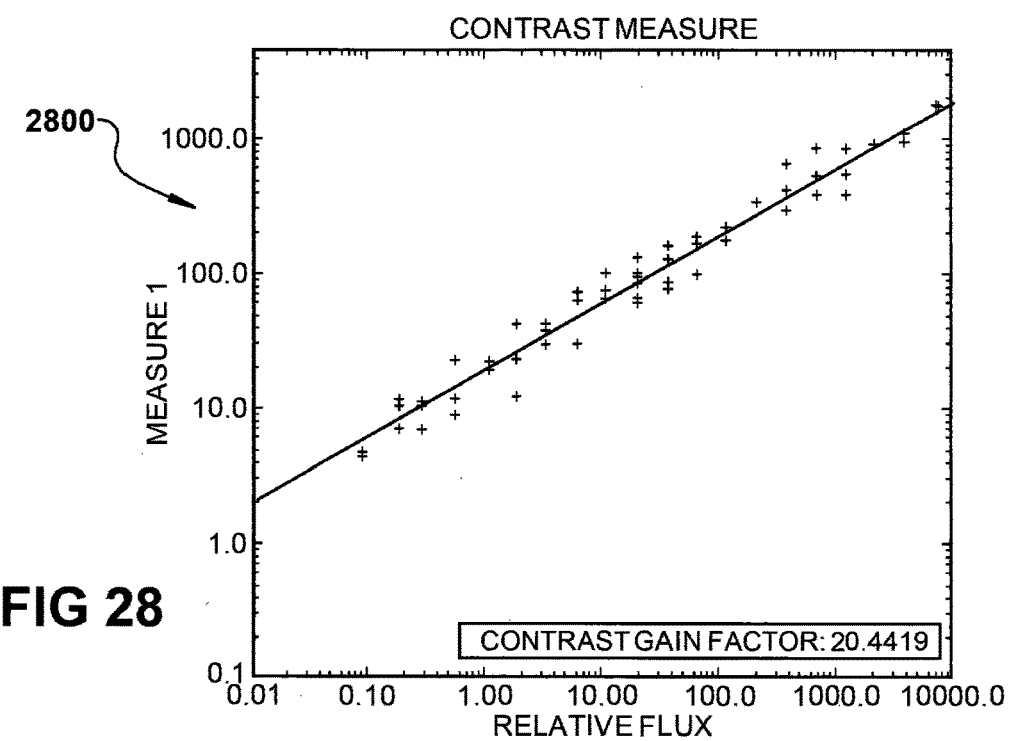
FIG. 28 is a plot of an ExLCD contrast index corresponding to the plot of FIG. 27.

Detectability values are computed for each of the contrast levels for each of the 44 image slices available in this example embodiment. The detectability values that are at or above the detectability threshold are flagged as "detectable." Although known Rose Criterion derivations suggest a threshold of 4, we have determined that a threshold of 5 is more consistent with human observer results. The selected detectability values are shown in plot 2700 of FIG. 27. For each detectable pin, an ExLCD Contrast Index value is determined and that value is plotted as shown on ExLCD contrast measure graph 2800 shown in FIG. 28.

Known Rose criterion definitions rely on measured contrast to determine a detectability index. However, we have investigated the behavior of the Rose detectability method when ideal or nominal contrast is used instead of the measured contrast. We have found that such a Rose-Ideal detectability index can then be written (note the use of the lower case c):

$$v_I = \frac{cp}{\sigma} \times \frac{\sqrt{\pi}}{2S} \quad (21)$$

The Matched Filter detectability method relies upon a formulation for an Ideal Bayesian Observer (IBO). An ideal observer is one whose data analysis performance is the highest possible. The Matched Filter detectability method uses a formulation of the IBO ideal decision maker written as $$SNR^2 = K^2 \int \frac{|f(\tau)|^2 MTF^2(\tau)}{W_n(\tau)} d\tau, \quad (22)$$

where f is the Fourier transform of the ideal object,
K is the large area transfer factor,
MTF is the system Modulation Transfer Function (MTF), and
$W_n$ is the noise power spectrum.

In Equation (22), the term $|f(\tau)|^2 MTF^2(\tau)$ is effectively the power spectrum of the reconstructed object with no noise. This formulation works for a linear, shift-invariant system but may not be adequate for modeling non-linear reconstruction methods. In order to generalize Equation (22) for the non-linear case, we replace the term $|f(\tau)|^2 MTF^2(\tau)$ with $|\hat{f}_o(\tau)|^2$, the power spectrum of the object-dependent reconstruction of an ideal object, o.

Thus, $$SNR_o^2 = K^2 \int \frac{\left|\hat{f}_o(\tau)\right|^2}{W_n(\tau)} d\tau \quad (23)$$

and the Matched Filter detectability index, $v_o$, is written $$v_o = SNR_o = K \sqrt{\int \frac{\left|\hat{f}_o(\tau)\right|^2}{W_o(\tau)} d\tau}. \quad (24)$$

The object, o, is "visible" if $v_o$ is greater than a predetermined threshold. The NPWMF and NPWEFMF are examples of matched filters, the latter incorporating an additional term modeling frequency response of the human eye.

FIG. 29 is an illustration representing the Matched Filter method, using images and graphics as illustration aids. A reconstructed image noise field 2902 is convolved with an ideal reconstructed image 2904 of a pin to produce a filtered noise field 2906. A sequence 2908 of (for example) fifteen ideal reconstructed pins is combined with the filtered noise field 2906 to produce an image 2910. Image 2910 is used to determine a contrast amplitude necessary to achieve detectability above a specified threshold.

Computing $v_o$ uses an overall constant K that is implicit in some embodiments of our ExLCD process. Constant K does not vary with the CT scanner used for imaging, but is used to force numbers into a computationally convenient range so that they may be manipulated efficiently by computational hardware and software (such as computers and/or special modules) that are used or that comprise some embodiments of the present invention. The noise power spectrum, $W_n$, is computed as a radial average of the 2D Fourier transform of a large uniform noise region of pixels. This region should be highly uniform and is preferably free from even minor cupping, bands or rings. The result is scaled appropriately for pixel size and number of pixels.

The object-dependent Fourier transform of the object, $|\hat{f}_0(\tau)|^2$, is computed as a radial average of the 2D Fourier transform of the reconstructed object. The small region of pixels containing the object is preferably selected to reduce noise contamination. As with the noise power spectrum, the result is preferably scaled appropriately for pixel size and number of pixels.

EXLCD Performance Function

Figure 30:
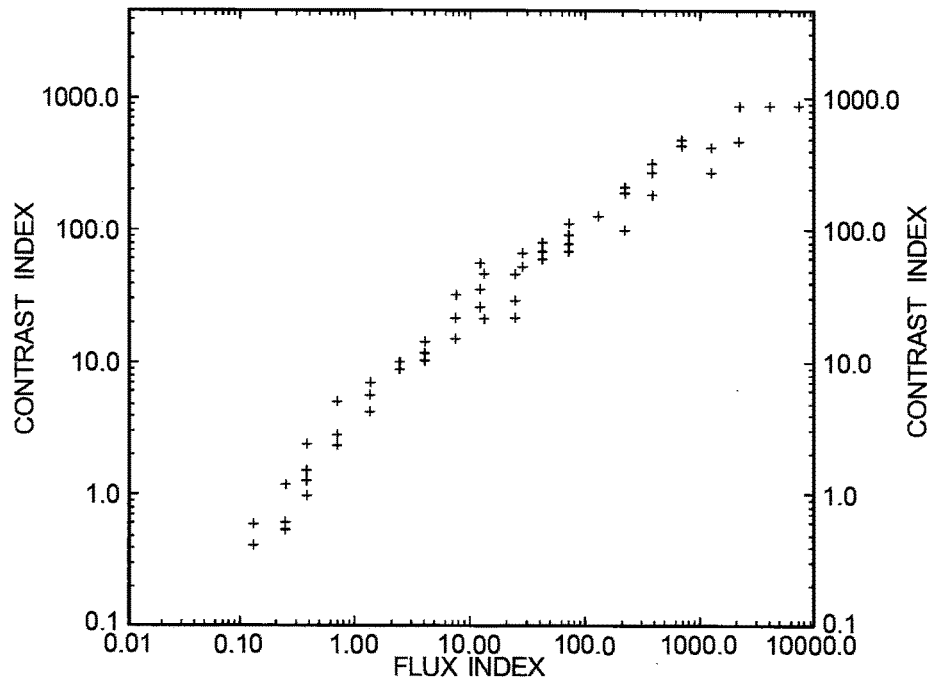
FIG. 30 is a plot showing order pairs of [Flux Index, Contrast Index].
Figure 31:
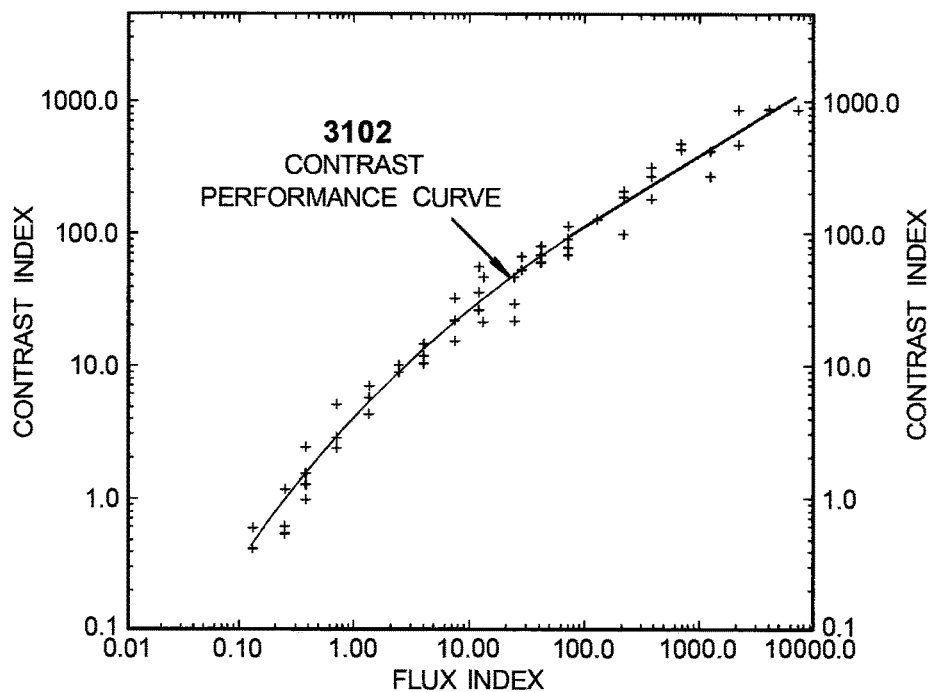
FIG. 31 is a contrast performance curve generated in one embodiment by a regression fit to a 2-parameter equation.

As described above, the output of any of the detectability methods applied to the 44 image slices in some of the example embodiments is a collection of ordered pairs [Flux Index, Contrast Index] that correspond to the smallest pins that are "detectable" for applicable contrast levels. In some embodiments of the present invention, this collection of ordered pairs can be plotted on a log-log scale as shown FIG. 30 and then used to build the ExLCD Performance Function. Data points are then fit to a 2-parameter equation that includes quantum detection efficiency and system/electronic noise. As an example, FIG. 31 illustrates a contrast performance curve 3102 generated in one embodiment by a least-squares fit.

In the absence of non-linear reconstruction methods, it can be shown that the ExLCD Contrast Index is approximately proportional to signal-to-noise using a relationship written as $$M \cong K \times \frac{\rho J}{\sqrt{\rho J + \sigma_e^2}}, \quad (25)$$

where [J, M] represent the ordered pairs, [Flux Index, Contrast Index],
$\rho$ corresponds to the Contrast Gain Factor, and
$\sigma_e$ corresponds to the standard deviation of the system/electronic noise.

In some embodiments, for each collection of ordered pairs, values for $\rho$ and e are determined that best fit the measured ordered pairs.

In some embodiments of the present invention, parameters $\rho$ and $\sigma_e$ provide a definitive characterization of a CT scanner. To illustrate this definitive characterization, the Results and Experiments section includes results showing how different detectability methods react to specific scanner changes that affect $\rho$ and $\sigma_e$.

Figure 32:
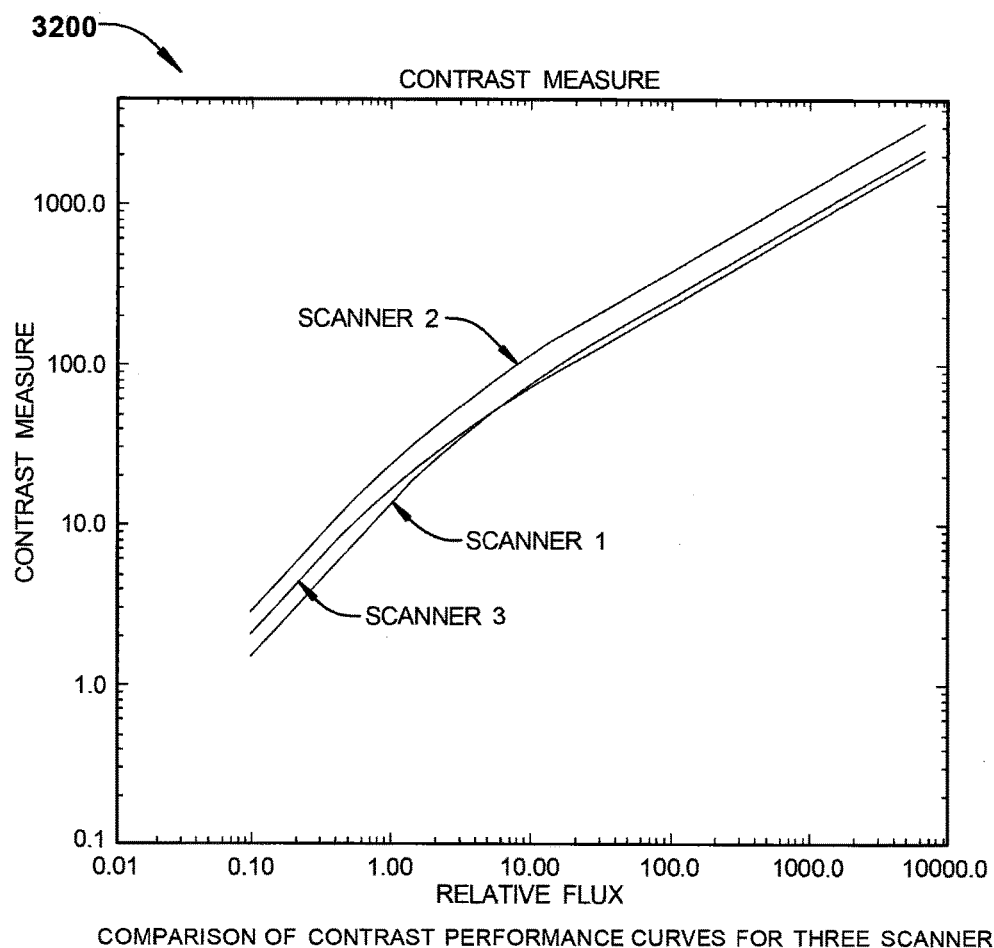
FIG. 32 is a plot showing the comparison of contrast performance curves for three scanners.

A scanner has better performance when the ExLCD process reports higher values for contrast gain and lower values for electronic noise. For example, comparison plot 3200 of FIG. 32 shows that Scanner 2 has a higher (better) contrast gain than Scanner 1, Scanner 3 has a somewhat lower (worse) contrast gain than Scanner 2, and Scanner 3 has lower (better) electronic noise than Scanner 1.

Referring now to FIGS. 33 and 34, when a smaller pin is blurred by the system MTF, there may be a corresponding reduction of contrast. That is, a highly filtered noise spectrum with a highly filtered object results in a lower detectability score than a reconstruction process (e.g. non-linear reconstruction) that results in a highly filtered noise spectrum but which is capable of retaining the spatial geometry of the original object. This phenomenon is typically observable and measurable only for the smaller contrast pins.

Figure 35:
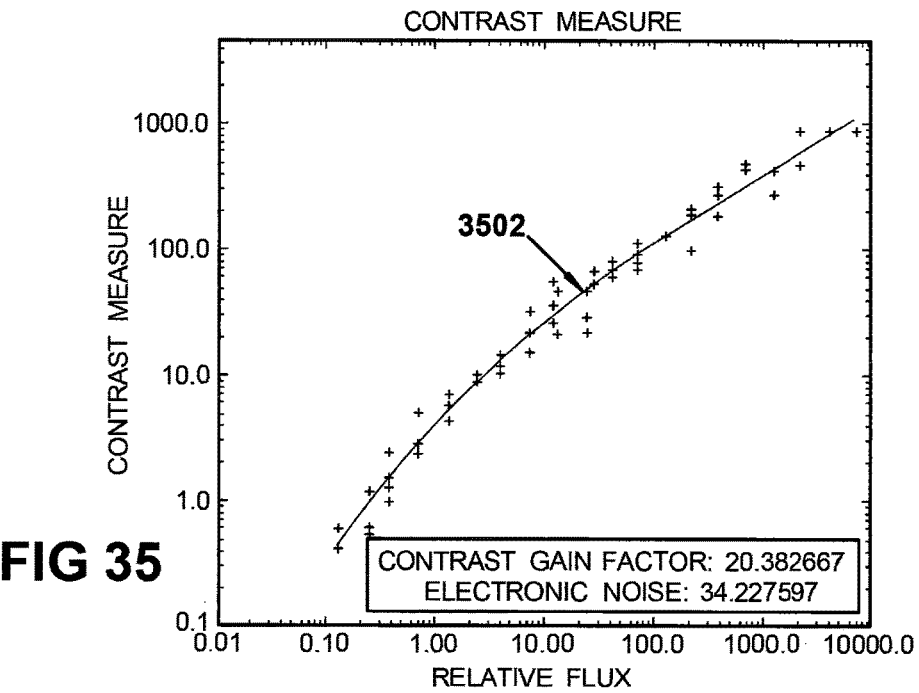
FIG. 35 is a graph showing a large pin contrast curve (pins >2.5 mm).
Figure 36:
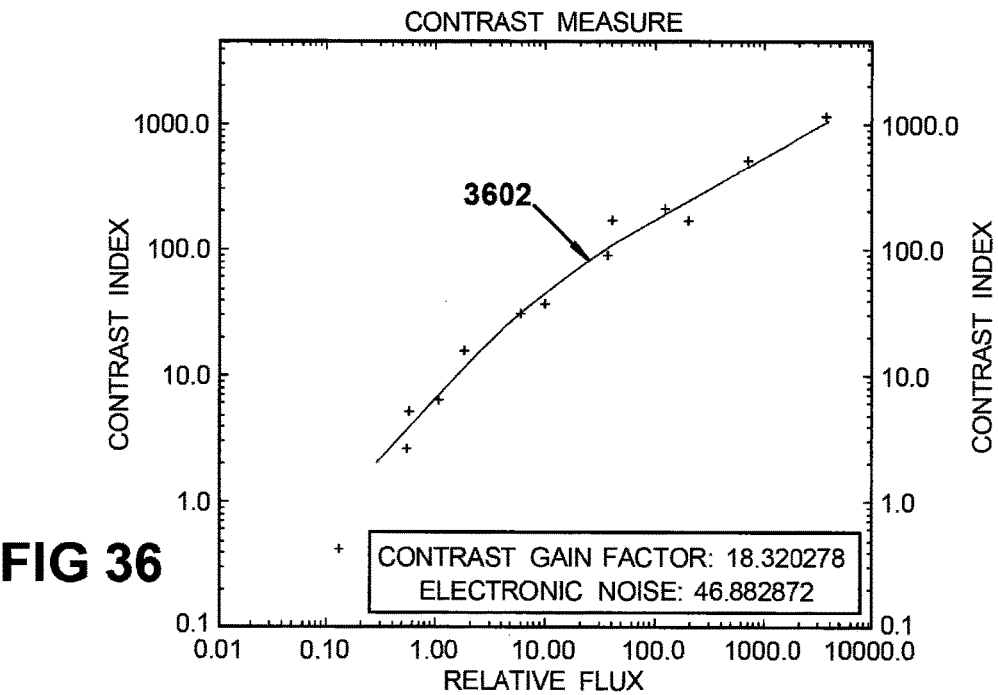
FIG. 36 is a graph showing small pin contrast performance curves (pins of 2.5 mm and 2 mm).

Therefore, in some embodiments, the ExLCD method uses a small pin performance curve, estimated from the contrast measurements involving the pins that are impacted by the MTF. Referring now to FIGS. 35 and 36, contrast measures 3502 and 3602 are shown for large pins (upper) and small pins (lower), respectively. A comparison of the contrast performance curves for a large pin vs. a small pin is shown in FIG. 36.

Phantom Calibration

Physical ExLCD phantoms will have some engineering variability that will cause each of them to deviate somewhat from an ideal phantom design. Therefore, in some embodiments of the present invention, the ExLCD process compensates for this variability by incorporating a calibration component that determines and records actual contrast values and actual pin location values. The actual contrast values, determined by the calibration, are then used as the nominal contrast values c for all ExLCD measurements in that embodiment. The use of actual pin location values improves the accuracy of measured contrast values C for non-observer detectability determinations. Referring again to FIG. 5, in one phantom embodiment 300, there are large wedge shaped regions 502 of material to facilitate computation of actual contrast values.

The calibration component effectively compensates for x-ray spectral variations between scanners. Also, the calibration component includes a phantom manufacturing tolerance check. If the phantom slices are out of tolerance in contrast, pin size or pin locations, some embodiments of the present invention report the fact that the phantom slices are out of tolerance and/or the difference between the actual and nominal location values.

Some embodiments of the present invention use a Channelized Hotelling Observer (CHO) detectability metric. These metrics are used as an IQ goal to improve control of a radiographic imaging system and to minimize or at least reduce the problems listed above for IQ goals used in known radiographic imaging systems. In some embodiments of the present invention, ExLCD is incorporated into a CT AEC system. In yet other embodiments, ExLCD is used to obtain desired IQ goals by externally recommending required settings to use for patient scanning.

The user of a radiological imaging system such as a CT scanner selects a set of scan and reconstruction parameters, known as a protocol, for scanning a patient. The slice thickness, mAs settings and patient attenuation influence the amount of x-rays used to produce the image. Fewer x-rays increase noise and result in a poorer quality image. The quality of the image is also dependent on the selection of kVp, source filtration, collimation, and image reconstruction parameters. To characterize the performance of the scanner, a phantom with several diameters covering the typical range of patient sizes (a range of about a 10 cm to 45 cm water equivalent diameter) is needed in some embodiments. Referring again to FIGS. 3, 4, 5, and 6, each phantom 300 diameter section 302, 304, 306, 308 contains a set of low contrast objects such as rods 402, a uniform background region 602, and a set of large low contrast regions such as wedges 502. The low contrast values of the objects are chosen to be near the visual limit of detectability for the diameter in which the object is located. The low contrast values are increased for the larger diameter sections to account for the quantum noise increase with increasing attenuation. If phantom 300 is constructed using 3-dimensional printing methods, discrete diameters can be replaced by one or more conical sections where the object contrasts may also continuously increase with increasing effective conical diameter. Three-dimensional printing methods allow very complex phantoms 300 to be constructed. For example, anthropomorphic phantoms using CT images as input could be printed. This would allow CHO to be used to evaluate the detectability of realistic lesions in an anthropomorphic background instead of simple geometric objects in a uniform background.

Although phantom materials are chosen to be as energy independent as possible, the actual contrast of the objects will change depending on the effective energy of the imaging system. Ideally, the large low contrast regions should be made of the identical material as the low contrast objects to allow the contrast produced by the imaging system to be measured.

Figure 37:
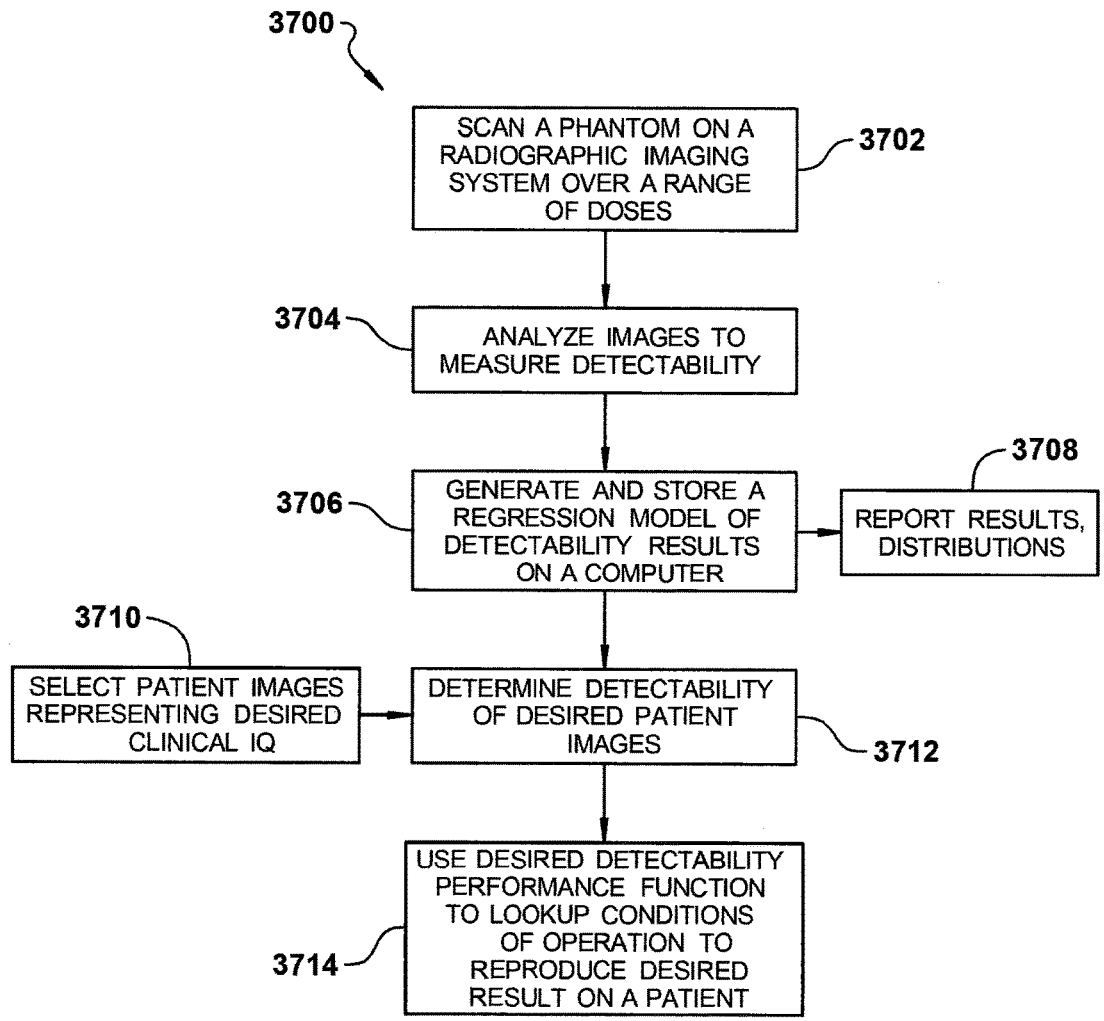
FIG. 37 is a flow chart illustrating the steps needed in one embodiment to convert desired CIQ into a protocol recommendation for a scanner.

In one embodiment and referring now to flowchart 3700 of FIG. 37, a phantom 300 is scanned at a range of doses for a core operating mode at block 3702. A core operating mode is the set of all conditions of operation except those typically used to control x-ray intensity such as mAs or an image quality goal for an auto exposure control (AEC) protocol. Scans are obtained at a sequence of different dose levels extending over the range of settings provided by the scanner. Scans are repeated to produce a sufficient number of images to train and evaluate scanner performance using a Channelized Hotelling model Observer (CHO). In some embodiments, about 300 object-present and 300 object-absent images for each object instance. An object instance is a unique object size, such as rod diameter, and contrast in the image.

In some embodiments, a Channelized Hotelling model Observer (CHO) module implemented in hardware or software or some combination thereof determines a signal to noise SNR for each object instance within phantom 300. CHO is considered to be the most advanced class of model observer. CHO is currently considered to be the model observer that is the most practical and accurate predictor of human performance in detecting an object {Myers 1987} {Barret 2004}. CHO produces an SNR and statistical distributions for object present and object absent trials. Hence, in addition to SNR, the object present and object absent distributions can be used to generate a Receiver Operating Characteristic (ROC) curve. The ROC curve is a plot of true positive fraction (TPF) vs false positive fraction (FPF). A typical measure for an ROC curve is the Area Under the Curve (AUC).

A regression model of detectability results from block 3704 is generated and stored by a computer or computational engine at block 3706. The results and/or distributions thereby obtained are reported to a human (e.g., by a display device or print-out) and/or stored in memory and/or a digital medium (such as a CD, DVD, RAM, or ROM) at block 3708. Patient images representing a desired clinical image quality (IQ) are selected at block 3710, and, in conjunction with the regression model of detectability results obtained at block 3706, the detectability of desired patient images is determined at block 3712. A desired detectability performance measurement function so obtained is then used at block 3714 to look up and set (in some embodiments, automatically via electronic circuitry) conditions of operation to produce a desired result on a patient.

Figure 38:
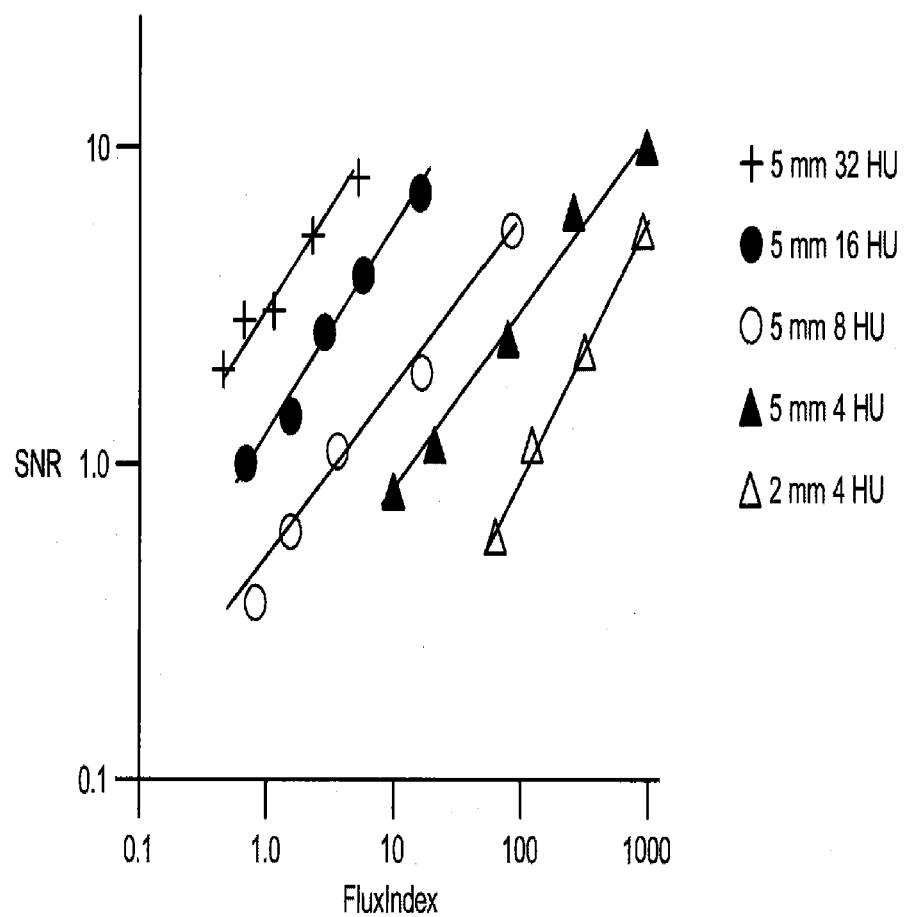
FIG. 38 is a plot of a Channelized Hotelling Observer output of signal to noise performance for each instance of a pin size and contrast for an example phantom.
Figure 39:
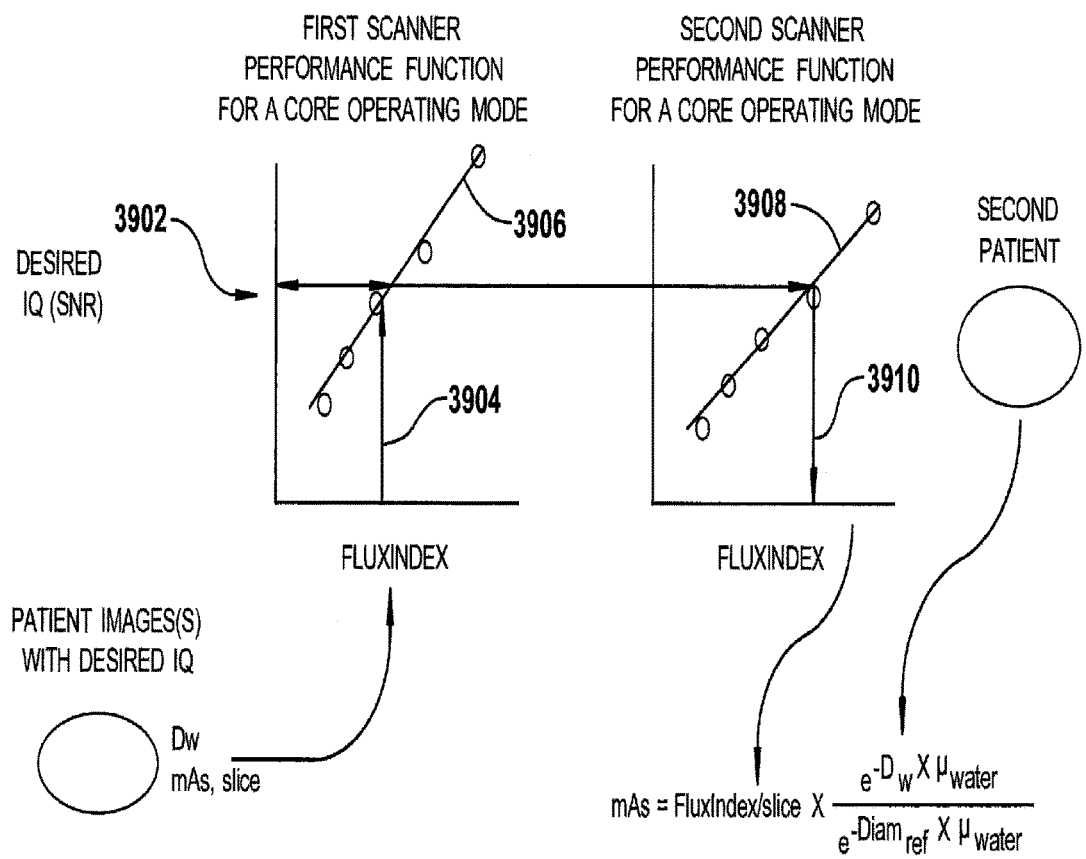
FIG. 39 is a schematic chart showing how image quality results are replicated between more than one scanner.

As shown in FIG. 38, CHO provides an output of Signal to Noise performance for each instance of pin size and contrast. The SNR results from a model observer method, such as CHO, is a set of discrete values as a function of FluxIndex for each object instance. In some embodiments, CHO is provided as a hardware or software module that performs the CHO model observer method. An interpolation (for example, by a regression model) of the SNR results in a function of FluxIndex, for example, provides a continuum of results (an ExLCD performance function) that represent the SNR performance of a scanner and/or allows image quality results to be duplicated on another scanner. Referring now to FIG. 39, the desired patient CIQ (SNR) 3902 is determined from patient images or by statistical methods of reviewing distributions of patient CIQ results. Typically the desired CIQ is a function of patient size. The patient size in terms of a water equivalent diameter $D_{weq}$ is determined for the patient image {Menke 2005} and the conditions of operation from a DICOM header determine the FluxIndex 3904 of a first scanner performance function 3906 for a core operating mode, which in turn defines the SNR value from the performance function of the first scanner on which the patient images with the desired CIQ were obtained. Using the performance function 3908 from a second scanner, the desired SNR and patient $D_{weq}$ indicate the desired mAs 3910.

Figure 40:
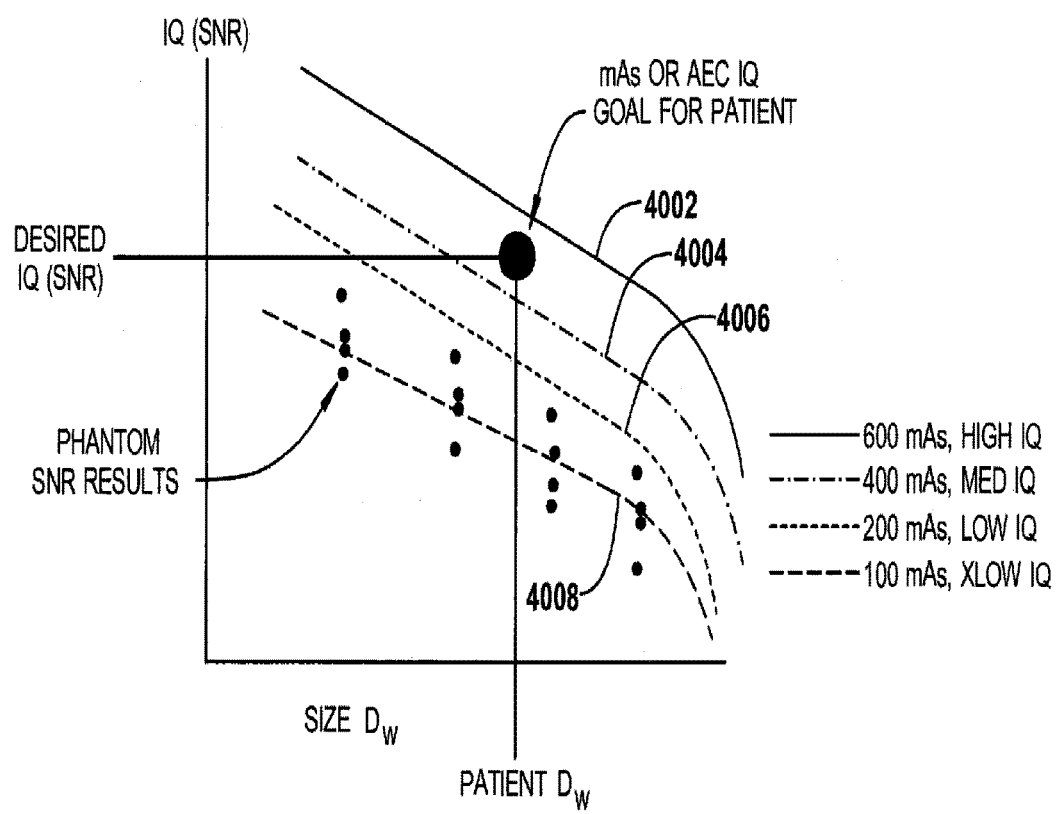
FIG. 40 is a graph of a family of performance functions for an automatic exposure control mode of a CT scanner.

Performance functions for a scanner using an auto exposure control (AEC) mode are determined in a similar manner but are organized as a collection of performance functions 4002, 4004, 4006, 4008 vs. patient size as shown in FIG. 40.

Several methods for mapping the SNR performance functions from a model observer such as CHO are discussed in the following. SNR performance functions for each object instance can be mapped directly, as an aggregate one-dimensional SNR performance function, or converted to a contrast index for use in ExLCD.

Method 1—Direct Mapping of Multiple SNR Instance Functions

Figure 41:
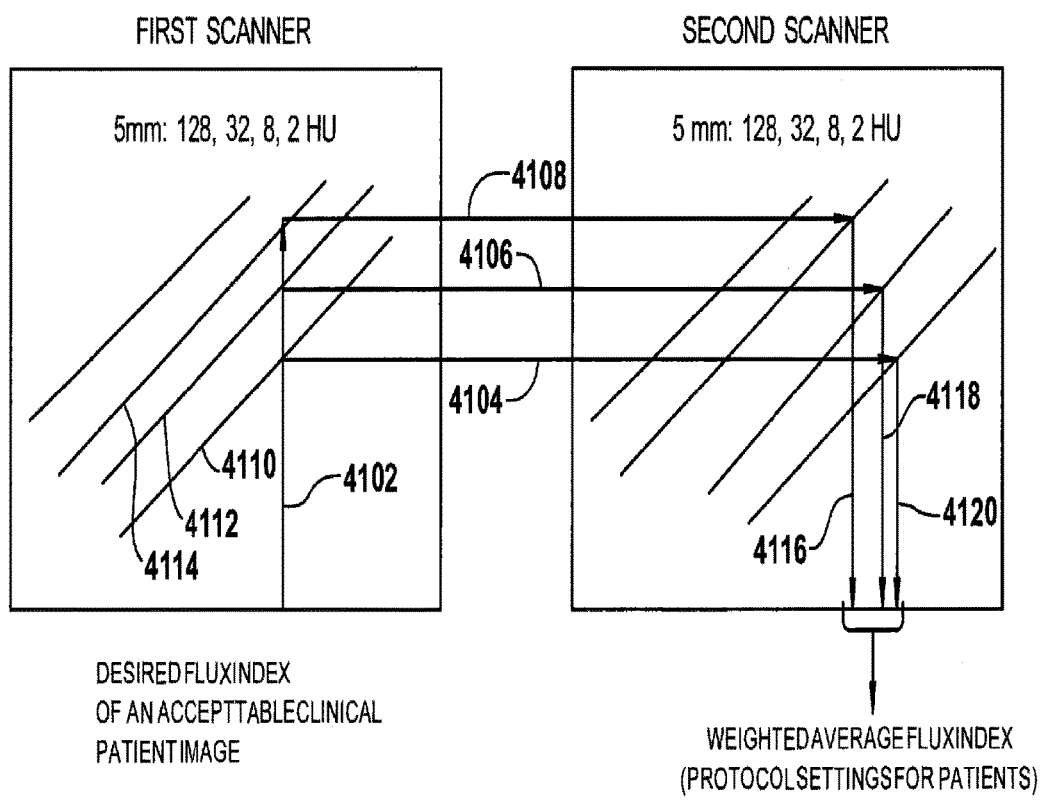
FIG. 41 is a schematic representation of an embodiment in which a collection of SNR values for a first scanner are translated to a second, different scanner and an associated collection of FluxIndex values are combined to provide a desired FluxIndex and associated protocol settings for scanning a patient.

Referring now to FIG. 38, individual SNR performance functions for each object instance comprise an embodiment of scanner characterization. A desired FluxIndex and associated SNR values of a first scanner in the example of FIG. 38 are calculated by a computing engine or module (for example), using the patient $D_{weq}$ and scanner settings of the clinical patient images that were determined to be clinically acceptable. Referring now to FIG. 41, the desired FluxIndex 4102 on the first scanner intersects a collection of SNR values 4104, 4106, 4108 on performance functions 4110, 4112, and 4114, respectively, of the first scanner. The collection of SNR values for the first scanner are translated to the second, different scanner and the associated collection of FluxIndex values 4116, 4118, and 4116, respectively, are combined (for example, by using a weighted average) to provide the desired FluxIndex and associated protocol settings for scanning a patient.

The weighting of members of the collection is dependent on the diagnostic task. For example, if the task is to look for liver lesions, the SNR values of the lower contrast pins having a diameter similar to lesions of diagnostic interest would be selected or weighted stronger than the SNR for objects less relevant to the diagnostic task. Another diagnostic task requiring higher spatial resolution might have increased weighting for the smaller diameter pins. The appropriate weightings could be determined by skilled radiologists.

Method 2—Mapping an Aggregate SNR Function

Figure 42:
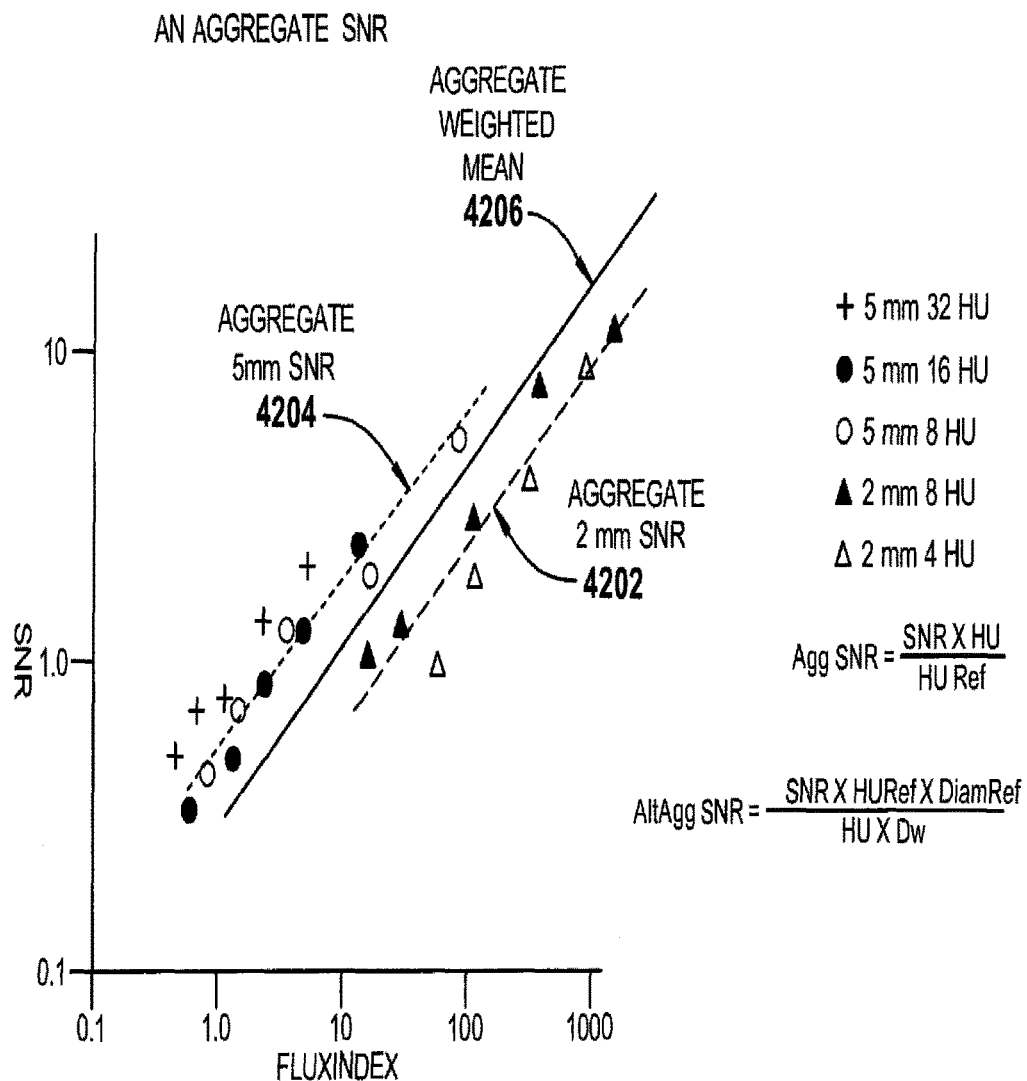
FIG. 42 is a drawing of a graph indicating how an aggregate SNR function is generated.

In one embodiment and referring now to FIG. 42, an aggregate SNR function is generated. A reference contrast is selected such as 8 HU. Each instance SNR is adjusted by the ratio of the reference contrast relative to the contrast of the object instance. A combination (for example, a weighted mean) of resulting SNRs for the different object diameters is determined to provide one-dimensional SNR performance functions 4202, 4204, using a suitable computer or computing engine. An alternative is to adjust each instance SNR by the ratio of a reference object diameter times a reference contrast divided by the product of the object instance diameter times its contrast. An aggregate weighted mean function 4206 is generated in some embodiments.

Method 3—Mapping SNR to a Contrast Index Using an Object Present Threshold

Figure 43:
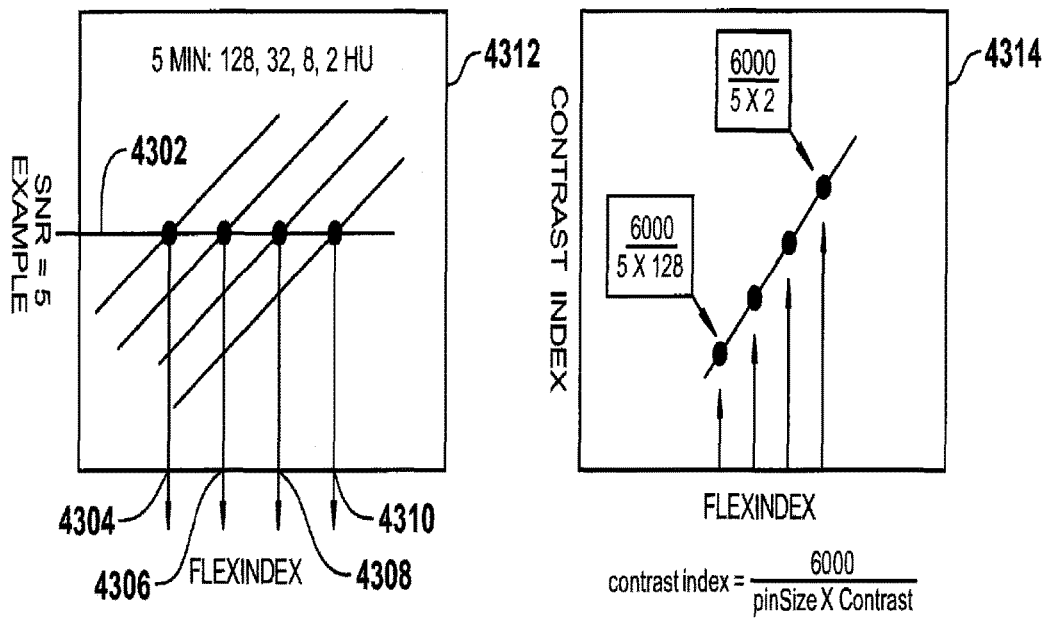
FIG. 43 is a schematic representation of an embodiment in which combinations of multiple object instances are used to find a FluxIndex required for each pin contrast in order to achieve a specified SNR.

In some embodiments and referring now to FIG. 43, combinations (for example, made by regression models) of multiple object instances are used to find a FluxIndex required for each pin contrast in order to achieve a specified SNR. For example, an SNR value of 5 is chosen as a detectability threshold 4302 and 5 mm diameter pins are selected. The associated FluxIndex values 4304, 4306, 4308, 4310 required to produce that SNR for each contrast are determined from plot 4312. FluxIndex values for an SNR value of 5, and the pin contrast and diameters are then used to determine the contrast index at each FluxIndex 4304, 4306, 4308, 4310 FluxIndex as shown in plot 4314. For example, referring to plot 4312, the 5 mm, 128 HU pin requires a FluxIndex of 10 for an SNR of 5. Plot 4314 is then used to find the contrast index of 9.375 (6000/5×128) at the FluxIndex of 10. This is done for all of the other pins to obtain a set of points describing the FluxIndex needed for each object to achieve an SNR of 5. In some embodiments, combinations of these data (for example, made by a regression model) are computed to describe the contrast index vs. FluxIndex for a given diameter pin, 5 mm for example, as shown in plot 4314.

Figure 44:
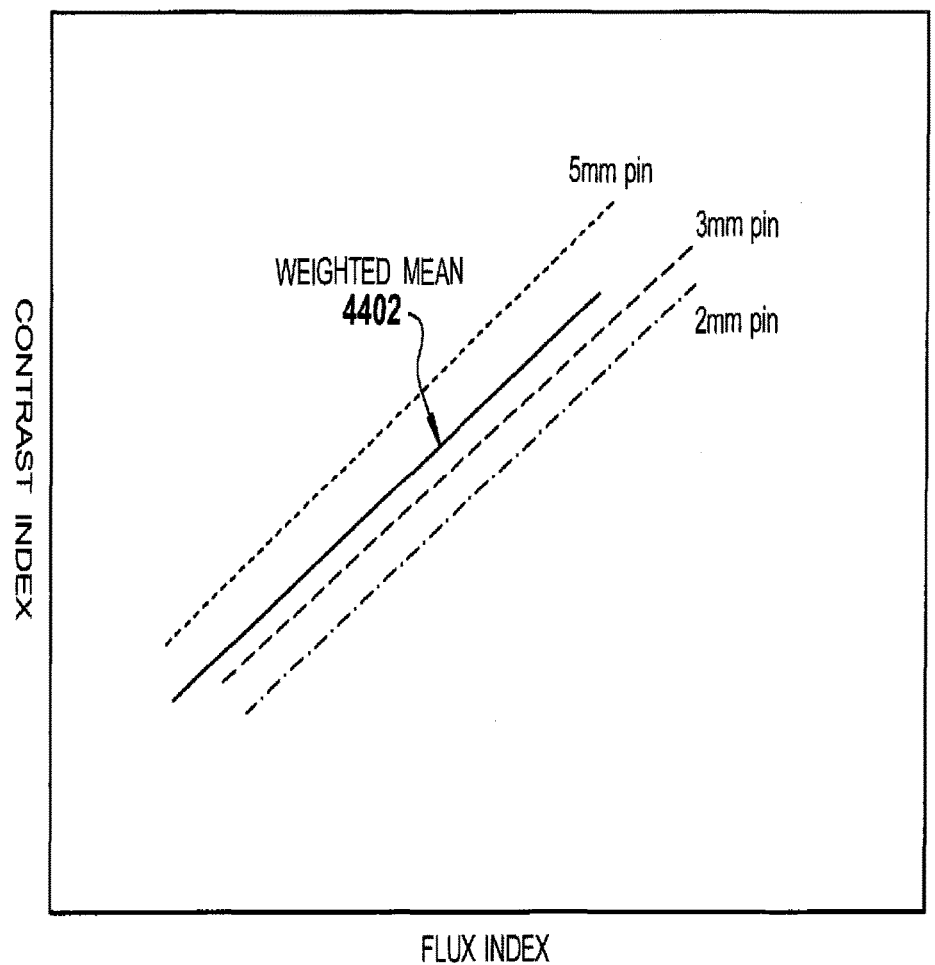
FIG. 44 is a graph representing an embodiment in which multiple pin diameters are analyzed using CHO, mapped to a Contrast Index and combined using a weighted mean.

In some embodiments and referring to FIG. 44, this process is done for all pin diameters, and a combination (for example, a weighted mean) of the different pin diameter contrast index functions is used to define a single contrast index function 4402 for guiding clinical practice as described elsewhere herein.

Method 4—Mapping SNR to a Contrast Index using an ROC Curve

Figure 45:
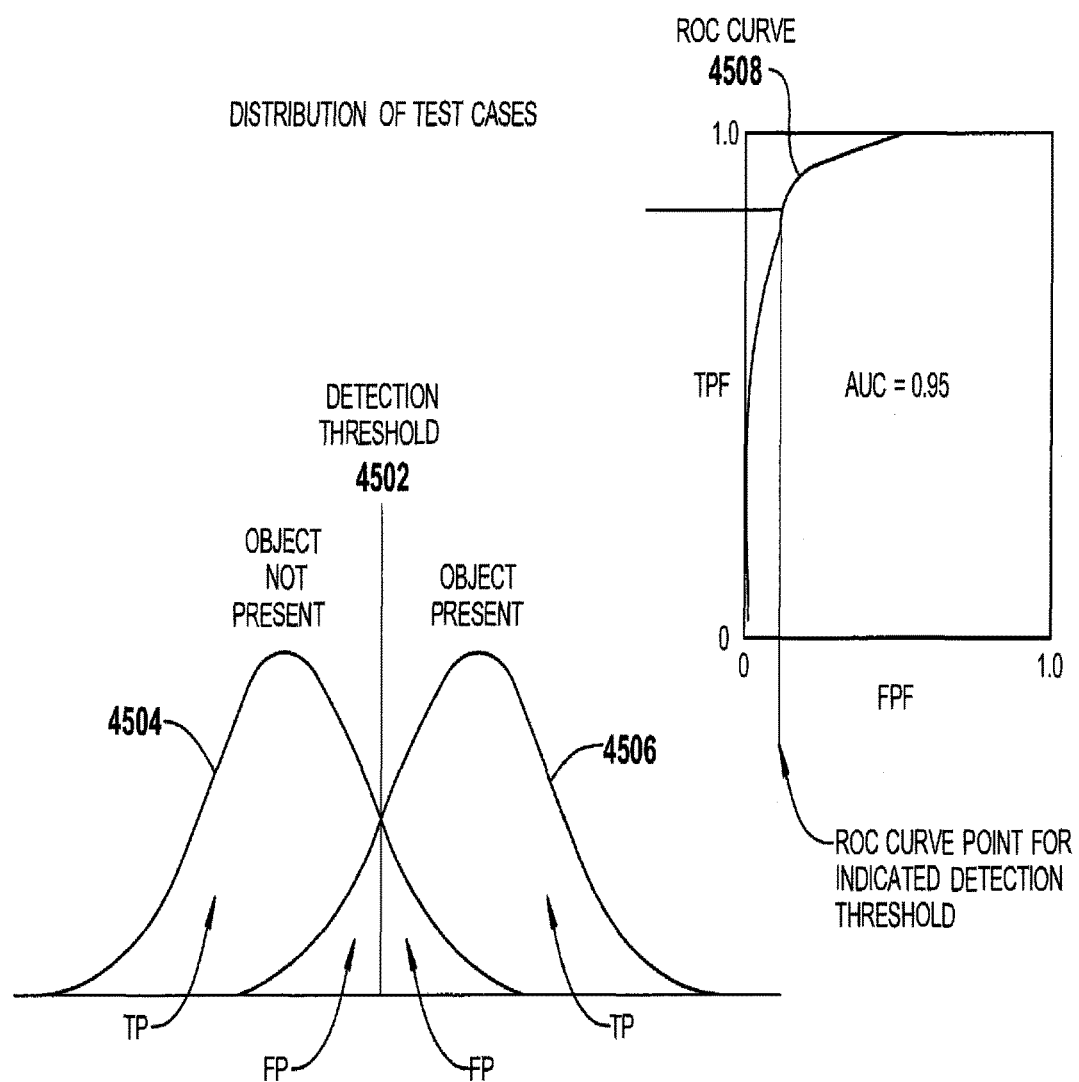
FIG. 45 is a graphical representation of an embodiment in which statistical distribution information from a CHO ROC curve is used to determine detectability.

Referring now to FIG. 45, instead of arbitrarily selecting an SNR detection threshold, some embodiments of ExLCD applications use statistical distribution information from a CHO ROC curve 4508 to determine detectability. For example, a smallest detectable pin is selected from the set of pins at a given FluxIndex. To define an object as detectable, some embodiments use a desired AUC threshold, for example, AUC>0.95 above which an object is deemed detectable. This definition is possible because CHO provides distribution information 4504, 4506 as well as the SNR to allow the AUC to be calculated from the ROC curve 4508 of each pin. This embodiment is especially useful in at least some instances in which the probability distribution functions both with and without object present are non-normal as a result of an iterative reconstruction process, for example.

Presentation of SNR Information for Comparing Scanners and Operating Modes

Data from a CHO analysis can also be presented in a variety of ways as indicated in FIG. 46 to allow a comprehensive comparison of the detectability performance of different scanners and operating modes. For example, the SNR for a given size object as a function of FluxIndex in FIG. 38 is given as a function of mAs at a specified $D_{weq}$, $D_{weq}$ at a specified mAs, as shown in plot 4602.

Since CTDIvol (the standard CT Dose Index) is associated with mAs for the core operating mode, CTDIvol can be substituted for mAs, allowing SNR to be presented, as shown in plot 4604 as a function of:

CTDIvol at a specified $D_{weq}$,
$D_{weq}$ at a specified CTDIvol.
Other possible presentations are
CTDIvol vs. $D_{weq}$ at a specified SNR,
mAs vs. $D_{weq}$ at a specified SNR.

These and other presentations of the CHO data can provide previously unknowable insight into performance of scanner features and capabilities. Generating CHO data and organizing it in various ways to provide a continuum (for example, using regression functions) allows this unique probing of the IQM vs. dose performance of radiographic imaging devices, such as a CT scanner.

Incorporation of ExLCD in an Auto Exposure Control (AEC) System

ExLCD can be incorporated into a CT scanner AEC system and thereby use the ExLCD contrast index as the image quality goal to guide clinical practice. While current AEC system IQ goals are relative IQ models restricted to a scanner make or model (such as noise standard deviation, quality effective mAs or a reference image), ExLCD is universal and eliminates the confusion of different manufacturer's parameters for controlling AEC. ExLCD also allows a clinical database of contrast index values determined as standard of care by a large number of clinicians to be employed on any scanner with an ExLCD characterization.

Since the asymmetry ratio (AR) is determined, ExLCD could also be used to control the angular modulation in an AEC system.

Using ExLCD on a Scanner with an Existing AEC System

In some embodiments and referring again to FIG. 40, ExLCD can also be adapted to provide contrast index results for an existing AEC system. As shown in FIG. 40, contrast index functions 4002, 4004, 4006, 4008 are measured and obtained as a function of the ExLCD phantom water equivalent diameter for a set of Image quality goal parameters provided by the CT AEC system. When scanning patients, the desired contrast index for the diagnostic task and patient size ($D_{weq}$) identify the appropriate AEC IQ goal to use for scanning the patient.

Figure 48:
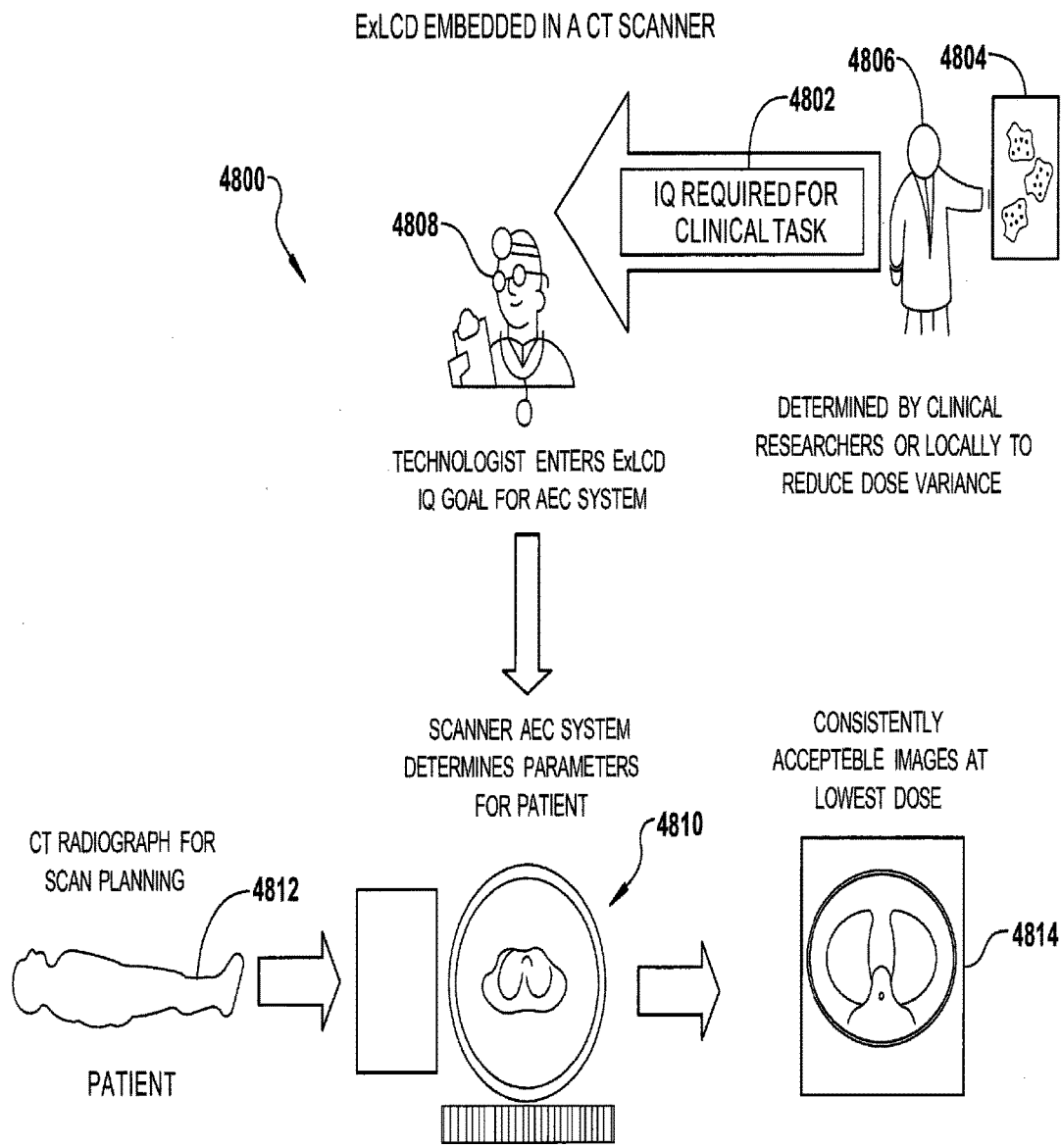
FIG. 48 is a graphical flowchart of an ExLCD embodiment in which CHO is embedded in a CT scanner.

In some embodiments and referring to flowchart 4800 of FIG. 48, ExLCD is embedded in modules in a CT scanner. An IQM 4706 corresponding to the CIQ required for a selected clinical task 4804 is determined by clinical researchers 4806 or locally to reduce dose variance. IQM 4706 is given to a technologist 4808 who enters the ExLCD goal 4706 for a scanning system 4810 having automatic exposure control. The AEC system of scanner 4810 then determines parameters with which to perform a scan of patient 4812. Scanner 4810 and its AEC system thus produce consistently acceptable images 4814 at a low (or even at the lowest possible) dose consistent with producing an image suitable for the selected clinical task 4804.

Figure 49:
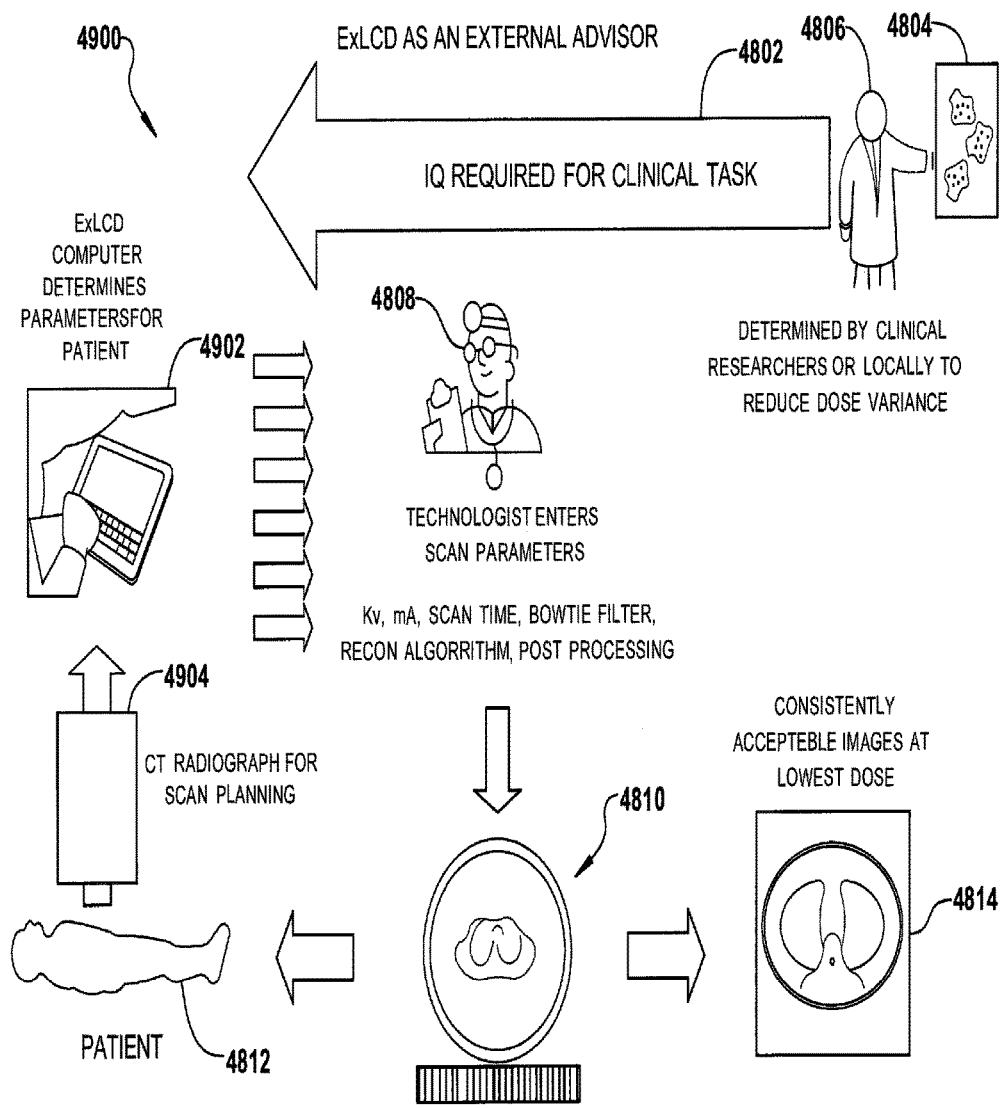
FIG. 49 is a graphical flowchart of an ExLCD embodiment in which ExLCD is provided as an external advisor to a CT scanner.

In some embodiments and referring now to flowchart 4900 of FIG. 49, ExLCD is provided as an external advisor to CT scanner 4810. Differences between these embodiments and those represented by FIG. 48 (which embodiments are not necessarily exclusive of one another; i.e., an embodiment can have both embedded ExLCD and external ExLCD) include that IQs 4802 in the embodiments represented by FIG. 49 are sent or entered into an external computer or computational engine 4902. Also, CT radiographs 4904 may be sent or entered to computer or computational engine 4902 for scan planning. Scan parameters, including one or more provided by computer or computational engine 4902 are sent to (or read by) technologist 4808 who then enters these scan parameters directly into scanner 4810 rather than entering an ExLCD IQ goal. Examples of such parameters include Kv, scan time, bowtie filter, reconstruction algorithm, and post-processing algorithm.

Although computer 4902 is shown as a handheld touchscreen device in FIG. 49, many other types of computers are suitable for use in various embodiments and more generally throughout the various embodiments of inventions described herein. For example, with regard to computer 4902 shown here, a desktop or laptop computer is also suitable, as well as special purpose computers and single purpose computers. The computers need not be portable and also can include computers with physical and/or software security.

More generally, it is a design choice whether, in any particular embodiment, a computer or computer engine is a separate entity from a scanner, included within the scanner, or a separate module or modules that are or are not located within a scanner.

One of ordinary skill in the art will thus appreciate that some embodiments of the ExLCD process are capable of successfully characterizing the contrast performance of a CT scanner over its entire flux range. Also, ExLCD processes are adaptable to other radiography applications such as digital radiography, mammography, nuclear medicine and SPECT.

In at least one known LCD process, a single LCD measurement provides no information about the contrast performance of a scanner in the lower flux regions including (1) body scans at lower dose, (2) scans for a large body, and (3) fast scans.

One of ordinary skill in the art will now appreciate that, without the ExLCD process, human observer detectability determination is less consistent than either of the automatic methods, namely, statistical and Rose. In fact, observer detectability determination, by itself, is not accurate enough to differentiate the contrast performance among typical commercial scanners.

It will further be appreciated by those skilled in the art that various apparatus and method embodiments of the present invention provide a performance function for a radiographic imaging system (such as CT) that characterizes detectability over the operating range of the system. In some embodiments, a performance function is provided that can be associated with clinical performance related to dose utilization.

The ExLCD embodiments described herein are particularly adapted for automated forms of implementation. For example, ExLCD methods may be implemented using a general purpose computer or by a specially designed apparatus. The use of a specially designed apparatus is preferred, in that a specially designed apparatus can provide greater security in, for example, a clinical setting as well as simplified controls for a technician to operate and the ability to control a plurality of scanners to provide consistently acceptable images at low doses.

Some methods and apparatus embodiments of the present invention are also useful in conjunction with non-linear and iterative image reconstruction methods.

A special phantom or set of phantoms can be used with a large array of objects of various sizes and contrasts designed to cover the range of lowest to highest possible flux conditions.

Figure 47:
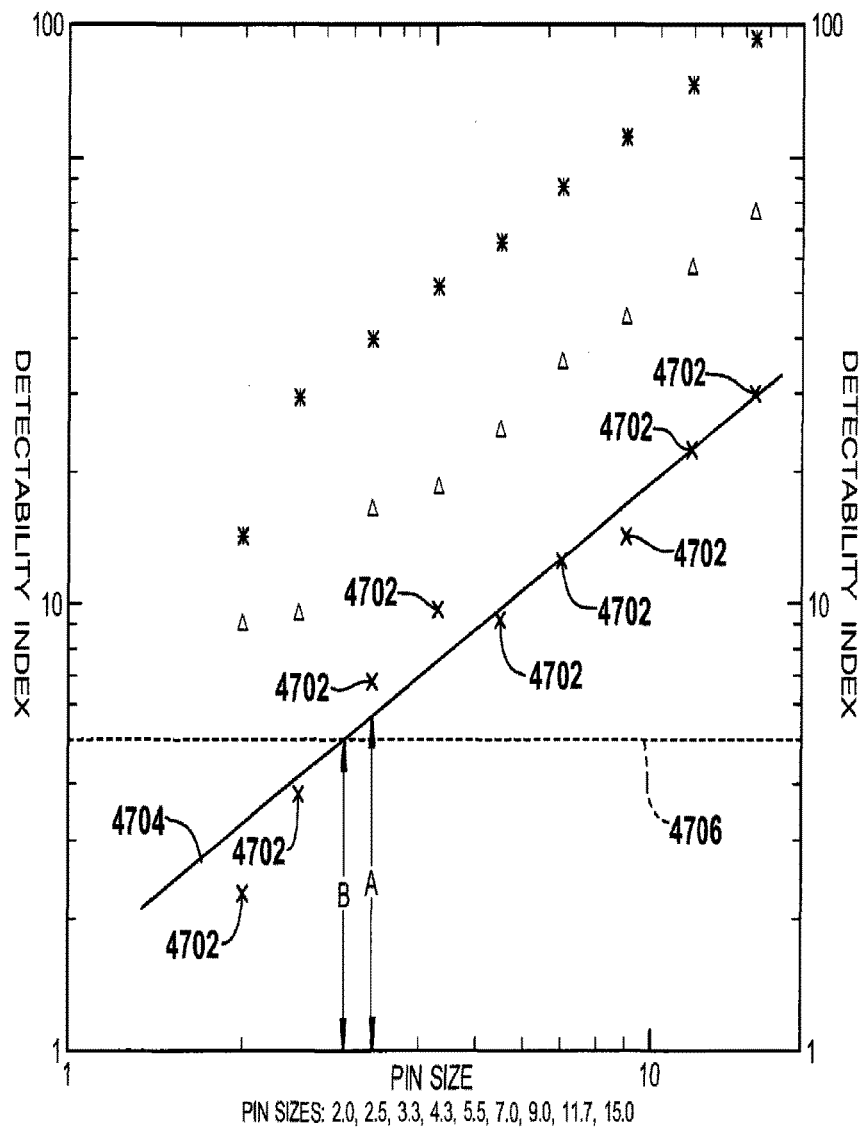
FIG. 47 is a graph illustrating that embodiments of ExLCD methods and apparatus can be enhanced by using all object sizes for a given contrast level to determine a smallest detectable object.

Referring now to FIG. 47, embodiments of ExLCD methods and apparatus can be enhanced by using all object sizes for a given contrast level to determine a smallest detectable object. An improvement of accuracy of detection of the "smallest pin size" is thus obtained by fitting the points to a line and determining where the fitted line crosses the detectability threshold. In other embodiments, an enhancement is made by using all object contrasts for given object size. In FIG. 47, "x" points 4702 indicate detectability values for each object size for a given contrast level. Line 4704 is a linear fit of the detectability values 4702. Location "A" indicates the smallest object size based on the smallest distinct object above a detectability index threshold 4706. Location "B" indicates the smallest object size based on a fit using all object sizes.

A detectability calculation analyzes each object and noise spectrum for sets of objects within the band of contrast levels encompassing the threshold of detectability. In some embodiments, the detectability calculation uses a Non Prewhitening Matched Filter Signal to Noise ratio in which the object signal is reduced by the object contrast reduction factor.

It will be appreciated that some embodiments of the present invention provide a performance function that can be used to reproduce clinical performance for any patient on a scanner that has been characterized. The performance function provides an objective quantifiable scoring scale for qualitative clinical imaging.

In some embodiments of the present invention, the minimum clinical image quality scores can be determined and assigned for various clinical problems by medical researchers. For a particular patient and clinical problem, these scores can be used to determine the precise conditions of operation required for a characterized scanner for a particular scan.

It will be appreciated that some embodiments of the present invention provide at least one or more desirable features, among which may include characterization of the performance of a radiometric imaging apparatus such as a CT scanner at more than one protocol, over a full operating range of the imaging apparatus, or both. Also included may be the adequate handling of smaller pins that are affected by system blurring and/or remedying of the inadequacy of a single protocol contrast performance curve. Also included may be the remedying of inaccuracies that prevent true differentiation of contrast performance between different CT scanners, an adequate description of CIQ, a universal description of CIQ, and the tracking of desired CIQ with patient size. In addition, some advantages that may be realized include less confusion among technologists, and a better way to determine detectability in radiometric imaging systems.

While the invention has been described in terms of various specific embodiments, those skilled in the art will recognize that the invention can be practiced with modification within the spirit and scope of the claims.

REFERENCES

{Barrett 2004} Barrett H H, Myers K J, Foundations of Image Science, 2004 John Wiley & Sons.
{Menke 2005} Jan Menke, MD, "Comparison of Different Body Size Parameters for Individual Dose Adaptation in Body CT of Adults", Radiology 2005; 236:565-571.
{Myers 1987} Myers, K. J and Barrett, H. H. "Addition of a channel mechanism to the ideal observer model", Journal of the Optical Society of America, Vol. 4, Issue 12, pp. 2447-2457.
{AAPM 2011} AAPM Report 204, 2011 "Size Specific Dose Estimates (SSDE) in Pediatric and Adult Body CT Examinations.

What is claimed is:

1. A method for evaluating dose performance of a radiographic imaging system with respect to image quality using a phantom, a channelized hotelling observer module as a model observer, and a printer, a plaque, or an electronic display, said method comprising:
   scanning and producing images for a plurality of sections of the phantom using the radiographic imaging system, wherein the plurality of sections represents a range of patient sizes and doses and wherein the plurality of sections of the phantom contain objects of measurable detectability;
   analyzing the images to determine detectability results for one or more of the objects within the images of the plurality of sections of the phantom, wherein said analyzing comprises using a channelized hotelling observer (CHO) module as a model observer; and
   displaying, via the printer, the plaque, or the electronic display, a continuous detectability performance measurement function using the determined detectability results.

2. A method in accordance with claim 1, wherein said displaying further comprises displaying the continuous detectability performance measurement function as a function of Flux Index to obtain a family of detectability performance measurement functions.

3. A method in accordance with claim 2, wherein said radiographic imaging system is a first radiographic imaging system, and further comprising reproducing imaging performance of the first radiographic imaging system using a second radiographic imaging system, the reproducing comprising:
   translating a family of detectability measure values at a Flux index of the first radiographic imaging system to a family of detectability performance measurement functions of a second radiographic imaging system using the family of detectability performance measurement functions of the first radiographic imaging system and the family of detectability performance measurement functions of the second radiographic imaging system; and
   providing an indication of settings needed to produce said imaging performance on the second radiographic imaging system using a family of Flux Index values of the second radiographic imaging system.

4. A method in accordance with claim 2, further comprising displaying the family of detectability performance measurement functions as a function of mAs at a fixed patient water equivalent diameter $D_{weq}$.

5. A method in accordance with claim 2, further comprising displaying the detectability performance measurement functions as a function of standard dose index CTDIvol at a fixed patient water equivalent diameter $D_{weq}$.

6. A method in accordance with claim 2, further comprising displaying the detectability performance measurement functions as a function of patient water equivalent diameter $D_{weq}$ at a fixed mAs.

7. A method in accordance with claim 1, further comprising:
   determining a first scaling parameter using at least one contrast value of an image relative to a selected contrast reference;
   determining a second scaling parameter using a diameter of an object contained a section of the plurality of sections of the phantom relative to a selected reference object diameter;

scaling the detectability results of a plurality of objects in the phantom using the first scaling parameter and the second scaling parameter; and using the scaled detectability results of the plurality of objects in the phantom to obtain a one-dimensional detectability performance measurement function as a function of Flux Index.

8. A method in accordance with claim 7, wherein said radiographic imaging system is a first radiographic imaging system, said method further comprising:

reproducing imaging performance of the first imaging system using a second imaging system and the one-dimensional detectability performance measurement function of the first imaging system, said reproducing including finding a detectability value on a detectability performance measurement function of the second radiographic imaging system and an associated Flux Index to indicate settings of the second radiographic imaging system needed to reproduce said imaging performance.

9. A method in accordance with claim 7, further comprising displaying the one-dimensional detectability performance measurement function as a function of mAs at a fixed patient water equivalent diameter $D_{weq}$.

10. A method in accordance with claim 7, further comprising displaying the one-dimensional detectability performance measurement function as a function of standard dose index CTDIvol at a fixed patient water equivalent diameter $D_{weq}$.

11. A method in accordance with claim 7, further comprising displaying the one-dimensional detectability performance measurement function as a function of patient water equivalent diameter $D_{weq}$ at a fixed mAs.

12. A method of determining a base extended low contrast detectability performance measurement function as a relation between a Flux Index and a Contrast Index for an operating range for a core operating mode of a radiographic imaging system using actual reconstructed images, the method comprising the steps of:

selecting a plurality of protocols distributed across said operating range of the radiographic imaging system;

imaging a phantom containing a plurality of objects over each of the plurality of protocols;

computing a detectability for each object of the plurality of objects in order to determine a set of ordered pairs of Flux Index and Contrast Index for each object;

determining a smallest detectable object size for each contrast set;

computing the Contrast Index for each protocol for each contrast set; and utilizing the set of ordered pairs of Flux Index and Contrast Index to determine the base extended low contrast detectability performance measurement function for the radiographic imaging system.

13. The method of claim 12, further comprising tracking the base extended low contrast detectability performance measurement function over time.

14. The method of claim 12, wherein said radiographic imaging system is a first computed radiographic imaging system having the base extended low contrast detectability performance measurement function, and further comprising:

(a) performing said method on a second computed radiographic imaging system having a second extended low contrast detectability performance measurement function; and, (b) using said base extended low contrast detectability performance measurement function and said second extended low contrast detectability performance measurement function, determining, for a first clinical protocol on said first computed radiographic imaging system, an equivalent second clinical protocol for at least said second computed radiographic imaging system corresponding to said first clinical protocol.

15. The method of claim 12, wherein said radiographic imaging system is a computed radiographic imaging system and said method further comprising adjusting a scanning protocol of the computed radiographic imaging system to reduce a dosage to a patient while maintaining imaging quality.

16. The method of claim 12, wherein said radiographic imaging system is a first computed radiographic imaging system having a first extended low contrast detectability performance measurement function, and further comprising:

(a) performing said method on a second computed radiographic imaging system having a second extended low contrast detectability performance measurement function; and (b) using said base extended low contrast detectability performance measurement function and said second extended low contrast detectability performance measurement function, identifying protocols on said first computed radiographic imaging system that relate to protocols on said second computed radiographic imaging system having equivalent extended low contrast detectability performance measurement function values.

* * * * *